(12) United States Patent
Hebeisen et al.

(10) Patent No.: US 7,229,999 B2
(45) Date of Patent: Jun. 12, 2007

(54) PYRIDINE-3-CARBOXAMIDE DERIVATIVES AS CB1 INVERSE AGONISTS

(75) Inventors: Paul Hebeisen, Basel (CH); Hans Iding, Rheinfelden (DE); Matthias Heinrich Nettekoven, Grenzach-Wyhlen (DE); Ulrike Obst, Reinach (CH); Stephan Roever, Inzlingen (DE); Beat Wirz, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/397,743

(22) Filed: Apr. 4, 2006

(65) Prior Publication Data

US 2006/0229326 A1 Oct. 12, 2006

(30) Foreign Application Priority Data

Apr. 6, 2005 (EP) .................................. 05102709

(51) Int. Cl.
*A61K 31/44* (2006.01)
*A51N 43/54* (2006.01)
*C07D 213/22* (2006.01)
*C07D 213/56* (2006.01)
*C07D 401/00* (2006.01)

(52) U.S. Cl. .................. 514/256; 514/355; 514/356; 546/257; 546/272.1; 546/316; 544/333

(58) Field of Classification Search ................ 514/256, 514/355, 356; 546/257, 272.1, 316; 544/333
See application file for complete search history.

(56) References Cited

U.S. PATENT DOCUMENTS

| | | | |
|---|---|---|---|
| 3,940,418 A | 2/1976 | Hamilton | |
| 5,462,960 A | 10/1995 | Barth et al. | |
| 5,596,106 A | 1/1997 | Cullinan et al. | |
| 5,624,941 A | 4/1997 | Barth et al. | |
| 5,756,524 A * | 5/1998 | Riordan et al. | 514/346 |
| 6,028,084 A | 2/2000 | Barth et al. | |
| 6,355,631 B1 | 3/2002 | Achard et al. | |
| 6,479,479 B2 | 11/2002 | Achard et al. | |
| 6,509,367 B1 | 1/2003 | Martin et al. | |
| 6,518,264 B2 | 2/2003 | Achard et al. | |
| 6,566,356 B2 | 5/2003 | Achard et al. | |
| 6,734,176 B2 | 5/2004 | Achard et al. | |
| 6,858,603 B2 | 2/2005 | Achard et al. | |
| 6,872,717 B2 | 3/2005 | Achard et al. | |
| 2001/0027193 A1 | 10/2001 | Achard et al. | |
| 2002/0019383 A1 | 2/2002 | Achard et al. | |
| 2002/0035102 A1 | 3/2002 | Achard et al. | |
| 2003/0055033 A1 | 3/2003 | Achard et al. | |
| 2003/0119810 A1 | 6/2003 | Achard et al. | |
| 2003/0162808 A1 | 8/2003 | Achard et al. | |
| 2004/0157823 A1 | 8/2004 | Achard et al. | |
| 2004/0235816 A1 | 11/2004 | Achard et al. | |
| 2004/0259887 A1 | 12/2004 | Dow | |
| 2005/0130953 A1 | 6/2005 | Achard et al. | |

FOREIGN PATENT DOCUMENTS

| | | |
|---|---|---|
| EP | 576357 | 12/1993 |
| EP | 656354 | 6/1995 |
| EP | 658546 | 6/1995 |
| FR | 2783246 A1 | 3/2000 |
| FR | 2805810 A1 | 9/2001 |
| FR | 2805817 A1 | 9/2001 |
| FR | 2805818 A1 | 9/2001 |
| FR | 2856684 | 12/2004 |
| WO | WO 96/02248 | 2/1996 |
| WO | WO 97/19063 | 5/1997 |
| WO | WO 98/031227 | 7/1998 |
| WO | WO 98/041519 | 9/1998 |
| WO | WO 98/043635 | 10/1998 |
| WO | WO 98/043636 | 10/1998 |
| WO | WO 00/15609 | 3/2000 |
| WO | WO 00/46209 | 8/2000 |
| WO | WO 01/32663 | 5/2001 |
| WO | WO 01/64632 | 9/2001 |

(Continued)

OTHER PUBLICATIONS

D.Shire, et al., J. Biol. Chem. 270 (8) (1995) 3726-31.

(Continued)

*Primary Examiner*—Thomas McKenzie
*Assistant Examiner*—Binta Robinson
(74) *Attorney, Agent, or Firm*—George W. Johnston; Dennis P. Tramaloni; Samuel H. Megerditchian

(57) ABSTRACT

The present invention relates to compounds of the formula

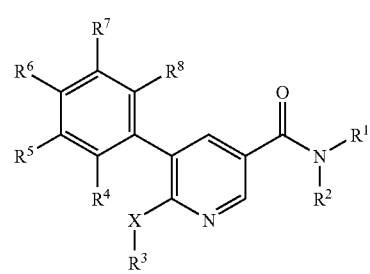

I wherein X and $R^1$ to $R^8$ are as defined in the description and claims, and pharmaceutically acceptable salts thereof. The compounds are useful for the treatment and/or prophylaxis of diseases which are associated with the modulation of CB1 receptors, such as obesity.

20 Claims, No Drawings

FOREIGN PATENT DOCUMENTS

| | | |
|---|---|---|
| WO | WO 01/64633 | 9/2001 |
| WO | WO 01/64634 | 9/2001 |
| WO | WO 01/70700 | 9/2001 |
| WO | WO 02/28346 | 4/2002 |
| WO | WO 03/051850 | 6/2003 |
| WO | WO 03/051851 | 6/2003 |
| WO | WO 03/082191 A2 | 10/2003 |
| WO | WO 03/084930 | 10/2003 |
| WO | WO 2004/110453 | 12/2004 |
| WO | WO 2004/111033 | 12/2004 |
| WO | WO 2004/111034 | 12/2004 |
| WO | WO 2004/111038 | 12/2004 |
| WO | WO 2004/111039 | 12/2004 |

OTHER PUBLICATIONS

E. Ryberg, et. al., FEBS Lett. 579 (2005) 259-264.
S. Munro, et. al., Nature 365 (1993) 61-61.
Y. Gaoni, et. al., J. Am. Chem. Soc., 86 (1964) 1646).
R. G. Pertwee, Pharmaceut. Sci. 3 (11) (1997) 539-545.
E. M. Williamson, F. J. Evans, Drugs 60 (6) (2000) 1303-1314.
R.G. Pertwee, Curr. Med. Chem., 6 (8) (1999) 635-664.
W.A. Devane, et. al., Science 258 (1992) 1946-9.
V. Di Marzo, et. al., Trends in Neuroscience 21 (12) (1998) 521-8.
A. C. Porter, C.C. Felder, Pharmacol. Ther., 90 (1) (2001) 45-60.
C.M. Williams, et. al., Psychopharmacology 143 (3) (1999) 315-317.
C. C. Felder, et. al., Proc. Natl. Acad. Sci. U. S. A. 90 (16) (1993) 7656-60).
G. Colombo, et. al., Life Sci. 63 (8) (1998) L113-PL117.
V. Di Marzo, S. K. Goparaju, L. Wang, J. Liu, S. Bitkai, Z. Jarai, F. Fezza, G. I. Miura, R. D. Palmiter, T. Suguira, G. Kunos, Nature 410 (6830) 822-825.
F. Barth, et. al., "*Cannabinoid antagonists: From research tools to potential new drugs.*" Abstracts of Papers, 222nd ACS National Meeting, Chicago, IL, United States, Aug. 26-30, 2001.
AAI; M. Pacheco, S. R. Childers, R. Arnold, F. Casiano, S. J. Ward, J. Pharmacol. Exp. Ther. 257 (1) (1991) 170-183.
F. M. Casiano, et. al., NIDA Res. Monogr. 105 (1991) 295-6.
K. Hosohata, et. al., Life Sci. 61 (1997) 115-118.
R. Pertwee, et. al., Life Sci. 56 (23-24) (1995) 1949-55.
C. C. Felder, et. al., J. Pharmacol. Exp. Ther. 284 (1) (1998) 291-7.
M. Kanyonyo, et. al., Bioorg. Med. Chem. Lett. 9 (15) (1999) 2233-2236.
F. Ooms, et. al., J. Med. Chem. 45 (9) (2002) 1748-1756.
R. Mechoulam (Ed.) in "*Cannabinoids as therapeutic Agents*", 1986, pp. 1-20, CRC Press.

* cited by examiner

PYRIDINE-3-CARBOXAMIDE DERIVATIVES AS CB1 INVERSE AGONISTS

PRIORITY TO RELATED APPLICATIONS

This application claims the benefit of European Application No. 05102709.2, filed Apr. 6, 2005, which is hereby incorporated by reference in its entirety.

FIELD OF THE INVENTION

The present invention is directed to novel 3-pyridinecarboxamide derivatives, their manufacture, pharmaceutical compositions containing them and their use as medicaments. The active compounds of the present invention are useful in treating obesity and other disorders.

In particular, the present invention relates to compounds of the formula I

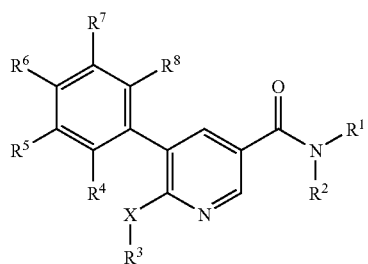

and pharmaceutically acceptable salts thereof.

Compounds of formula I of the present invention are modulators of the $CB_1$ receptor.

All documents cited or relied upon below are expressly incorporated herein by reference.

BACKGROUND

Two different subtypes of cannabinoid receptors ($CB_1$ and $CB_2$) have been isolated and both belong to G protein coupled receptor superfamily. Alternative spliced forms of $CB_1$, $CB_{1A}$ and $CB_{1B}$ have also been described, but are expressed only at low levels in the tissues tested. (D. Shire, C. Carrillon, M. Kaghad, B. Calandra, M. Rinaldi-Carmona, G. Le Fur, D. Caput, P. Ferrara, J. Biol. Chem. 270 (8) (1995) 3726–31; E. Ryberg, H. K. Vu, N. Larsson, T. Groblewski, S. Hjorth, T. Elebring, S. Sjögren, P. J. Greasley, FEBS Lett. 579 (2005) 259–264). The $CB_1$ receptor is mainly located in the brain and to a lesser extent in several peripheral organs, whereas the $CB_2$ receptor is predominately distributed in the periphery primarily localized in spleen and cells of the immune system (S. Munro, K. L. Thomas, M. Abu-Shaar, Nature 365 (1993) 61—61).

Therefore in order to avoid side effects a $CB_1$-selective compound is desirable. $\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *cannabis sativa* (marijuanan), and has medicinal uses (R. Mechoulam (Ed.) in *"Cannabinoids as therapeutic Agents"*, 1986, pp. 1–20, CRC Press). $\Delta^9$-THC is a non-selective $CB_{1/2}$ receptor agonist and is available in the USA as dronabinol (Marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539–545, E. M. Williamson, F. J. Evans, Drugs 60 (6) (2000) 1303–1314).

Anandamide (arachidonylethanolamide) was identified as the endogenous ligand (agonist) for $CB_1$ (R. G. Pertwee, Curr. Med. Chem., 6 (8) (1999) 635–664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946–9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521–8), thereby affecting neurotransmitter release and/or action, which decreases the release of neurotransmitter (A. C. Porter, C. C. Felder, Pharmacol. Ther., 90 (1) (2001) 45–60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315–317; C. C. Felder, E. M. Briley, J. Axelrod, J. T. Simpson, K. Mackie, W. A. Devane, Proc. Natl. Acad. Sci. U.S.A. 90 (16) (1993) 7656–60) and cause appetite suppression and weight loss (G. Colombo, R. Agabio, G. Diaz, C. Lobina, R. Reali, G. L. Gessa, Life Sci. 63 (8) (1998) L113–PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822–825).

At least two CB1 selective antagonist/inverse agonists (SR-141716 and SLV-319) are currently undergoing clinical trials for the treatment of obesity and/or smoking cessation. In a double blind placebo-controlled study, at the doses of 10 and 20 mg daily, SR 141716 significantly reduced body weight when compared to placebo (F. Barth, M. Rinaldi-Carmona, M. Amone, H. Heshmati, G. Le Fur, "*Cannabinoid antagonists: From research tools to potential new drugs.*" Abstracts of Papers, 222nd ACS National Meeting, Chicago, Ill., United States, Aug. 26–30, 2001). SR-141716 reduced body weight, waist circumference and improved metabolic parameters (plasma HDL, triglycerides and insulin sensitivity) in several phase III studies (RIO-lipids, RIO-Europe and RIO-North America). Additionally SR-141716 has shown efficacy in a phase III trial for smoking cessation (STRATUS-US).

Substituted pyrazoles having activity against the cannabinoid receptors are disclosed in U.S. Pat. Nos. 5,624,941, 6,028,084 and 6,509,367, in PCT patent applications WO 98/031227, WO 98/041519, WO 98/043636, WO 98/043635, WO 04/192667, WO 04/0099157 and in patent application EP 658546.

Substituted pyridines, pyrimidines and pyrazines having activity against the cannabinoid receptors are disclosed in U.S. patent application Ser. No. 04/0259887 and in PCT patent applications WO 03/051850, WO 03/051851, WO 03/084930, WO 04/110453, WO 04/111033, WO 04/111034, WO 04/111038, WO 04/111039 and in patent application FR 2856684.

Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170–183). Examples thereof are 6-bromo-(WIN54661; F. M. Casiano, R. Arnold, D. Haycock, J. Kuster, S. J. Ward, NIDA Res. Monogr. 105 (1991) 295–6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23–24) (1995) 1949–55). Furthermore, arylbenzo[b]thiophene and benzo[b]furan derivatives (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291–7) as disclosed in WO 96/02248 or U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233–2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748–1756) are known to antagonize the $CB_1$ receptor respectively act as an inverse agonist on the $hCB_1$ receptor. In WO 00/15609 (FR2783246-A1), WO 01/64634 (FR2805817-A1), WO 02/28346, WO 01/64632 (FR2805818-A1) and WO 01/64633 (FR2805810-A1) are disclosed substituted 1-bis(aryl)methyl-azetidines derivatives as antagonists of $CB_1$. In WO 01/70700 4,5-dihydro-1H-pyrazole derivatives are described as $CB_1$ antagonists. In several patent documents bridged and non-bridged 1,5-diphenyl-3-pyrazolecarboxamide derivatives are disclosed as $CB_1$ antagonists/inverse agonists (WO 01/32663, WO 00/46209, WO 97/19063, EP 658546, EP 656354, U.S. Pat. No. 5,624,941, EP 576357 and U.S. Pat. No. 3,940,418). However, there still remains a need for potent low molecular weight CB1 modulators that have improved pharmacokinetic and pharmacodynamic properties suitable for use as human pharmaceuticals.

SUMMARY OF THE INVENTION

In one embodiment of the present invention, provided is a compound of the formula I:

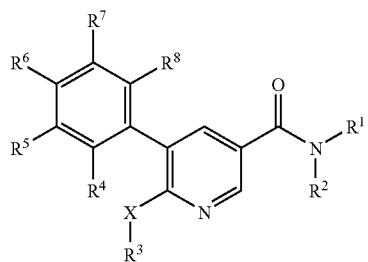

wherein:
$R^1$ is selected from the group consisting of
cycloalkyl which is unsubstituted or substituted by hydroxy or lower alkoxy, lower hydroxyalkyl, lower hydroxyhalogenalkyl, —$CH_2$—$CR^9R^{10}$-cycloalkyl, and
—$CR^{11}R^{12}$—$COOR^{13}$;
$R^9$ is hydrogen or lower alkyl;
$R^{10}$ is hydrogen, hydroxy or lower alkoxy;
$R^{11}$ and $R^{12}$ independently from each other are hydrogen or lower alkyl;
$R^{13}$ is lower alkyl;
$R^2$ is hydrogen;
X is O or $NR^{14}$;
$R^{14}$ is hydrogen or lower alkyl;
$R^3$ is selected from the group consisting of lower alkyl,
cycloalkyl,
lower cycloalkylalkyl,
lower alkoxyalkyl,
lower halogenalkyl,
lower carbamoylalkyl,
lower phenylalkyl,
lower heterocyclylalkyl,
lower heteroarylalkyl wherein the heteroaryl group is unsubstituted or mono- or di-substituted by halogen, and
phenyl which is unsubstituted or mono- or di-substituted by halogen;
or $R^3$ and $R^{14}$ together with the nitrogen atom they are attached to form a 5-, 6- or 7-membered heterocyclic ring;
$R^4$ and $R^8$ independently from each other are hydrogen or halogen;
$R^5$ and $R^7$ independently from each other are selected from the group consisting of hydrogen, halogen, lower halogenalkyl, lower halogenalkoxy and cyano;
$R^6$ is selected from the group consisting of hydrogen, halogen, lower halogenalkyl, lower halogenalkoxy and cyano;

and pharmaceutically acceptable salts thereof.

In another embodiment of the present invention, provided is a process for the manufacture of a compound according to formula I above, comprising the steps of: coupling a compound of formula II

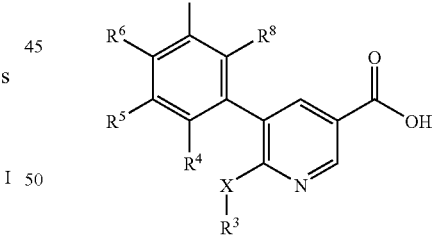

wherein $R^3$ to $R^8$ are as defined in claim 1, with an amine of the formula $$H—NR^1R^2 \quad\quad III$$

wherein $R^1$ and $R^2$ are as defined above, with the help of an coupling agent under basic conditions, and, if desired, converting the resulting compound of formula I into a pharmaceutically acceptable salt thereof.

In a further embodiment of the present invention, provided is a process for the manufacture of a compound according to formula I, comprising the steps of: coupling a compound of formula

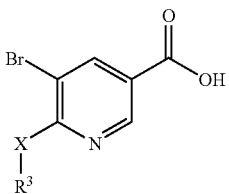

wherein X and R³ are as defined herein before, with an aryl metal species of the formula

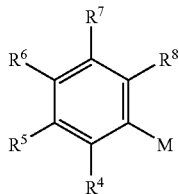

wherein R⁴ to R⁸ are as defined herein before and M means boronic acid or a boronic acid ester, in the presence of a Pd catalyst under basic conditions, and, if desired, converting the resulting compound of formula I into a pharmaceutically acceptable salt thereof.

In a yet another embodiment of the present invention, provided is a pharmaceutical composition, comprising a therapeutically effective amount of a compound according to formula I and a pharmaceutically acceptable carrier and/or adjuvant.

In a still further embodiment of the present invention, provided is a method for the treatment and/or prophylaxis of diseases or disorders which are associated with the modulation of the CB1 receptors, comprising the step of administering a therapeutically effective amount of a compound according to formula I to a human being or animal in need thereof.

DETAILED DESCRIPTION

It is therefore an embodiment of this invention to provide selective, directly acting CB1 receptor antagonists/inverse agonists. Such antagonists/inverse antagonists are useful in medical therapy, particularly in the treatment and/or prevention of diseases which are associated with the modulation of CB1 receptors.

Unless otherwise indicated, the following definitions are set forth to illustrate and define the meaning and scope of the various terms used to describe the invention herein. In this specification the term "lower" is used to mean a group consisting of one to seven, preferably of one to four carbon atom(s).

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined above which is mono- or multiply substituted with an lower alkoxy group as defined above. Examples of lower alkoxyalkyl groups are e.g. —CH₂—O—CH₃, —CH₂—CH₂—O—CH₃, —CH₂—O—CH₂—CH₃ and the groups specifically exemplified herein. Most preferably, lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Preferred are $C_{3-7}$-hydroxyalkyl groups. Examples of lower hydroxyalkyl groups are 2-hydroxybutyl, 3-hydroxy-2,2-dimethylpropyl and the groups specifically exemplified therein.

The term "halogen" refers to fluorine, chlorine, bromine and iodine. Preferred "halogen" groups are fluorine or chlorine.

The term "lower halogenalkyl" or "halogen-$C_{1-7}$-alkyl" refers to lower alkyl groups which are mono- or multiply substituted with halogen, preferably with fluoro or chloro, most preferably with fluoro. Examples of lower halogenalkyl groups are e.g. —CF₃, —CHF₂, —CH₂Cl, —CH₂CF₃, —CH(CF₃)₂, —CF₂—CF₃ and the groups specifically exemplified herein.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyhalogenalkyl" or "hydroxy-halogen-$C_{1-7}$-alkyl" refers to lower halogenalkyl groups as defined herein before which are additionally substituted with a hydroxy group. Examples of lower hydroxyhalogenalkyl groups are e.g. 3,3,3-trifluoro-2-hydroxy-propyl and the groups specifically exemplified herein.

The term "carbamoyl" refers to the group —CO—NH₂.

The term "lower carbamoylalkyl" or "carbamoyl-$C_{1-7}$-alkyl" refers to lower alkyl groups as defined above wherein one of the hydrogen atoms of the lower alkyl group is replaced by a carbamoyl group. Examples of preferred lower carbamoylalkyl groups are 3-carbamoylpropyl, 4-carbamoylbutyl and 5-carbamoylpentyl, most preferably 4-carbamoylbutyl.

The term "cycloalkyl" or "$C_{3-7}$-cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclopropyl being especially preferred.

The term "lower cycloalkylalkyl" or "$C_{3-7}$-cycloalkyl-$C_{1-7}$-alkyl" refers to a lower alkyl group as defined above which is mono- or multiply substituted with a cycloalkyl group as defined above. Examples of lower cycloalkylalkyl groups are e.g. —CH₂-cyclopropyl, —CH₂—CH₂-cyclopropyl, —CH₂-cyclopentyl and the groups specifically exemplified herein.

The term "heterocyclyl" refers to a saturated or partly unsaturated 3-, 4-, 5-, 6- or 7-membered ring which can comprise one, two or three atoms selected from nitrogen, oxygen and/or sulphur. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuryl, tetrahydrofuryl, dihydropyranyl, tetrahydropyranyl, and thiomorpholinyl. Preferred heterocyclyl groups are oxetanyl and [1,3]dioxolanyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, or pyrrolyl. The heteroaryl group can optionally be mono- or disubstituted by lower alkyl. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrimidinyl, imidazolyl, triazolyl, and thiazolyl which groups can optionally be mono- or disubstituted by lower alkyl. Especially preferred are 3-methylisoxazolyl, 5-methylisoxazolyl, pyridyl, 3-methylpyridyl, pyrimidinyl, 1-methylimidazolyl, 2-methyl[1,2,4]triazolyl and 4-methylthiazolyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "form a 5-, 6- or 7-membered heterocyclic ring" refers to a N-heterocyclic ring such as pyrrolidinyl, piperidinyl or azepanyl. Preferred is piperidinyl.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In detail, the present invention relates to compounds of the general formula

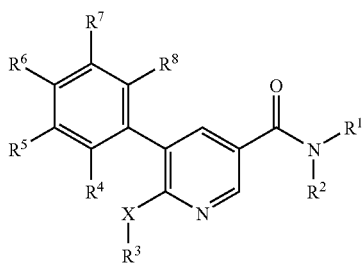

I wherein
$R^1$ is selected from the group consisting of
cycloalkyl which is unsubstituted or substituted by hydroxy or lower alkoxy, lower hydroxyalkyl, lower hydroxyhalogenalkyl,
—$CH_2$—$CR^9R^{10}$-cycloalkyl, and
—$CR^{11}R^{12}$—$COOR^{13}$;
$R^9$ is hydrogen or lower alkyl;
$R^{10}$ is hydrogen, hydroxy or lower alkoxy;
$R^{11}$ and $R^{12}$ independently from each other are hydrogen or lower alkyl;
$R^{13}$ is lower alkyl;
$R^2$ is hydrogen;
X is O or $NR^{14}$;
$R^{14}$ is hydrogen or lower alkyl;
$R^3$ is selected from the group consisting of lower alkyl, cycloalkyl,
lower cycloalkylalkyl,
lower alkoxyalkyl,
lower halogenalkyl,
lower carbamoylalkyl,
lower phenylalkyl,
lower heterocyclylalkyl,
lower heteroarylalkyl wherein the heteroaryl group is unsubstituted or mono- or di-substituted by lower alkyl, and
phenyl which is unsubstituted or mono- or di-substituted by halogen;
or $R^3$ and $R^{14}$ together with the nitrogen atom they are attached to form a 5-, 6- or 7-membered heterocyclic ring;
$R^4$ and $R^8$ independently from each other are hydrogen or halogen;
$R^5$ and $R^7$ independently from each other are selected from the group consisting of hydrogen, halogen, lower halogenalkyl, lower halogenalkoxy and cyano;
$R^6$ is selected from the group consisting of hydrogen, halogen, lower halogenalkyl, lower halogenalkoxy and cyano;

and pharmaceutically acceptable salts thereof.

Preferred compounds of formula I according to the present invention are those, wherein X is O.

Also preferred are compounds of formula I of the invention, wherein $R^1$ is cycloalkyl which is unsubstituted or substituted by hydroxy or lower alkoxy, with those compounds, wherein $R^1$ is cycloalkyl substituted by hydroxy, being especially preferred.

Another group of preferred compounds of formula I according to the present invention are those, wherein $R^1$ is —$CH_2$—$CR^9R^{10}$-cycloalkyl and wherein $R^9$ is hydrogen or lower alkyl and $R^{10}$ is hydrogen, hydroxy or lower alkoxy, with those compounds of formula I, wherein $R^1$ is —$CH_2$—$CR^9R^{10}$-cycloalkyl and wherein $R^9$ is hydrogen and $R^{10}$ is hydroxy, being more preferred.

Furthermore, compounds of formula I according to the invention are preferred, wherein $R^3$ is selected from the group consisting of lower alkyl, cycloalkyl, lower cycloalkylalkyl, lower alkoxyalkyl, lower halogenalkyl, lower carbamoylalkyl, lower phenylalkyl, lower heterocyclylalkyl, lower heteroarylalkyl wherein the heteroaryl group is unsubstituted or mono- or di-substituted by halogen, and phenyl which is unsubstituted or mono- or di-substituted by halogen, with those compounds of formula I, wherein $R^3$ is selected from lower cycloalkylalkyl, lower alkoxyalkyl and lower heteroarylalkyl, being more preferred.

Especially preferred are compounds of formula I, wherein $R^3$ is lower cycloalkylalkyl, or wherein $R^3$ is lower alkoxyalkyl.

Furthermore, compounds of formula I of the present invention are preferred, wherein $R^4$ and $R^8$ independently from each other are hydrogen or halogen, $R^5$ and $R^7$ independently from each other are selected from the group consisting of hydrogen, halogen, lower halogenalkyl, lower halogenalkoxy and cyano, $R^6$ is selected from the group consisting of hydrogen, halogen, lower halogenalkyl, lower halogenalkoxy and cyano, and not all of $R^4$ to $R^8$ are hydrogen.

Also preferred are compounds of formula I according to the invention, wherein $R^6$ is halogen or lower halogenalkyl and $R^4$, $R^5$, $R^7$ and $R^8$ are hydrogen.

Further preferred compounds of formula I according to the invention are those, wherein $R^4$ is halogen, $R^7$ is halogen or lower halogenalkyl and $R^5$, $R^6$ and $R^8$ are hydrogen.

In addition, compounds of formula I according the invention are preferred, wherein X is $NR^{14}$, and $R^{14}$ is hydrogen or lower alkyl or $R^{14}$ together with $R^3$ and with the nitrogen atom they are attached to form a 5-, 6- or 7-membered heterocyclic ring.

A further preferred group of compounds of formula I of the present invention are compounds having the formula

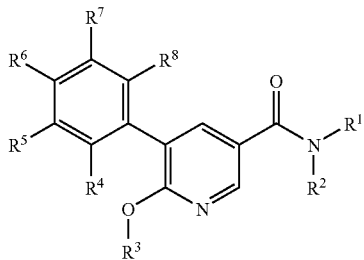

I-A wherein
$R^1$ is selected from the group consisting of
cycloalkyl which is unsubstituted or substituted by hydroxy or lower alkoxy,
—$CH_2$—$CR^9R^{10}$-cycloalkyl, and
—$CR^{11}R^{12}$—$COOR^{13}$;
$R^9$ is hydrogen or lower alkyl;
$R^{10}$ is hydrogen, hydroxy or lower alkoxy;
$R^{11}$ and $R^{12}$ independently from each other are hydrogen or lower alkyl;
$R^{13}$ is lower alkyl;
$R^2$ is hydrogen;
$R^3$ is selected from the group consisting of lower alkyl, cycloalkyl,
lower cycloalkylalkyl,
lower alkoxyalkyl, and
phenyl which is unsubstituted or mono- or di-substituted by halogen;
$R^4$ and $R^8$ independently from each other are hydrogen or halogen;
$R^5$ and $R^7$ independently from each other are selected from the group consisting of hydrogen, halogen and lower halogenalkyl;
$R^6$ is selected from the group consisting of hydrogen, halogen and lower halogenalkyl;

and pharmaceutically acceptable salts thereof.

Preferred are compounds of formula I-A as defined above, wherein $R^1$ is cycloalkyl which is unsubstituted or substituted by hydroxy or lower alkoxy. Especially preferred are those compounds of formula I, wherein $R^1$ is cycloalkyl substituted by hydroxy. Most preferably, $R^1$ is cyclohexyl substituted by hydroxy.

Preferred are also compounds of formula I-A according to the present invention, wherein $R^1$ is —$CH_2$—$CR^9R^{10}$-cycloalkyl and wherein $R^9$ is hydrogen or lower alkyl and $R^{10}$ is hydrogen, hydroxy or lower alkoxy. Especially preferred are compounds of formula I, wherein $R^1$ is —$CH_2$—$CR^9R^{10}$-cycloalkyl and wherein $R^9$ is hydrogen and $R^{10}$ is hydroxy. For this group of compounds, most preferred cycloalkyl is cyclopropyl.

Furthermore, compounds of formula I-A according to the present invention are preferred, wherein $R^3$ is selected from the group consisting of lower alkyl, cycloalkyl and lower cycloalkylalkyl.

More preferred are those compounds of formula I-A, wherein $R^3$ is lower alkyl or lower cycloalkylalkyl.

Especially preferred are compounds of formula I-A, wherein $R^3$ is lower alkyl. Most preferably, $R^3$ is butyl.

Also especially preferred are compounds of formula I-A, wherein $R^3$ is lower cycloalkylalkyl. More preferably, $R^3$ is cycloalkylmethyl. Most preferably, $R^3$ is cyclopropylmethyl.

Furthermore, compounds of formula I-A of the present invention, wherein $R^4$ and $R^8$ independently from each other are hydrogen or halogen, $R^5$ and $R^7$ independently from each other are selected from the group consisting of hydrogen, halogen and lower halogenalkyl; $R^6$ is selected from the group consisting of hydrogen, halogen and lower halogenalkyl, and not all of $R^4$ to $R^8$ are hydrogen, are preferred.

Especially preferred are those compounds of formula I-A, wherein $R^6$ is halogen or lower halogenalkyl and $R^4$, $R^5$, $R^7$ and $R^8$ are hydrogen. More preferably, $R^6$ is halogen. Most preferably, $R^6$ is fluoro or chloro.

Further especially preferred compounds of formula I-A of the present invention are those, wherein $R^4$ is halogen, $R^7$ is halogen or lower halogenalkyl and $R^5$, $R^6$ and $R^8$ are hydrogen. More preferably, $R^4$ is halogen, $R^7$ is lower halogenalkyl and $R^5$, $R^6$ and $R^8$ are hydrogen. Most preferred $R^4$ is fluoro and $R^7$ is trifluoromethyl.

Preferred compounds of general formula I of the present invention are the following compounds:
5-(2-chloro-5-trifluoromethyl-phenyl)-6-cyclopentyloxy-N-((1R,2R)-2-hydroxy-cyclohexyl)-nicotinamide,
6-butoxy-5-(2-fluoro-5-trifluoromethyl-phenyl)-N-((1R,2R)-2-hydroxy-cyclohexyl)-nicotinamide,
6-butoxy-5-(4-chloro-phenyl)-N-((1R,2R)-2-hydroxy-cyclohexyl)-nicotinamide,
6-butoxy-5-(4-chloro-phenyl)-N-(2-cyclopropyl-2-hydroxy-propyl)-nicotinamide,
5-(4-chloro-phenyl)-6-cyclopropylmethoxy-N-((1R,2R)-2-hydroxy-cyclohexyl)-nicotinamide,
5-(4-chloro-phenyl)-N-(2-cyclopropyl-2-hydroxy-propyl)-6-cyclopropylmethoxy-nicotinamide,
6-cyclopropylmethoxy-5-(2-fluoro-5-trifluoromethyl-phenyl)-N-((1R,2R)-2-hydroxy-cyclohexyl)-nicotinamide,
6-butoxy-5-(2-chloro-5-trifluoromethyl-phenyl)-N-((1R,2R)-2-hydroxy-cyclohexyl)-nicotinamide,
5-(2-chloro-5-trifluoromethyl-phenyl)-6-cyclopropyl-methoxy-N-((1R,2R)-2-hydroxy-cyclohexyl)-nicotinamide,
6-butoxy-5-(2,4-dichloro-phenyl)-N-((1R,2R)-2-hydroxy-cyclohexyl)-nicotinamide,
5-(2,4-dichloro-phenyl)-N-((1R,2R)-2-hydroxy-cyclohexyl)-6-propoxy-nicotinamide,
5-(2,4-dichloro-phenyl)-N-((1R,2R)-2-hydroxy-cyclohexyl)-6-pentyloxy-nicotinamide,
N-(2-cyclopropyl-2-hydroxy-propyl)-5-(2,4-dichloro-phenyl)-6-(2-methoxy-ethoxy)-nicotinamide, 6-cyclopropylmethoxy-5-(2,4-dichloro-phenyl)-N-((1R,2R)-2-hydroxy-cyclohexyl)-nicotinamide,
5-(4-chloro-phenyl)-N-(2-cyclopropyl-2-hydroxy-propyl)-6-(2-methoxy-ethoxy)-nicotinamide,
5-(4-chloro-phenyl)-N-((1R,2R)-2-hydroxy-cyclohexyl)-6-(2-methoxy-ethoxy)-nicotinamide,
5-(4-chloro-phenyl)-N-(trans-2-hydroxy-cyclohexyl)-6-(2-methoxy-ethoxy)-nicotinamide,
5-(4-chloro-phenyl)-N-(2-cyclopropyl-2-hydroxy-propyl)-6-(3-methoxy-propoxy)-nicotinamide,
5-(4-chloro-phenyl)-N-((1R,2R)-2-hydroxy-cyclohexyl)-6-(3-methoxy-propoxy)-nicotinamide,
6-benzylamino-5-(4-chloro-phenyl)-N-((1R,2R)-2-hydroxy-cyclohexyl)-nicotinamide,
5-(4-chloro-phenyl)-6-(cyclopropylmethyl-amino)-N-((1R,2R)-2-hydroxy-cyclohexyl)-nicotinamide,
5-(4-chloro-phenyl)-N-(2-cyclopropyl-2-hydroxy-propyl)-6-(2-methoxy-ethylamino)-nicotinamide,
N-((trans)-2-hydroxy-cyclohexyl)-6-(2-methoxy-ethoxy)-5-(4-trifluoromethyl-phenyl)-nicotinamide,
N-((trans)-2-hydroxy-cyclohexyl)-6-(2-methoxy-ethoxy)-5-(4-trifluoromethoxy-phenyl)-nicotinamide,
6-cyclopropylmethoxy-5-(3,4-difluoro-phenyl)-N-((trans)-2-hydroxy-cyclohexyl)-nicotinamide,
6-cyclopropylmethoxy-5-(4-fluoro-phenyl)-N-((trans)-2-hydroxy-cyclohexyl)-nicotinamide,
6-cyclopropylmethoxy-N-((trans)-2-hydroxy-cyclohexyl)-5-(4-trifluoromethyl-phenyl)-nicotinamide,
6-cyclopropylmethoxy-N-((trans)-2-hydroxy-cyclohexyl)-5-(4-trifluoromethoxy-phenyl)-nicotinamide,
5-(4-cyano-phenyl)-6-cyclopropylmethoxy-N-((1S,2S)-2-hydroxy-cyclohexyl)-nicotinamide,
(RS)-5-(4-chloro-phenyl)-N-(2-hydroxy-butyl)-6-(2-methoxy-ethoxy)-nicotinamide,
(RS)-5-(4-chloro-phenyl)-6-(2-methoxy-ethoxy)-N-(3,3,3-trifluoro-2-hydroxy-propyl)-nicotinamide,
6-benzyloxy-5-(4-chloro-phenyl)-N-((1R,2R)-2-hydroxy-cyclohexyl)-nicotinamide,
5-(4-chloro-phenyl)-N-(3-hydroxy-2,2-dimethyl-propyl)-6-(2-methoxy-ethoxy)-nicotinamide,
(RS)-5-(4-chloro-phenyl)-N-(2-hydroxymethyl-butyl)-6-(2-methoxy-ethoxy)-nicotinamide,
5-(4-chloro-phenyl)-N-((1RS,2RS)-2-hydroxy-cyclohexylmethyl)-6-(2-methoxy-ethoxy)-nicotinamide,
5-(4-chloro-phenyl)-N-((1R,2R)-2-methoxy-cyclohexyl)-6-(2-methoxy-ethoxy)-nicotinamide,
5-(4-chloro-phenyl)-N-((1SR,2RS)-2-hydroxy-cyclohexylmethyl)-6-(2-methoxy-ethoxy)-nicotinamide,
5-(4-chloro-phenyl)-N-(1-hydroxy-cyclohexylmethyl)-6-(2-methoxy-ethoxy)-nicotinamide,
5-(4-chloro-phenyl)-N-((1R,2R)-2-hydroxy-cyclohexyl)-6-(1-methyl-cyclopropylmethoxy)-nicotinamide,
(−)-5-(4-chloro-phenyl)-N-(2-cyclopropyl-2-hydroxy-propyl)-6-(2-methoxy-ethoxy)-nicotinamide,
(+)-5-(4-chloro-phenyl)-N-(2-cyclopropyl-2-hydroxy-propyl)-6-(2-methoxy-ethoxy)-nicotinamide,
5-(4-chloro-phenyl)-6-cyclopentylmethoxy-N-((R,2R)-2-hydroxy-cyclohexyl)-nicotinamide,
5-(4-chloro-phenyl)-6-(2-cyclopropyl-ethoxy)-N-((1R,2R)-2-hydroxy-cyclohexyl)-nicotinamide,
5-(4-chloro-phenyl)-6-cyclobutylmethoxy-N-((1R,2R)-2-hydroxy-cyclohexyl)-nicotinamide,
5-(4-chloro-phenyl)-6-(3,3-dimethyl-butoxy)-N-((1R,2R)-2-hydroxy-cyclohexyl)-nicotinamide,
5-(4-chloro-phenyl)-N-((1RS,2RS)-2-hydroxy-cyclohexylmethyl)-6-(1-methyl-cyclopropylmethoxy)-nicotinamide,
6-benzyloxy-5-(4-chloro-phenyl)-N-((1RS,2RS)-2-hydroxy-cyclohexylmethyl)-nicotinamide,
5-(4-fluoro-phenyl)-N-((1R,2R)-2-hydroxy-cyclohexyl)-6-(2-methoxy-ethoxy)-nicotinamide,
N-((1R,2R)-2-hydroxy-cyclohexyl)-6-(2-methoxy-ethoxy)-5-(4-trifluoromethyl-phenyl)-nicotinamide,
N-((1R,2R)-2-hydroxy-cyclohexyl)-6-(2-methoxy-ethoxy)-5-(4-trifluoromethoxy-phenyl)-nicotinamide,
5-(4-chloro-phenyl)-N-((1R,2R)-2-hydroxy-cyclohexyl)-6-(2-isopropoxy-ethoxy)-nicotinamide,
5-(4-fluoro-phenyl)-N-((1R,2R)-2-hydroxy-cyclohexyl)-6-(2-isopropoxy-ethoxy)-nicotinamide,
5-(4-chloro-phenyl)-N-((1R,2R)-2-hydroxy-cyclohexyl)-6-[(2-methoxy-ethyl)-methyl-amino]-nicotinamide,
N-((1R,2R)-2-hydroxy-cyclohexyl)-6-[(2-methoxy-ethyl)-methyl-amino]-5-(4-trifluoromethyl-phenyl)-nicotinamide,
5-(4-chloro-phenyl)-6-([1,3]dioxolan-4-ylmethoxy)-N-((1R,2R)-2-hydroxy-cyclohexyl)-nicotinamide,
6-([1,3]dioxolan-4-ylmethoxy)-N-((1R,2R)-2-hydroxy-cyclohexyl)-5-(4-trifluoromethyl-phenyl)-nicotinamide,
6-cyclopropylmethoxy-5-(4-fluoro-phenyl)-N-((1R,2R)-2-hydroxy-cyclohexyl)-nicotinamide,
5-(4-chloro-phenyl)-N-((1R,2R)-2-hydroxy-cyclohexyl)-6-isobutoxy-nicotinamide,
5-(4-chloro-phenyl)-6-(2-ethoxy-ethoxy)-N-((1R,2R)-2-hydroxy-cyclohexyl)-nicotinamide,
5-(4-chloro-phenyl)-N-((1R,2R)-2-hydroxy-cyclohexyl)-6-(3-methyl-butoxy)-nicotinamide,
(−)-cis-5-(4-chloro-phenyl)-6-cyclopropylmethoxy-N-2-hydroxy-cyclohexylmethyl)-nicotinamide,
6-(4-carbamoyl-butoxy)-5-(4-chloro-phenyl)-N-((1R,2R)-2-hydroxy-cyclohexyl)-nicotinamide,
(−)-5-(4-chloro-phenyl)-6-cyclopropylmethoxy-N-(2-hydroxymethyl-butyl)-nicotinamide,
(RS)-5-(4-chloro-phenyl)-N-(2-hydroxymethyl-pentyl)-6-(2-methoxy-ethoxy)-nicotinamide,
6-cyclopropylmethoxy-N-((1R,2R)-2-hydroxy-cyclohexyl)-5-(4-trifluoromethyl-phenyl)-nicotinamide,
5-(4-chloro-phenyl)-N-((1R,2R)-2-hydroxy-cyclohexyl)-6-(oxetan-2-ylmethoxy)-nicotinamide,
5-(4-chloro-phenyl)-N-((1R,2R)-2-hydroxy-cyclohexyl)-6-(2,2,2-trifluoro-ethoxy)-nicotinamide,
5-(4-chloro-phenyl)-N-(2-cyclopropyl-2-hydroxy-propyl)-6-(2,2,2-trifluoro-ethoxy)-nicotinamide,
5-(4-fluoro-phenyl)-N-((R,2R)-2-hydroxy-cyclohexyl)-6-(2,2,2-trifluoro-ethoxy)-nicotinamide,
N-(2-cyclopropyl-2-hydroxy-propyl)-5-(4-fluoro-phenyl)-6-(2,2,2-trifluoro-ethoxy)-nicotinamide,
N-((1R,2R)-2-hydroxy-cyclohexyl)-6-(2,2,2-trifluoro-ethoxy)-5-(4-trifluoromethyl-phenyl)-nicotinamide,
N-(2-cyclopropyl-2-hydroxy-propyl)-6-(2,2,2-trifluoro-ethoxy)-5-(4-trifluoromethyl-phenyl)-nicotinamide,
N-((1R,2R)-2-hydroxy-cyclohexyl)-6-(2,2,2-trifluoro-ethoxy)-5-(4-trifluoromethoxy-phenyl)-nicotinamide,
5-(4-chloro-phenyl)-N-((1RS,2RS)-2-hydroxy-cyclohexylmethyl)-6-[(2-methoxy-ethyl)-methyl-amino]-nicotinamide,
(−)-cis-6-cyclopropylmethoxy-5-(4-fluoro-phenyl)-N-(2-hydroxy-cyclohexylmethyl)-nicotinamide,
(−)-cis-5-(4-chloro-phenyl)-N-(2-hydroxy-cyclohexylmethyl)-6-(2-methoxy-ethoxy)-nicotinamide,
(−)-6-cyclopropylmethoxy-5-(4-fluoro-phenyl)-N-(2-hydroxymethyl-butyl)-nicotinamide,
(−)-cis-5-(4-fluoro-phenyl)-N-(2-hydroxy-cyclohexylmethyl)-6-(2-methoxy-ethoxy)-nicotinamide, 5-(4-chloro-phenyl)-6-(cyclopropylmethyl-methyl-amino)-N-((1R,2R)-2-hydroxy-cyclohexyl)-nicotinamide,
5-(4-chloro-phenyl)-6-(cyclopropylmethyl-methyl-amino)-N-((1RS,2RS)-2-hydroxy-cyclohexylmethyl)-nicotinamide,
6-(cyclopropylmethyl-methyl-amino)-5-(4-fluoro-phenyl)-N-((1R,2R)-2-hydroxy-cyclohexyl)-nicotinamide,
6-(cyclopropylmethyl-methyl-amino)-5-(4-fluoro-phenyl)-N-((1RS,2RS)-2-hydroxy-cyclohexylmethyl)-nicotinamide,
5-(4-chloro-phenyl)-N-(2-cyclopropyl-2-hydroxy-propyl)-6-(3-methyl-isoxazol-5-ylmethoxy)-nicotinamide,
5-(4-chloro-phenyl)-N-((1R,2R)-2-hydroxy-cyclohexyl)-6-(3-methyl-isoxazol-5-ylmethoxy)-nicotinamide,
cis-5-(4-chloro-phenyl)-N-(2-hydroxy-cyclohexylmethyl)-6-(3-methyl-isoxazol-5-ylmethoxy)-nicotinamide,
5-(4-chloro-phenyl)-N-(2-hydroxymethyl-butyl)-6-(3-methyl-isoxazol-5-ylmethoxy)-nicotinamide,
N-((R)-2-cyclopropyl-2-hydroxy-propyl)-6-cyclopropylmethoxy-5-(4-trifluoromethyl-phenyl)-nicotinamide,
N-((S)-2-cyclopropyl-2-hydroxy-propyl)-6-cyclopropylmethoxy-5-(4-trifluoromethyl-phenyl)-nicotinamide,
6-cyclopropylmethoxy-N-((1RS,2RS)-2-hydroxy-cyclohexylmethyl)-5-(4-trifluoromethoxy-phenyl)-nicotinamide,
(RS)-N-(2-cyclopropyl-2-hydroxy-propyl)-6-cyclopropylmethoxy-5-(4-trifluoromethoxy-phenyl)-nicotinamide,
6-cyclopropylmethoxy-N-((1R,2R)-2-hydroxy-cyclohexyl)-5-(4-trifluoromethoxy-phenyl)-nicotinamide,
5-(4-chloro-phenyl)-N-((1R,2R)-2-hydroxy-cyclohexyl)-6-(methyl-propyl-amino)-nicotinamide,
5-(4-chloro-phenyl)-N-(2-cyclopropyl-2-hydroxy-propyl)-6-(pyridin-2-ylmethoxy)-nicotinamide,
(−)-cis-6-cyclopropylmethoxy-N-((2-hydroxy-cyclohexylmethyl)-5-(4-trifluoromethoxy-phenyl)-nicotinamide,
N-((R)-2-cyclopropyl-2-hydroxy-propyl)-6-(2-methoxy-ethoxy)-5-(4-trifluoromethyl-phenyl)-nicotinamide,
5-(4-fluoro-phenyl)-N-((1R,2R)-2-hydroxy-cyclohexyl)-6-(methyl-propyl-amino)-nicotinamide,
N-((R)-2-cyclopropyl-2-hydroxy-propyl)-5-(4-fluoro-phenyl)-6-(2-methoxy-ethoxy)-nicotinamide,
N-((R)-2-cyclopropyl-2-hydroxy-propyl)-6-cyclopropylmethoxy-5-(4-fluoro-phenyl)-nicotinamide,
3'-(4-chloro-phenyl)-3,4,5,6-tetrahydro-2H-[1,2']bipyridinyl-5'-carboxylic acid ((1R,2R)-2-hydroxy-cyclohexyl)-amide,
5-(4-chloro-phenyl)-N-((S)-2-cyclopropyl-2-hydroxy-propyl)-6-(3-methyl-isoxazol-5-ylmethoxy)-nicotinamide,
(−)-N-(2-cyclopropyl-2-hydroxy-propyl)-6-cyclopropylmethoxy-5-(4-trifluoromethoxy-phenyl)-nicotinamide,
5-(4-chloro-phenyl)-N-((1R,2R)-2-hydroxy-cyclohexyl)-6-(1-methyl-1H-imidazol-2-ylmethoxy)-nicotinamide,
6-cyclopropylmethoxy-N-((1RS,2RS)-2-hydroxy-cyclohexylmethyl)-5-(4-trifluoromethyl-phenyl)-nicotinamide,
5-(4-chloro-phenyl)-N-((1R,2R)-2-hydroxy-cyclohexyl)-6-(2-methyl-2H-[1,2,4]triazol-3-ylmethoxy)-nicotinamide,
cis-5-(4-chloro-phenyl)-N-(2-hydroxy-cyclohexylmethyl)-6-(2-methyl-2H-[1,2,4]triazol-3-ylmethoxy)-nicotinamide,
cis-5-(4-Chloro-phenyl)-N-(2-hydroxy-cyclohexylmethyl)-6-(1-methyl-1H-imidazol-2-ylmethoxy)-nicotinamide,
cis-5-(4-chloro-phenyl)-N-(2-hydroxy-cyclohexylmethyl)-6-(pyrimidin-2-ylmethoxy)-nicotinamide,
5-(4-chloro-phenyl)-N-(2-hydroxymethyl-butyl)-6-(pyrimidin-2-ylmethoxy)-nicotinamide,
(−)-cis-6-cyclopropylmethoxy-N-(2-hydroxy-cyclohexylmethyl)-5-(4-trifluoromethyl-phenyl)-nicotinamide,
5-(4-cyano-phenyl)-6-cyclopropylmethoxy-N-((1RS,2RS)-2-hydroxy-cyclohexylmethyl)-nicotinamide,
5-(4-chloro-phenyl)-N-((1R,2R)-2-hydroxy-cyclohexyl)-6-(pyrimidin-2-ylmethoxy)-nicotinamide,
5-(4-chloro-phenyl)-N-((1R,2R)-2-hydroxy-cyclohexyl)-6-(pyridin-4-ylmethoxy)-nicotinamide,
cis-5-(4-chloro-phenyl)-N-(2-hydroxy-cyclohexylmethyl)-6-(pyridin-4-ylmethoxy)-nicotinamide,
5-(4-chloro-phenyl)-N-(2-hydroxymethyl-butyl)-6-(pyridin-4-ylmethoxy)-nicotinamide,
(RS)-5-(4-cyano-phenyl)-6-cyclopropylmethoxy-N-(2-hydroxymethyl-butyl)-nicotinamide,
5-(4-chloro-phenyl)-N-((R)-2-cyclopropyl-2-hydroxy-propyl)-6-cyclopropylmethoxy-nicotinamide,
5-(4-chloro-phenyl)-N-((R)-2-cyclopropyl-2-hydroxy-propyl)-6-(3-methyl-isoxazol-5-ylmethoxy)-nicotinamide,
(RS)-6-cyclopropylmethoxy-N-(2-hydroxymethyl-butyl)-5-(4-trifluoromethoxy-phenyl)-nicotinamide,
(RS)-6-cyclopropylmethoxy-N-(2-hydroxymethyl-butyl)-5-(4-trifluoromethyl-phenyl)-nicotinamide,
(−)-6-cyclopropylmethoxy-N-(2-hydroxymethyl-butyl)-5-(4-trifluoromethyl-phenyl)-nicotinamide,
(−)-cis-5-(4-Cyano-phenyl)-6-cyclopropylmethoxy-N-(2-hydroxy-cyclohexylmethyl)-nicotinamide,
(+)-cis-5-(4-cyano-phenyl)-6-cyclopropylmethoxy-N-(2-hydroxy-cyclohexylmethyl)-nicotinamide,
(−)-5-(4-cyano-phenyl)-6-cyclopropylmethoxy-N-((2-hydroxymethyl-butyl)-nicotinamide,
(+)-5-(4-cyano-phenyl)-6-cyclopropylmethoxy-N-((2-hydroxymethyl-butyl)-nicotinamide,
(+)-5-(4-cyano-phenyl)-N-(2-cyclopropyl-2-hydroxy-propyl)-6-cyclopropylmethoxy-nicotinamide,
6-cyclopropylmethoxy-5-(4-fluoro-phenyl)-N-(2-hydroxy-2-methyl-propyl)-nicotinamide,
(−)-6-cyclopropylmethoxy-N-(2-hydroxymethyl-butyl)-5-(4-trifluoromethoxy-phenyl)-nicotinamide,
6-cyclopropylmethoxy-5-(4-fluoro-phenyl)-N-(1-hydroxy-cyclopentylmethyl)-nicotinamide,
5-(4-chloro-phenyl)-N-((1R,2R)-2-hydroxy-cyclohexyl)-6-(pyridin-3-ylmethoxy)-nicotinamide,
5-(4-fluoro-phenyl)-N-((1R,2R)-2-hydroxy-cyclohexyl)-6-(pyridin-3-ylmethoxy)-nicotinamide,
5-(4-chloro-phenyl)-N-((R)-2-cyclopropyl-2-hydroxy-propyl)-6-(pyridin-3-ylmethoxy)-nicotinamide,
N-((R)-2-cyclopropyl-2-hydroxy-propyl)-5-(4-fluoro-phenyl)-6-(pyridin-3-ylmethoxy)-nicotinamide,
5-(4-chloro-phenyl)-N-((R)-2-cyclopropyl-2-hydroxy-propyl)-6-(3-methyl-pyridin-2-ylmethoxy)-nicotinamide,
N-((R)-2-cyclopropyl-2-hydroxy-propyl)-5-(4-fluoro-phenyl)-6-(3-methyl-pyridin-2-ylmethoxy)-nicotinamide,
5-(4-chloro-phenyl)-N-((1R,2R)-2-hydroxy-cyclohexyl)-6-[methyl-(4-methyl-thiazol-2-ylmethyl)-amino]-nicotinamide,
(RS)-N-(2-cyclobutyl-2-hydroxy-propyl)-6-cyclopropylmethoxy-5-(4-fluoro-phenyl)-nicotinamide,
5-(4-chloro-phenyl)-N-((1R,2R)-2-hydroxy-cyclohexyl)-6-(5-methyl-isoxazol-3-ylmethoxy)-nicotinamide,
5-(4-fluoro-phenyl)-N-((1R,2R)-2-hydroxy-cyclohexyl)-6-(5-methyl-isoxazol-3-ylmethoxy)-nicotinamide,
5-(4-chloro-phenyl)-N-((R)-2-cyclopropyl-2-hydroxy-propyl)-6-(5-methyl-isoxazol-3-ylmethoxy)-nicotinamide,
N-((R)-2-cyclopropyl-2-hydroxy-propyl)-5-(4-fluoro-phenyl)-6-(5-methyl-isoxazol-3-ylmethoxy)-nicotinamide, N-((R)-2-cyclopropyl-2-hydroxy-propyl)-5-(4-fluoro-phenyl)-6-(pyridin-2-ylmethoxy)-nicotinamide, (RS)-6-cyclopropylmethoxy-5-(4-fluoro-phenyl)-N-(3,3,3-trifluoro-2-hydroxy-2-methyl-propyl)-nicotinamide, (RS)-6-cyclopropylmethoxy-N-(3,3,3-trifluoro-2-hydroxy-2-methyl-propyl)-5-(4-trifluoromethyl-phenyl)-nicotinamide, (RS)-6-cyclopropylmethoxy-N-(3,3,3-trifluoro-2-hydroxy-2-methyl-propyl)-5-(4-trifluoromethoxy-phenyl)-nicotinamide, 5-(4-chloro-phenyl)-N-((1R,2R)-2-hydroxy-cyclohexyl)-6-(3-methyl-pyridin-2-ylmethoxy)-nicotinamide, 5-(4-fluoro-phenyl)-N-((1R,2R)-2-hydroxy-cyclohexyl)-6-(3-methyl-pyridin-2-ylmethoxy)-nicotinamide 5-(4-chloro-phenyl)-N-((1R,2R)-2-hydroxy-cyclohexyl)-6-(pyridin-2-ylmethoxy)-nicotinamide, 5-(4-chloro-phenyl)-N-((R)-2-cyclopropyl-2-hydroxy-propyl)-6-(pyridin-2-ylmethoxy)-nicotinamide, 5-(4-fluoro-phenyl)-N-((1R,2R)-2-hydroxy-cyclohexyl)-6-(pyridin-2-ylmethoxy)-nicotinamide, 5-(4-fluoro-phenyl)-N-((1R,2R)-2-hydroxy-cyclohexyl)-6-(pyridin-4-ylmethoxy)-nicotinamide, N-((R)-2-cyclopropyl-2-hydroxy-propyl)-5-(4-fluoro-phenyl)-6-(pyridin-4-ylmethoxy)-nicotinamide, 5-(4-chloro-phenyl)-N-((R)-2-cyclopropyl-2-hydroxy-propyl)-6-(pyridin-4-ylmethoxy)-nicotinamide, 5-(4-cyano-phenyl)-6-cyclopropylmethoxy-N-((1R,2R)-2-hydroxy-cyclohexyl)-nicotinamide, and all pharmaceutically acceptable salts thereof.

A group of preferred compounds are the following:

5-(2-chloro-5-trifluoromethyl-phenyl)-6-cyclopentyloxy-N-((1R,2R)-2-hydroxy-cyclohexyl)-nicotinamide, 6-butoxy-5-(2-fluoro-5-trifluoromethyl-phenyl)-N-((1R,2R)-2-hydroxy-cyclohexyl)-nicotinamide, 6-butoxy-5-(4-chloro-phenyl)-N-((1R,2R)-2-hydroxy-cyclohexyl)-nicotinamide, 6-butoxy-5-(4-chloro-phenyl)-N-(2-cyclopropyl-2-hydroxy-propyl)-nicotinamide, 5-(4-chloro-phenyl)-6-cyclopropylmethoxy-N-((1R,2R)-2-hydroxy-cyclohexyl)-nicotinamide, 5-(4-chloro-phenyl)-N-(2-cyclopropyl-2-hydroxy-propyl)-6-cyclopropylmethoxy-nicotinamide, 6-cyclopropylmethoxy-5-(2-fluoro-5-trifluoromethyl-phenyl)-N-((1R,2R)-2-hydroxy-cyclohexyl)-nicotinamide, 6-butoxy-5-(2-chloro-5-trifluoromethyl-phenyl)-N-((1R,2R)-2-hydroxy-cyclohexyl)-nicotinamide, 5-(2-chloro-5-trifluoromethyl-phenyl)-6-cyclopropylmethoxy-N-((1R,2R)-2-hydroxy-cyclohexyl)-nicotinamide, and all pharmaceutically acceptable salts thereof.

Especially preferred are the compounds selected from the group consisting of:

5-(4-chloro-phenyl)-6-cyclopropylmethoxy-N-((1R,2R)-2-hydroxy-cyclohexyl)-nicotinamide, 5-(4-chloro-phenyl)-N-((1R,2R)-2-hydroxy-cyclohexyl)-6-(2-methoxy-ethoxy)-nicotinamide, N-((1R,2R)-2-hydroxy-cyclohexyl)-6-(2-methoxy-ethoxy)-5-(4-trifluoromethyl-phenyl)-nicotinamide, 6-cyclopropylmethoxy-5-(4-fluoro-phenyl)-N-((1R,2R)-2-hydroxy-cyclohexyl)-nicotinamide, N-((R)-2-cyclopropyl-2-hydroxy-propyl)-6-cyclopropylmethoxy-5-(4-fluoro-phenyl)-nicotinamide, 5-(4-chloro-phenyl)-N-((1R,2R)-2-hydroxy-cyclohexyl)-6-(pyrimidin-2-ylmethoxy)-nicotinamide, and all pharmaceutically acceptable salts thereof.

The present invention also relates to a process for the manufacture of compounds of formula I as defined above, which process comprises coupling a compound of formula

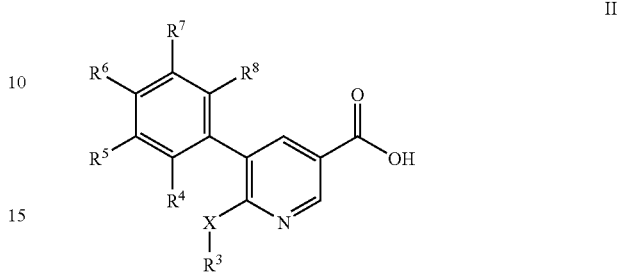

II wherein X and $R^3$ to $R^8$ are as defined herein before, with an amine of the formula

H—NR$^1$R$^2$    III wherein $R^1$ and $R^2$ are as defined herein before, with the help of an coupling agent under basic conditions, and, if desired, converting the resulting compound of formula I into a pharmaceutically acceptable salt thereof.

Coupling agents for the reaction of compounds of formula II with amines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). Preferred coupling agent is TBTU. Suitable bases include triethylamine, diisopropylethylamine and, preferably, Hünig's base.

Alternatively, the present invention also relates to a process for the manufacture of compounds of formula I as defined above, which process comprises coupling a compound of formula

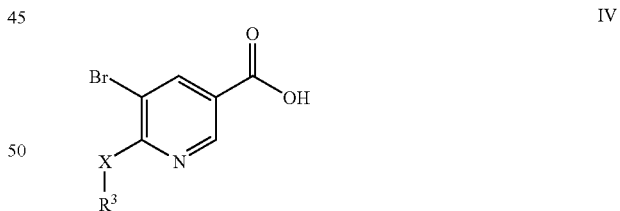

IV wherein X and $R^3$ are as defined herein before, with an aryl metal species of the formula

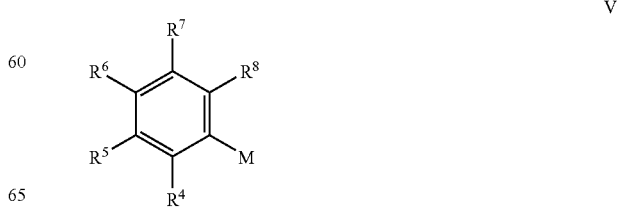

V wherein $R^4$ to $R^8$ are as defined herein before and M means boronic acid or a boronic acid ester, in the presence of a Pd catalyst under basic conditions, and, if desired, converting the resulting compound of formula I into a pharmaceutically acceptable salt thereof.

The aryl metal species is preferably an aryl boronic acid or arylboronic acid ester. The palladium catalyst is preferably a palladium(II)chloride-dppf complex which is used in the presence of a base, preferably sodium carbonate.

Thus, the compounds of formula I can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The synthesis of compounds with the general structure I, can be accomplished according to the following schemes 1 to 4.

Following the procedure according to scheme 1, compound AA (5-bromo-6-chloro-3-pyridinecarboxylic acid methyl ester, CAS RN 78686-77-8) can be used as starting material. AA is commercially available or can alternatively be prepared by a three step sequence from 6-hydroxy-3-pyridinecarboxylic acid following literature procedures by bromination with bromine in acetic acid, preparation of the 5-bromo-6-chloro-3-pyridine carboxylic acid chloride with phosphorus oxychloride and/or phosphorus pentachloride and solvolysis with methanol.

Compound AC can be prepared from AA by reaction with a suitably substituted primary or secondary alcohol of formula AB or a phenol of formula AB in the presence of a base, for example sodium hydride, in an inert solvent, for example dimethylformamide, at temperatures from room temperature to reflux temperature of the solvent, preferably at room temperature.

Compound AE can be prepared by coupling a suitably substituted aryl metal species of formula AD, preferably an arylboronic acid or arylboronic acid ester, with AC in the presence of a suitable catalyst, preferably a palladium catalyst and more preferably alladium(II)acetate/triphenylphosphine mixtures or palladium(II)chloride-dppf (1,1'-bis (diphenylphosphino)ferrocene) complexes and a base, preferably triethylamine or sodium carbonate in an inert solvent such as dimethylformamide or toluene.

Compound AF can then be obtained by saponification of compound AC by methods known in the art, for example by saponification with an alkalimetal hydroxide, for example sodium hydroxide, in a suitable solvent, for example a mixture of dioxane and water.

In the following step compounds of formula I are obtained from compound AF and the corresponding amine of formula III by suitable amide bond forming reactions. These reactions are known in the art. For example coupling reagents like N,N'-carbonyl-diimidazole (CDI), N,N'-dicyclohexyl-carbodiimide (DCC), 1-(3-dimethylaminopropyl)-3-ethyl-carbodiimide hydrochloride (EDCI), 1-[bis(dimethylamino) methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature.

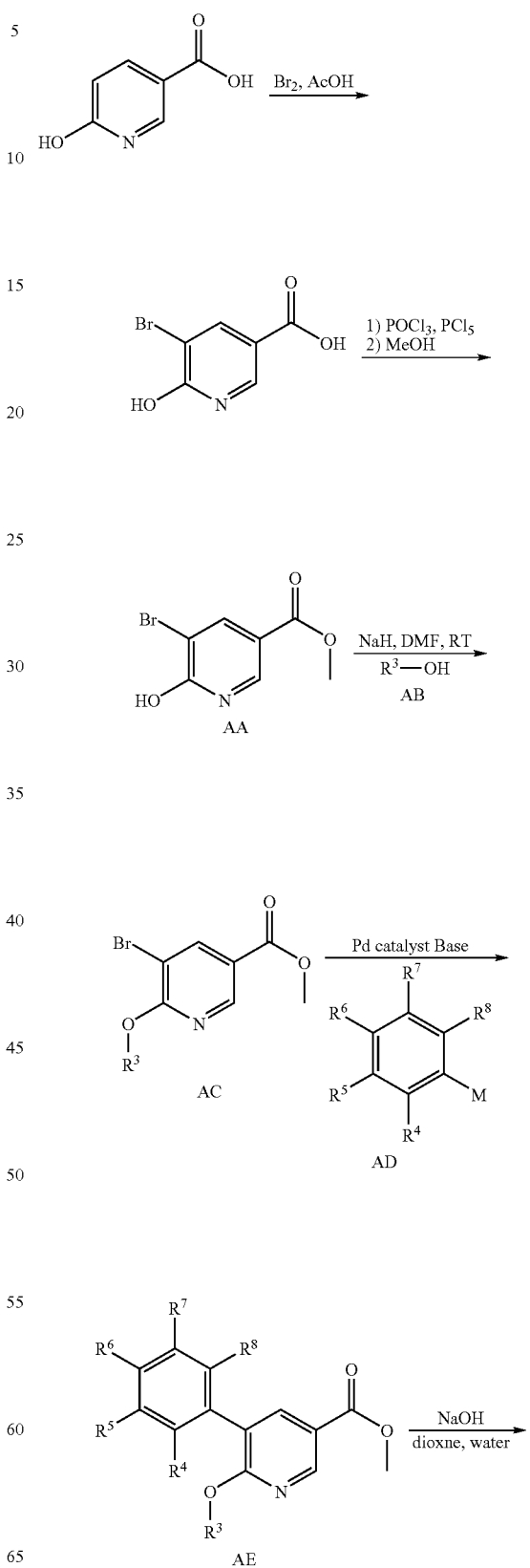

-continued

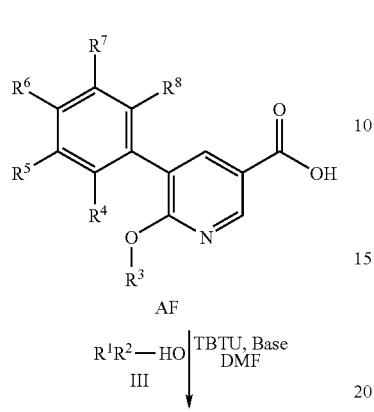

AF

| TBTU, Base
R¹R²—HO | DMF
III

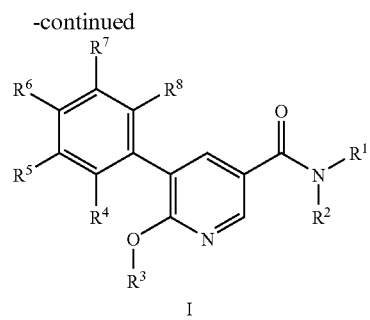

I

Alternatively, compounds of formula I can be prepared according to scheme 2 starting from compound BA (5-bromo-6-chloro-3-picoline, CAS RN 17282-03-0), which is commercially available or can be prepared starting from 6-hydroxy-3-picoline following literature procedures by bromination with N-bromosuccinimide (NBS) and reaction with phosphorus oxychloride.

Scheme 2

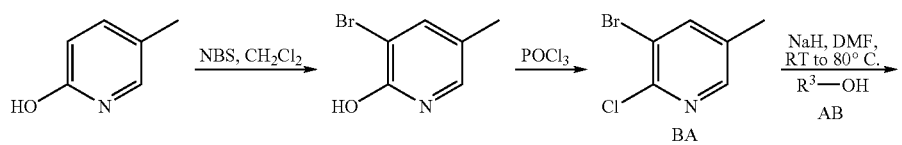

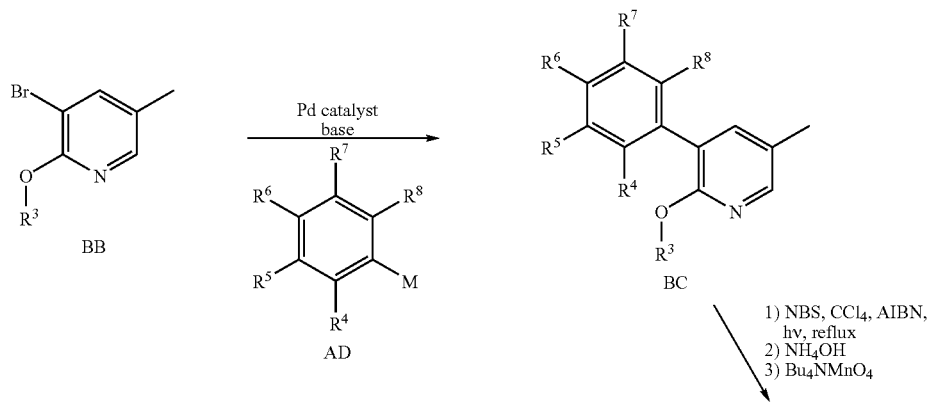

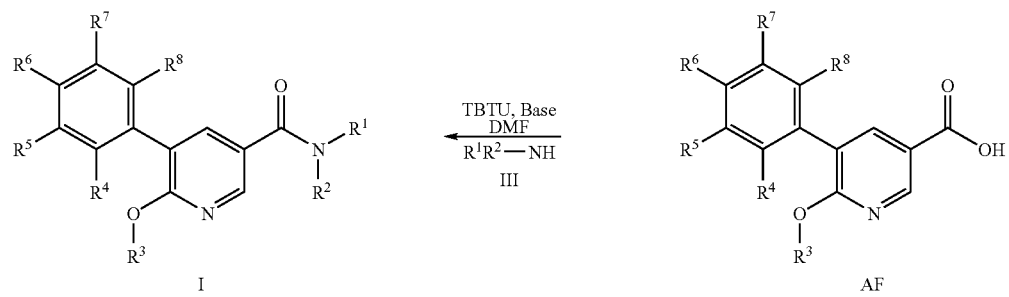

Compound BB is prepared from BA by reaction with a suitably substituted primary or secondary alcohol of formula AB or a phenol of formula AB in the presence of a base, for example sodium hydride, in an inert solvent, for example dimethylformamide, at temperatures from room temperature to reflux temperature of the solvent, preferably at 70° C.

Compound BC can then be prepared by coupling a suitably substituted aryl metal species, preferably an arylboronic acid or arylboronic acid ester of formula AD, with BB in the presence of a suitable catalyst, preferably a palladium catalyst and more preferably palladium(II)chloride-dppf complexes and a base, preferably sodium carbonate in an inert solvent such as toluene.

Starting from BC compound AD can be obtained by direct or multistep oxidation of the methyl group by methods known in the art as for example those reviewed in March, Advanced Organic Chemistry, 5th ed. 2001, Wiley & Sons. More specifically compound BC can be brominated with N-bromosuccinimide (NBS) in the presence of a radical chain initiator as for example azo-bisisobutyronitrile (AIBN) in an inert solvent, for example carbon tetrachloride, by irradiating and heating, saponification of the produced mono- or dibromide with for example ammonium hydroxide to the aldehyde or alcohol and finally by oxidation with a suitable oxidizing agent, for example tetrabutylammonium permanganate, in an inert solvent such as pyridine.

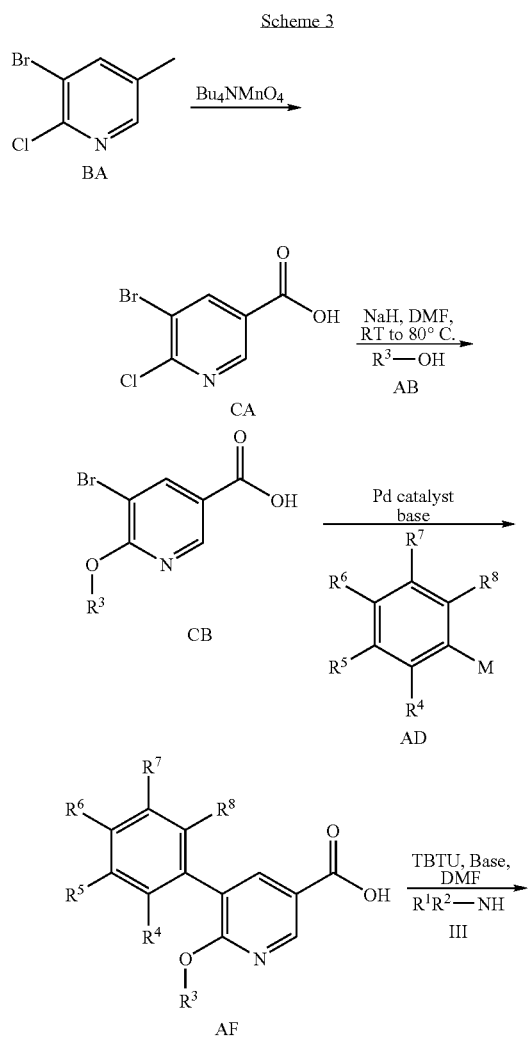

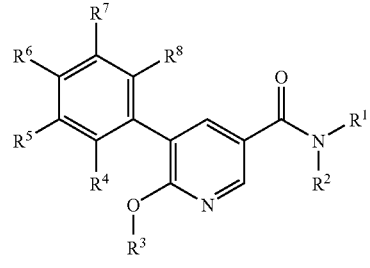

Alternatively, compounds of formula I can be prepared according to scheme 3 starting from compound CA (5-bromo-6-chloro-3-pyridinecarboxylic acid, CAS RN 29241-62-1) which is commercially available or can be obtained by literature methods or by oxidation of compound BA with tetrabutylammonium permanganate in pyridine.

Compound CB is obtained from compound CA by reaction with a suitably substituted primary or secondary alcohol of formula AB or a phenol of formula AB in the presence of two or more equivalents of a base, for example sodium hydride, in an inert solvent, for example dimethylformamide, at temperatures from room temperature to reflux temperature of the solvent, preferably at 70° C.

Compound AF can then be prepared by coupling a suitably substituted aryl metal species, preferably an arylboronic acid or arylboronic acid ester of formula AD, with CB in the presence of a suitable catalyst, preferably a palladium catalyst and more preferably palladium(II)chloride-dppf complexes, and a base, preferably sodium carbonate in an inert solvent such as toluene.

Alternatively, compounds of formula I can be prepared starting from compound CA by protecting the acid group with a suitable protecting group (P) to give compound DA by methods known in the art (Scheme 4). Suitable acid protecting groups are for example benzyl (Bn), benzyloxymethyl (BOM), methoxyethoxymethyl (MEM) or allyl groups and silyl groups such as trimethylsilyl, triethylsilyl and tert-butyldimethylsilyl esters (for more details see T. W. Greene et al., Protective Groups in Organic Chemistry, John Wiley and Sons Inc. New York 1999, 3$^{rd}$ edition).

Compound DB can be prepared from DA by reaction with a suitably substituted primary or secondary alcohol of formula AB or a phenol of formula AB in the presence of a base, for example sodium hydride, in an inert solvent, for example dimethylformamide, at temperatures from room temperature to reflux temperature of the solvent, preferably at room temperature.

By coupling a suitably substituted aryl metal species, preferably an arylboronic acid or arylboronic acid ester of formula AD, with DB in the presence of a suitable catalyst, preferably a palladium catalyst and more preferably palladium(II)chloride-dppf complexes, and a base, preferably sodium carbonate in an inert solvent such as toluene, a compound DC is obtained. Compound AF can in turn be prepared by de-protection of compound DC by methods known in the art.

Scheme 4

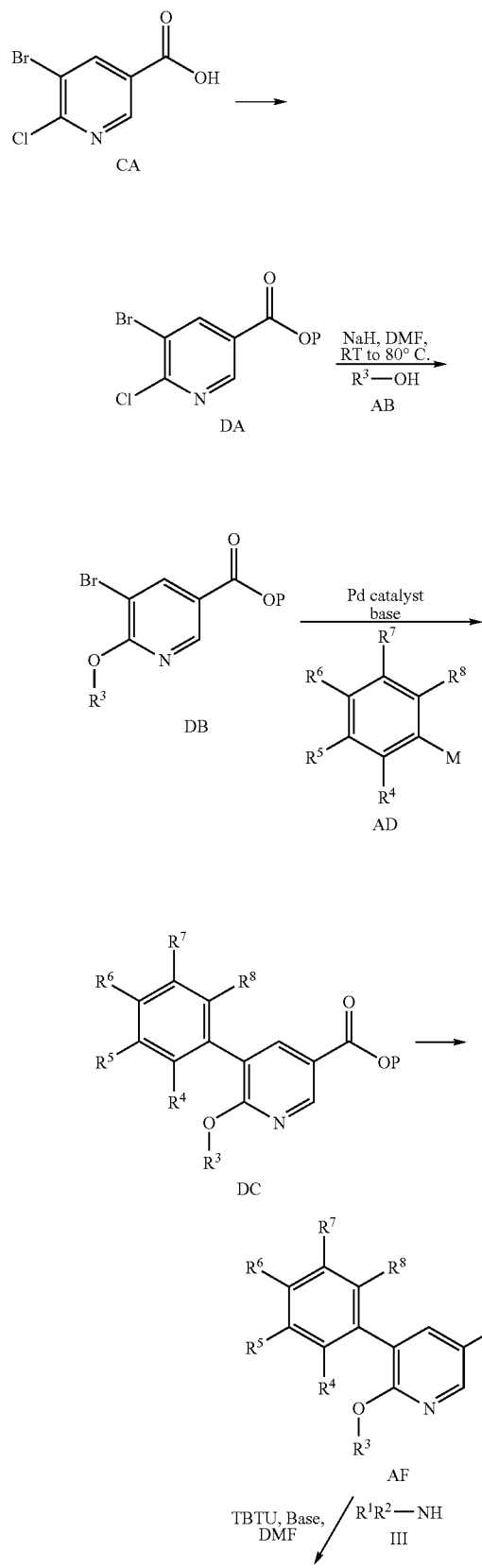

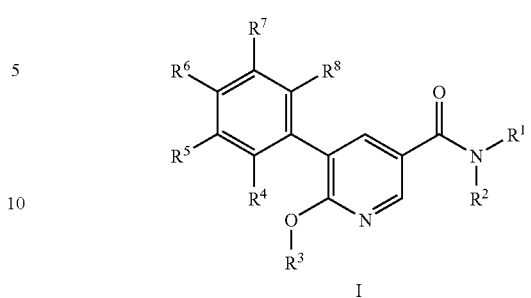

Alternatively, compounds of formula I can be prepared according to scheme 5 starting from compound EA by direct alkylation with an alkylating agent EB to give an intermediate EC. Advantageously such an alkylation can be achieved in the presence of a base, for example potassium hydroxide in an inert solvent, for example dimethylsulfoxide, at elevated temperatures in a microwave apparatus.

Compound AF can be prepared from EC by coupling a suitably substituted aryl metal species, preferably an arylboronic acid or arylboronic acid ester of formula AD, with EC in the presence of a suitable catalyst, preferably a palladium catalyst and more preferably palladium(II)chloride-dppf complexes, and a base, preferably sodium carbonate in an inert solvent such as toluene.

Scheme 5

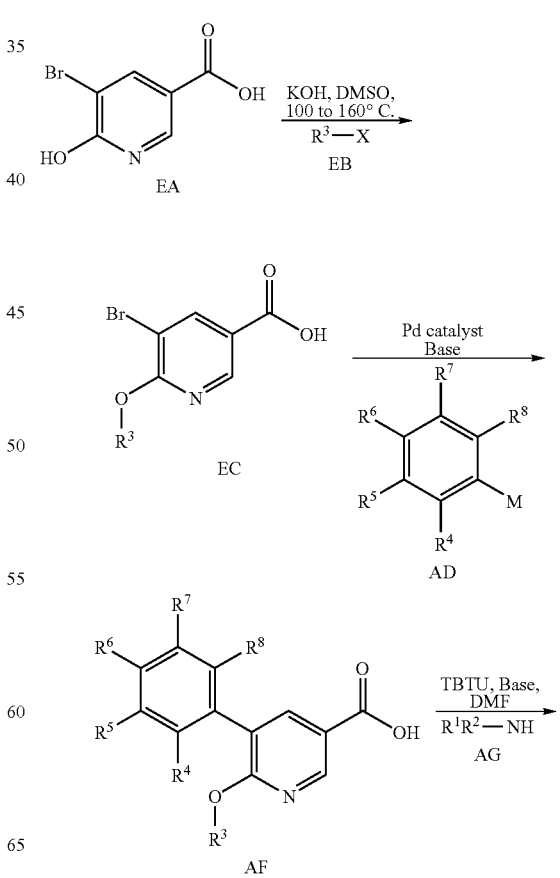

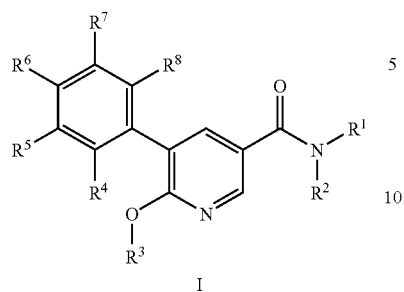

I

Alternatively, compounds of formula I can be prepared according to scheme 6 starting from compound EC by first reacting with an amine of formula AG using suitable amide bond forming reactions to deliver a compound of formula FA. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature.

Compounds of formula I can be prepared from FA by coupling a suitably substituted aryl metal species, preferably an arylboronic acid or arylboronic acid ester of formula AD, with FA in the presence of a suitable catalyst, preferably a palladium catalyst and more preferably palladium(II)chloride-dppf complexes, and a base, preferably sodium carbonate in an inert solvent such as toluene.

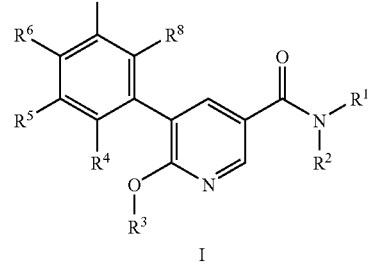

I

Alternatively, compounds of formula I can be prepared according to scheme 7 starting from compound GA by Mitsunobu-type alkylation using an alcohol of formula AB as alkylating agent in the presence of a dehydrating agent, for example using triphenylphosphine and azodicarboxylates as dehydrating and activating agents to give an intermediate GB.

Compounds of formula AE can be prepared from GB by coupling a suitably substituted aryl metal species, preferably an arylboronic acid or arylboronic acid ester of formula AD, with FA in the presence of a suitable catalyst, preferably a palladium catalyst and more preferably palladium(II)chloride-dppf complexes, and a base, preferably sodium carbonate in an inert solvent such as toluene.

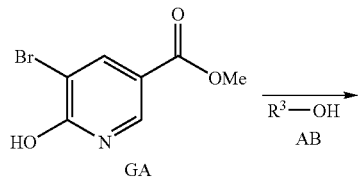

The invention further relates to compounds of formula I as defined above, when manufactured according to a process as defined above.

Some compounds of formula I may possess asymmetric centers and are therefore capable of existing in more than one stereoisomeric form. The invention thus also relates to compounds in substantially pure isomeric form at one or more asymmetric centers as well as mixtures, including racemic mixtures, thereof. Such isomers may be prepared by asymmetric synthesis, for example using chiral intermediates, or mixtures may be resolved by conventional methods, e.g., chromatography (chromatography with a chiral adsorbens or eluent), or use of a solving agent.

It will be appreciated, that the compounds of general formula I in this invention may be derivatized at functional groups to provide derivatives which are capable of conversion back to the parent compound in vivo.

As described above, the compounds of formula I or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety, psychosis, schizophrenia, depression, abuse of psychotropes, for example for the abuse and/or dependence of a substances, including alcohol dependency and nicotine dependency, neuropathies, multiple sclerosis, migraine, stress, epilepsy, dyskinesias, Parkinson's disease, amnesia, cognitive disorders, memory deficits, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred embodiment to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

It is a further preferred embodiment to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of a lipase inhibitor, particularly, wherein the lipase inhibitor is orlistat. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of an anti-diabetic agent selected from the group consisting of 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331, and the like 5) DPP-IV-inhibitors such as LAF-237 (Vildagliptin) or MK-0431, and the like; 6) Glucokinase activators such as the compounds disclosed in e.g. WO 00/58293 A1, and the like. Also an embodiment of the invention is the method as described above for the simultaneous, separate or sequential administration of a compound according to formula I and a therapeutically effective amount of an anti-diabetic agent as 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331 GW-2331 and the like; 5) DPP-IV-inhibitors such as LAF-237 (Vildagliptin) or MK-0431, and the like; 6) Glucokinase activators such as the compounds disclosed in e.g. WO 00/58293 A1, and the like.

It is a further preferred embodiment to provide a method of treatment or prevention of dyslipidemias in a human which comprises administration of a therapeutically effective amount of a compound according to formula I in combination or association with a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists. Also an embodiment of the invention is the method as described above for the simultaneous, separate or sequential administration of a compound according to formula I and a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149–153, 1990; Morris, J. Neurosci. Methods 11:47–60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442–448, 2002; Campbell et al., Exp. Clin. Psychopharmacol. 8:312–25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula I.

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glassfiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561–564 (CB1) and Nature 1993, 365, 61–65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonized by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605–613. The compounds of the present invention or their pharmaceutically acceptable salts are antagonists and selective for the CB1 receptor with affinities below $IC_{50}=0.5$ μM, preferably below 200 nM, more preferably 1 nM to 100 nM. They exhibit at least a 10 fold selectivity against the CB2 receptor.

| Compound of Example | $IC_{50}$ [μM] |
|---|---|
| 2 | 0.186 |
| 3 | 0.039 |
| 7 | 0.102 |

Effect of CB1 Receptor Antagonist/Inverse Agonist on CP 55,940-Induced Hypothermia in NMRI Mice Animals Male NMRI mice were used in this study and were obtained from Research Consulting Company Ltd (RCC) of Füllinsdorf (Switzerland). Mice, weighing 30–31 g were used in this study. Ambient temperature is approximately 20–21° C. and relative humidity 55–65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behavior by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula I to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula I in diseases or disorders may be demonstrated in animal disease models that have been reported in the literature. The following are examples of such animal disease models: a) reduction of sweet food intake in marmosets (Behavioural Pharm. 1998, 9,179–181); b) reduction of sucrose and ethanol intake in mice (Psychopharm. 1997, 132, 104–106); c) increased motor activity and place conditioning in rats (Psychopharm. 1998, 135, 324–332; Psychopharmacol 2000, 151: 25–30); d) spontaneous locomotor activity in mice (J. Pharm. Exp. Ther. 1996, 277, 586–594); e) reduction in opiate self-administration in mice (Sci. 1999, 283, 401–404).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following examples serve to illustrate the present invention in more detail. They are, however, not intended to limit its scope in any manner.

EXAMPLES

MS=mass spectrometry; EI=electron impact; ISP=ion spray, corresponds to ESI (electrospray); NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; TBTU=O-(Benzotriazol-1-yl)-N,N',N'-tetramethyl-uronium-tetrafluoroborate; DMF=dimethylformamide, dppf=1,1'-bis(diphenylphosphino)ferrocene, DIPEA=diisopropylethylamine.

Example 1

5-(2-Chloro-5-trifluoromethyl-phenyl)-6-cyclopentyloxy-N-((1R,2R)-2-hydroxy-cyclohexyl)-nicotinamide 5-Bromo-1,6-dihydro-6-oxo-3-pyridinecarboxylic acid To a suspension of 1,6-dihydro-6-oxo-pyridinecarboxylic acid (40 g, 288 mmol) in acetic acid (75 mL) bromine (69 g, 431 mmol) is added dropwise with stirring. The temperature increased to 45° C. and the mixture was stirred overnight at 50° C. The reaction mixture was concentrated in vacuo and the crude residue of 5-bromo-1,6-dihydro-6-oxo-3-pyridinecarboxylic acid was used in the next step without purification.

5-Bromo-6-chloro-3-pyridinecarboxylic acid methyl ester

To 63 g of the previous crude material was added with mechanical stirring phosphorus oxychloride (75 mL) and then phosphorus pentachloride (120 g) in portions so that the temperature did not rise above 30° C. The mixture was stirred overnight at 95° C. and concentrated in vacuo. The residue was dissolved in dichloromethane (150 mL) and methanol (150 mL) was added dropwise. The mixture was boiled for 2 h and the solvents were removed in vacuo. The residue was partitioned between diethyl ether and sodium bicarbonate solution. Organic phases were pooled, dried with $MgSO_4$ and the solvent was evaporated. The residue was purified by column chromatography on silica (n-heptane/ethyl acetate 6:1) to yield 4 g of the title compound as a colorless solid, mp 78–79° C.

5-Bromo-6-cyclopentyloxy-3-pyridinecarboxylic acid methyl ester

Cyclopentanol (1 mL, 11 mmol) was dissolved in DMF (25 mL) and a dispersion of sodium hydride in oil (55–65%, 480 mg) was added at room temperature. The mixture was stirred for 1 h at room temperature and 5-bromo-6-chloro-3-pyridinecarboxylic acid methyl ester (2.5 g, 10 mmol) was added. Stirring was continued for 1 h at room temperature and the mixture was afterwards partitioned between water and diethyl ether. Organic phases were pooled, dried with $MgSO_4$ and the solvent was evaporated. The residue was purified by column chromatography on silica (n-heptane/ethyl acetate 9:1) to yield 0.48 g of the title compound as a colorless oil, MS (EI) 299.0, 301.0 (M)$^+$.

5-(2-Chloro-5-trifluoromethyl-phenyl)-6-cyclopentyloxy-3-pyridinecarboxylic acid methyl ester 5-Bromo-6-cyclopentyloxy-3-pyridinecarboxylic acid methyl ester (0.33 g, 1.1 mmol) was dissolved in DMF (3.5 mL). To this solution was added [2-chloro-5-(trifluoromethyl)phenyl]-boronic acid (370 mg, 1.6 mmol), palladium (II)acetate (7 mg), triphenylphosphine (18 mg) and triethylamine (0.46 mL). The whole mixture was heated with stirring at 100° C. for 20 h, cooled to room temperature and partitioned between dichloromethane and a mixture of water and concentrated ammonium hydroxide solution (water/ammonia 4:1 v/v). Organic phases were pooled, dried with $MgSO_4$ and the solvent was evaporated. The residue was purified by column chromatography on silica (n-heptane/ethyl acetate 6:1) to yield 0.27 g of the title compound as a light yellow oil, MS (ISP) 400.4 (M+H)$^+$.

5-(2-Chloro-5-trifluoromethyl-phenyl)-6-cyclopentyloxy-3-pyridinecarboxylic acid 5-(2-Chloro-5-trifluoromethyl-phenyl)-6-cyclopentyloxy-3-pyridinecarboxylic acid methyl ester (0.27 g, 0.7 mmol) was dissolved in dioxane (6 mL). Water (6 mL) and sodium hydroxide solution (2 mL, 2N) was added and the mixture was boiled with stirring for 2.5 h, cooled to room temperature and partitioned between diethyl ether and hydrochloric acid (1N). Organic phases were pooled, dried with $Na_2SO_4$ and the solvent was evaporated. The residue, 0.27 g of the title compound as a orange-yellow solid was introduced into the next step without purification, MS (ISP) 386.5 (M+H)$^+$.

5-(2-Chloro-5-trifluoromethyl-phenyl)-6-cyclopentyloxy-N-((1R,2R)-2-hydroxy-cyclohexyl)-nicotinamide 5-(2-Chloro-5-trifluoromethyl-phenyl)-6-cyclopentyloxy-3-pyridinecarboxylic acid (0.14 g, 0.3 mmol) was dissolved in DMF (5 mL). To the solution was added TBTU (0.12 g, 0.4 mmol), N,N-diisopropylethyl amine (0.3 mL, 1.7 mmol) and (1R,2R)-2-amino-cyclohexanol (58 mg, 0.4 mmol). The reaction mixture was stirred for 18 h at room temperature. The solvent was evaporated in vacuo and the residue was purified by column chromatography on silica (n-heptane/ethyl acetate gradient) to yield 0.11 g of the title compound as a colorless solid oil, MS (ISP) 483.4 (M+H)$^+$.

Example 2

6-Butoxy-5-(2-fluoro-5-trifluoromethyl-phenyl)-N-((1R,2R)-2-hydroxy-cyclohexyl)-nicotinamide

3-Bromo-5-methyl-2(1H)-pyridinone

5-Methyl-2(1H)-pyridinone (50 g, 0.46 mol) was suspended in dichloromethane (500 mL). N-bromosuccinimide (82 g, 0.46 mol) was added in portions with cooling. Addition was finished after 15 min; the mixture was stirred for 1 h at room temperature and afterwards partitioned between dichloromethane and water. Organic phases were pooled, dried with $Na_2SO_4$ and the solvent was evaporated. The residue was purified by crystallization from ethyl acetate to yield 55 g of the title compound as a light yellow solid, mp 156–161° C.

3-Bromo-2-chloro-5-methyl-pyridine

A mixture of 3-bromo-5-methyl-2(1H)-pyridinone (25 g, 0.13 mol) and phosphorus oxychloride (500 mL) was boiled with stirring for 20 h. Phosphorus oxychloride was removed by distillation and the residue was poured onto ice/water (800 mL). The mixture was adjusted to pH 8.5 with 2 N sodium hydroxide solution and extracted with diethyl ether. Organic phases were pooled, dried with $Na_2SO_4$ and the solvent was evaporated. The residue, 23.4 g of the title compound as a greyish solid was introduced into the next step without purification, MS (EI) 204.9, 206.9 $(M)^+$.

3-Bromo-2-butoxy-5-methyl-pyridine

Sodium hydride dispersion in oil (55–65%, 1.16 g) was added in portions to a well stirred solution of 1-butanol (2.4 mL, 27 mmol) in DMF (50 mL). After stirring the mixture for 1 h at room temperature 3-bromo-2-chloro-5-methyl-pyridine (5.0 g, 24 mmol) was added and stirring continued for 18 h at room temperature and for 4 h at 70° C. The cooled mixture was poured into saturated sodium bicarbonate solution and extracted with diethyl ether. Organic phases were pooled, dried with $Na_2SO_4$ and the solvent was evaporated. The residue was purified by column chromatography on silica (n-heptane/ethyl acetate 8:1) to yield 4.2 g of the title compound as a light red oil, MS (EI) 243.1, 245.1 $(M)^+$.

2-Butoxy-3-(2-fluoro-5-trifluoromethyl-phenyl)-5-methyl-pyridine

3-Bromo-2-butoxy-5-methyl-pyridine (0.96 g, 3.9 mmol) was dissolved in toluene (6 mL). To this solution was added [2-fluoro-5-(trifluoromethyl)phenyl]-boronic acid (1.2 g, 5.9 mmol), [1,1'-bis(diphenylphosphino)ferrocene]dichloropalladium(II) dichloro-methane complex (161 mg), and 2 N sodium carbonate solution (5.9 mL). The whole mixture was heated with stirring at 90° C. for 18 h, cooled to room temperature and eluted with ethyl acetate over 10 g ChemElut (Varian). The solvent was evaporated and the residue was purified by column chromatography on silica (n-heptane/ethyl acetate gradient) to yield 0.99 g of the title compound as a yellow oil, MS (ISP) 328.3 $(M+H)^+$.

6-Butoxy-5-(2-fluoro-5-trifluoromethyl-phenyl)-nicotinic acid

N-Bromosuccinimide (1.2 g, 6.7 mmol) and 2,2'-azobis-(2-methyl-propionitrile) (5 mg) were added to a solution of 2-butoxy-3-(2-fluoro-5-trifluoromethyl-phenyl)-5-methyl-pyridine (0.96 g, 2.9 mmol) in carbon tetrachloride (30 mL). The mixture was irradiated and boiled with a halogen lamp for 2 h during which time 5 mg of 2,2'-azobis-(2-methyl-propionitrile) was added every 30 min. After cooling the mixture was poured onto sodium bisulfite solution (38–40%, 30 mL). This was extracted with dichloromethane. Organic phases were pooled, washed with water and dried with $MgSO_4$. The solvent was evaporated and the residue (a mixture of 5-bromomethyl-2-butoxy-3-(2-fluoro-5-trifluoromethyl-phenyl)-pyridine and 2-butoxy-5-dibromomethyl-3-(2-fluoro-5-trifluoromethyl-phenyl)-pyridine) was dissolved in ethanol (19 mL). Ammonium hydroxide solution (conc. 5 mL) was added and the mixture was boiled for 1 h. After cooling the reaction mixture was poured onto hydrochloric acid (1 N, 100 mL) and partitioned into diethyl ether. The solvent was evaporated and the residue (a mixture of [6-butoxy-5-(2-fluoro-5-trifluoromethyl-phenyl)-pyridin-3-yl]-methanol and 6-butoxy-5-(2-fluoro-5-trifluoromethyl-phenyl)-pyridine-3-carbaldehyde) was dissolved in pyridine (28 mL). Tetrabutylammonium permanganate (3.1 g, 8.8 mmol) was added and the mixture was heated with stirring for 5 h. After cooling the reaction mixture was poured onto ice water (100 mL), sodium bisulfite solution (38–40%, 40 mL) was added; the mixture was adjusted to acidic pH with hydrochloric acid (250 mL, 2 N) and partitioned into diethyl ether. Organic phases were pooled, and dried with $MgSO_4$. The solvent was evaporated and the residue was purified by column chromatography on silica (n-heptane/ethyl acetate 3:1) to yield 0.51 g of the title compound as a yellow solid, MS (ISP) 356.1 $(M-H)^-$.

6-Butoxy-5-(2-fluoro-5-trifluoromethyl-phenyl)-N-((1R,2R)-2-hydroxy-cyclohexyl)-nicotinamide 6-Butoxy-5-(2-fluoro-5-trifluoromethyl-phenyl)-nicotinic acid (0.10 g, 0.3 mmol) was dissolved in DMF (5 mL). To the solution was added TBTU (0.10 g, 0.3 mmol), N,N-diisopropylethyl amine (0.24 mL, 1.4 mmol) and (1R,2R)-2-amino-cyclohexanol (47 mg, 0.3 mmol). The reaction mixture was stirred for 18 h at room temperature. The solvent was evaporated in vacuo and the residue was purified by column chromatography on silica (n-heptane/ethyl acetate gradient) to yield 78 mg of the title compound as a light yellow solid, mp 172–178° C., MS (ISP) 455.3 $(M+H)^+$.

Example 3

6-Butoxy-5-(4-chloro-phenyl)-N-((1R,2R)-2-hydroxy-cyclohexyl)-nicotinamide

The title compound was synthesized in analogy to Example 2, using 3-bromo-2-chloro-5-methyl-pyridine, 1-butanol, [4-chloro-phenyl]-boronic acid and (1R,2R)-2-amino-cyclohexanol as starting materials, MS (ISP) 403.2 $(M+H)^+$.

Example 4

6-Butoxy-5-(4-chloro-phenyl)-N-(2-cyclopropyl-2-hydroxy-propyl)-nicotinamide 2-Cyclopropyl-2-trimethylsilanyloxy-propionitrile A mixture of 1-cyclopropyl-ethanone (5 g, 59 mmol), potassium cyanide (0.49 g, 7 mmol), trimethylsilyl cyanide (8.8 g, 89 mmol) and 18-crown-6 (0.98 g, 4 mmol) was heated for 30 min to 145° C. Volatiles were removed in vacuo and the residue containing the title compound was used in the next step without purification.

1-Amino-2-cyclopropyl-propan-2-ol

To a suspension of lithium aluminium hydride (4.5 g, 120 mmol) in tetrahydrofuran (120 mL) at 0° C. was added dropwise a solution of 2-cyclopropyl-2-trimethylsilanyloxy-propionitrile (10.9 g, 59 mmol) in tetrahydrofuran (5 mL). The mixture was allowed to warm to room temperature and stirred for 60 h. Excess lithium aluminium hydride was destroyed by careful addition of a saturated $Na_2SO_4$ solution. The mixture was dried with $Na_2SO_4$ and filtered through a $Na_2SO_4$ pad. The solvent was evaporated in vacuo and the residue consisted of the title compound in sufficient purity for subsequent amide coupling reactions, $^1$H NMR ($CDCl_3$): 0.31 (m, 3H), 0.48 (m, 1H), 0.77 (m, 1H), 1.07 (s, 3H, $CH_3$), 2.64 (d, 1H, J~12 Hz), 2.79 (d, 1H, J~12 Hz), 3.68 (s, ~1H, OH).

6-Butoxy-5-(4-chloro-phenyl)-N-(2-cyclopropyl-2-hydroxy-propyl)-nicotinamide

The title compound was synthesized in analogy to Example 2, using 3-bromo-2-chloro-5-methyl-pyridine, 1-butanol, [4-chloro-phenyl]-boronic acid and 1-amino-2-cyclopropyl-propan-2-ol as starting materials, MS (ISP) 403.2 $(M+H)^+$.

Example 5

5-(4-Chloro-phenyl)-6-cyclopropylmethoxy-N-((1R,2R)-2-hydroxy-cyclohexyl)-nicotinamide The title compound was synthesized in analogy to Example 2, using 3-bromo-2-chloro-5-methyl-pyridine, cyclopropanemethanol, [4-chloro-phenyl]-boronic acid and (1R,2R)-2-amino-cyclohexanol as starting materials, MS (ISP) 401.2 $(M+H)^+$.

Example 6

5-(4-Chloro-phenyl)-N-(2-cyclopropyl-2-hydroxy-propyl)-6-cyclopropylmethoxy-nicotinamide The title compound was synthesized in analogy to Example 2, using 3-bromo-2-chloro-5-methyl-pyridine, cyclopropanemethanol, [4-chloro-phenyl]-boronic acid and 1-amino-2-cyclopropyl-propan-2-ol as starting materials, MS (ISP) 401.2 $(M+H)^+$.

Example 7

6-Cyclopropylmethoxy-5-(2-fluoro-5-trifluoromethyl-phenyl)-N-((1R,2R)-2-hydroxy-cyclohexyl)-nicotinamide The title compound was synthesized in analogy to Example 2, using 3-bromo-2-chloro-5-methyl-pyridine, cyclopropanemethanol, [2-fluoro-5-(trifluoromethyl)phenyl]-boronic acid and (1R,2R)-2-amino-cyclohexanol as starting materials, MS (ISP) 453.2 $(M+H)^+$.

Example 8

6-Butoxy-5-(2-chloro-5-trifluoromethyl-phenyl)-N-((1R,2R)-2-hydroxy-cyclohexyl)-nicotinamide The title compound was synthesized in analogy to Example 2, using 3-bromo-2-chloro-5-methyl-pyridine, 1-butanol, [2-chloro-5-(trifluoromethyl)phenyl]-boronic acid and (1R,2R)-2-amino-cyclohexanol as starting materials, MS (ISP) 471.0 $(M+H)^+$.

Example 9

5-(2-Chloro-5-trifluoromethyl-phenyl)-6-cyclopropylmethoxy-N-((1R,2R)-2-hydroxy-cyclohexyl)-nicotinamide The title compound was synthesized in analogy to Example 2, using 3-bromo-2-chloro-5-methyl-pyridine, cyclopropanemethanol, [2-chloro-5-(trifluoromethyl)-phenyl]-boronic acid and (1R,2R)-2-amino-cyclohexanol as starting materials, MS (ISP) 469.1 $(M+H)^+$.

Example 10

6-Butoxy-5-(2,4-dichloro-phenyl)-N-((1R,2R)-2-hydroxy-cyclohexyl)-nicotinamide

The title compound was synthesized in analogy to Example 2, using 3-bromo-2-chloro-5-methyl-pyridine, 1-butanol, [2,4-dichloro-phenyl]-boronic acid and (1R,2R)-2-amino-cyclohexanol as starting materials, MS (ISP) 437.1 $(M+H)^+$.

Example 11

5-(2,4-Dichloro-phenyl)-N-((1R,2R)-2-hydroxy-cyclohexyl)-6-propoxy-nicotinamide

A mixture of 1.5 g (6 mmol) 5-bromo-6-chloro-nicotinic acid methyl ester, 1.8 g (30 mmol) propanol, 1.82 g (12 mmol) 1,8-diazabicyclo[5.4.0]undec-7-ene in 6 mL THF was heated to 74° C. over night. Evaporation of THF was followed by addition of water and ethyl acetate. The organic phase was washed with 1M KHSO4 aq. and the combined aqueous phases re-extracted with ethyl acetate. The combined organic phases were dried with $MgSO_4$ and evaporated to dryness. The crude intermediate was used in the consecutive step without further purification. The residue was partitioned to affect several consecutive reactions and ½ of the residue, 856 mg (4.49 mmol) 2,4-dichloro-phenylboronic acid, 109 mg (0.15 mmol) [1,1'-bis(diphenylphospino)ferrocene] palladium(II) dichloride dichloromethane complex (1:1), 4.49 mL 2N $Na_2CO_3$ aq., in 10 mL toluene and 4.5 mL water was heated to 80° C. over night. KOH was added and heating to 80° C. was continued for 2 h. The mixture was acidified with 4N HCl aq. and extracted with ethyl acetate and evaporated. The residue was purified by preparative HPLC on reversed phase eluting with a gradient formed from acetonitrile/water/HCOOH. The combined product fractions were evaporated to yield 236 mg of 5-(2,4-dichloro-phenyl)-6-propoxy-nicotinic acid. MS (m/e): 324.2 (M–H).

A mixture of 23.5 mg (0.072 mmol) 5-(2,4-dichloro-phenyl)-6-propoxy-nicotinic acid, 29 mg (0.09 mmol) TBTU, 10 mg (0.086 mmol) (1R,2R)-2-amino-cyclohexanol and 47.8 mg (0.37 mmol) DIPEA in 1 DMF was shaken at room temperature over night. Acetic acid was added and purified by preparative HPLC on reversed phase eluting with a gradient formed from acetonitrile/water/HCOOH. The combined product fractions were evaporated to yield 24.9 mg (85%) of the title compound. MS (m/e): 423.2 $(MH^+)$.

Example 12

5-(2,4-Dichloro-phenyl)-N-((1R,2R)-2-hydroxy-cyclohexyl)-6-pentyloxy-nicotinamide The title compound was synthesized in analogy to the procedure described for the preparation of Example 11, using 5-bromo-6-chloro-nicotinic acid methylester, pentanol (commercially available), 2,4-dichlorophenyl-boronic acid (commercially available) and (1R,2R)-2-amino-cyclohexanol (commercially available) as starting materials. MS (m/e): 451.2 (MH$^+$).

Example 13

N-(2-Cyclopropyl-2-hydroxy-propyl)-5-(2,4-dichloro-phenyl)-6-(2-methoxy-ethoxy)-nicotinamide The title compound was synthesized in analogy to the procedure described for the preparation of Example 11, using 5-bromo-6-chloro-nicotinic acid methylester, 2-methoxy-ethanol (commercially available), 2,4-dichlorophenyl-boronic acid (commercially available) and 1-amino-2-cyclopropyl-propan-2-ol (commercially available) as starting materials. MS (m/e): 439.3 (MH$^+$).

Example 14

6-Cyclopropylmethoxy-5-(2,4-dichloro-phenyl)-N-((1R,2R)-2-hydroxy-cyclohexyl)-nicotinamide The title compound was synthesized in analogy to the procedure described for the preparation of Example 11, using 5-bromo-6-chloro-nicotinic acid methylester, cyclopropyl-methanol (commercially available), 2,4-dichlorophenyl-boronic acid (commercially available), and (1R,2R)-2-amino-cyclohexanol (commercially available) as starting materials. MS (m/e): 435.3 (MH$^+$).

Example 15

5-(4-Chloro-phenyl)-N-(2-cyclopropyl-2-hydroxy-propyl)-6-(2-methoxy-ethoxy)-nicotinamide The title compound was synthesized in analogy to the procedure described for the preparation of Example 11, using 5-bromo-6-chloro-nicotinic acid methylester, 2-methoxy-ethanol (commercially available), 4-chlorophenyl-boronic acid (commercially available) and 1-amino-2-cyclopropyl-propan-2-ol (commercially available) as starting materials. MS (m/e): 405.4 (MH$^+$).

Example 16

5-(4-Chloro-phenyl)-N-((1R,2R)-2-hydroxy-cyclohexyl)-6-(2-methoxy-ethoxy)-nicotinamide The title compound was synthesized in analogy to the procedure described for the preparation of Example 11, using 5-bromo-6-chloro-nicotinic acid methylester, 2-methoxy-ethanol (commercially available), 4-chlorophenyl-boronic acid (commercially available) and (1R,2R)-2-amino-cyclohexanol (commercially available) as starting materials. MS (m/e): 405.3 (MH$^+$).

Example 17

5-(4-Chloro-phenyl)-N-(trans-2-hydroxy-cyclohexyl)-6-(2-methoxy-ethoxy)-nicotinamide The title compound was synthesized in analogy to the procedure described for the preparation of Example 11, using 5-bromo-6-chloro-nicotinic acid methylester, 2-methoxy-ethanol (commercially available), 4-chlorophenyl-boronic acid (commercially available) and (trans)-2-amino-cyclohexanol (commercially available) as starting materials. MS (m/e): 405.3 (MH$^+$).

Example 18

5-(4-Chloro-phenyl)-N-(2-cyclopropyl-2-hydroxy-propyl)-6-(3-methoxy-propoxy)-nicotinamide The title compound was synthesized in analogy to the procedure described for the preparation of Example 11, using 5-bromo-6-chloro-nicotinic acid methylester, 3-methoxy-propanol (commercially available), 4-chlorophenyl-boronic acid (commercially available) and 1-amino-2-cyclopropyl-propan-2-ol (commercially available) as starting materials. MS (m/e): 419 (MH$^+$).

Example 19

5-(4-Chloro-phenyl)-N-((1R,2R)-2-hydroxy-cyclohexyl)-6-(3-methoxy-propoxy)-nicotinamide The title compound was synthesized in analogy to the procedure described for the preparation of Example 11, using 5-bromo-6-chloro-nicotinic acid methylester, 3-methoxy-propanol (commercially available), 4-chlorophenyl-boronic acid (commercially available) and (1R,2R)-2-amino-cyclohexanol (commercially available) as starting materials. MS (m/e): 419.1 (MH$^+$).

Example 20

6-Benzylamino-5-(4-chloro-phenyl)-N-((1R,2R)-2-hydroxy-cyclohexyl)-nicotinamide Step 1: 6-Benzylamino-5-bromo-nicotinic acid A mixture of 0.3 g (1.27 mmol) 5-bromo-6-chloro-nicotinic acid methylester and 0.34 g (3.17 mmol) benzylamine in 0.4 mL DMSO was heated to 160° C. in the microwave for 4 min. 0.6 mL water and 0.4 mL 5N KOH aq was added and heated to 160° C. in the microwave for 2 min. Acetic acid and DMF was added and the mixture was purified by preparative HPLC on reversed phase eluting with a gradient formed from acetonitrile/water/HCOOH. The combined product fractions were evaporated to yield 0.195 g (50%) of the title compound. MS (m/e): 307.1 (M–H).

Step 2: 6-Benzylamino-5-(4-chloro-phenyl)-nicotinic acid

A mixture of 77 mg (0.25 mmol) 6-benzylamino-5-bromo-nicotinic acid, 58 mg (0.375 mmol) 4-chlorophenyl boronic acid, 9.1 mg 1,1'-bis(diphenylphosphino)ferrocene-dichloro palladium (II) dichloromethane complex 1:1 and 0.38 mL 2N Na$_2$CO$_3$ aq. in 0.5 mL water and 2 mL dioxane was heated to 85° C. for 20 h. Formic acid was added, filtered and the mixture was purified by preparative HPLC on reversed phase eluting with a gradient formed from acetonitrile/water/HCOOH. The combined product fractions were evaporated to yield 32.4 mg (38%) of the title compound. MS (m/e): 337.3 (M−H).

Step 3: 6-Benzylamino-5-(4-chloro-phenyl)-N-((1R, 2R)-2-hydroxy-cyclohexyl)-nicotinamide A mixture of 16.2 mg (0.047 mmol) 6-benzylamino-5-(4-chloro-phenyl)-nicotinic acid, 19.6 mg (0.06 mmol) TBTU, 6.9 mg (0.06 mmol) (1R,2R)-2-amino-cyclohexanol and 23 mg (0.18 mmol) DIPEA in DMF was shaken at room temperature over night. Acetic acid was added and purified by preparative HPLC on reversed phase eluting with a gradient formed from acetonitrile/water/HCOOH. The combined product fractions were evaporated to yield 14.1 mg (55%) of the title compound. MS (m/e): 436.4 (MH$^+$).

Example 21

5-(4-Chloro-phenyl)-6-(cyclopropylmethyl-amino)-N-((1R,2R)-2-hydroxy-cyclohexyl)-nicotinamide The title compound was synthesized in analogy to the procedure described for the preparation of Example 20, using 5-bromo-6-chloro-nicotinic acid methylester, cyclopropanemethylamine, 4-chlorophenyl-boronic acid and (1R, 2R)-2-amino-cyclohexanol as starting materials. MS (m/e): 400.5 (MH$^+$).

Example 22

5-(4-Chloro-phenyl)-N-(2-cyclopropyl-2-hydroxy-propyl)-6-(2-methoxy-ethylamino)-nicotinamide The title compound was synthesized in analogy to the procedure described for the preparation of Example 20, using 5-bromo-6-chloro-nicotinic acid methylester, 2-methoxy-ethylamine, 4-chlorophenyl-boronic acid and 2-cyclopropyl-2-hydroxy-propylamine (commercially available) as starting materials. MS (m/e): 404.4 (MH$^+$).

Example 23

N-((trans)-2-Hydroxy-cyclohexyl)-6-(2-methoxy-ethoxy)-5-(4-trifluoromethyl-phenyl)-nicotinamide Step 1: 5-Bromo-6-(2-methoxy-ethoxy)-nicotinic acid A mixture of 325 mg (1.3 mmol) 5-Bromo-6-chloro-nicotinic acid methyl ester, 233 mg (3.24 mmol) 2-methoxyethanol and 493 mg (3.24 mmol) DBU was heated under microwave radiation for 2 min to 180° C. 0.65 mL water and 0.49 mL 5N KOH aq. was added and the mixture was heated under microwave radiation for 2 min to 160° C. The mixture was acidified with 1N HCl aq. and extracted with ethyl acetate. After evaporation the residue was purified by preparative HPLC on reversed phase eluting with a gradient formed from acetonitrile/water/HCOOH. The combined product fractions were evaporated to yield 237 mg (66%) of the title compound as white solid. MS (m/e): 274 (M−H).

Step 2: 5-Bromo-N-(trans-2-hydroxy-cyclohexyl)-6-(2-methoxy-ethoxy)-nicotinamide The title compound was synthesised in analogy to the amide coupling procedure described for the synthesis of Example 1, from 5-bromo-6-(2-methoxy-ethoxy)-nicotinic acid and trans-2-amino-cyclohexanol (commercially available). MS (m/e): 373.1 (MH$^+$).

Step 3: N-((trans)-2-Hydroxy-cyclohexyl)-6-(2-methoxy-ethoxy)-5-(4-trifluoromethyl-phenyl)-nicotinamide The title compound was synthesised in analogy to the Suzuki reaction procedure described for the preparation of Example 1, from 5-bromo-N-(trans-2-hydroxy-cyclohexyl)-6-(2-methoxy-ethoxy)-nicotinamide and 4-trifluoromethyl-phenylboronic acid (commercially available). MS (m/e): 439.3 (MH$^+$).

Example 24

N-((trans)-2-Hydroxy-cyclohexyl)-6-(2-methoxy-ethoxy)-5-(4-trifluoromethoxy-phenyl)-nicotinamide The title compound was synthesized in analogy to the procedure described for the preparation of Example 23, using 5-bromo-N-(trans-2-hydroxy-cyclohexyl)-6-(2-methoxy-ethoxy)-nicotinamide and 4-trifluoromethoxyphenylboronic acid (commercially available) as starting materials. MS (m/e): 455.3 (MH$^+$).

Example 25

6-Cyclopropylmethoxy-5-(3,4-difluoro-phenyl)-N-((trans)-2-hydroxy-cyclohexyl)-nicotinamide The title compound was synthesized in analogy to the procedure described for the preparation of Example 23, using 5-bromo-N-(trans-2-hydroxy-cyclohexyl)-6-(2-methoxy-ethoxy)-nicotinamide and 3,4-difluorophenylboronic acid (commercially available) as starting materials. MS (m/e): 403.4 (MH$^+$).

Example 26

6-Cyclopropylmethoxy-5-(4-fluoro-phenyl)-N-((trans)-2-hydroxy-cyclohexyl)-nicotinamide The title compound was synthesized in analogy to the procedure described for the preparation of Example 23, using 5-bromo-N-(trans-2-hydroxy-cyclohexyl)-6-(2-methoxy-ethoxy)-nicotinamide and 4-fluorophenylboronic acid (commercially available) as starting materials. MS (m/e): 385.4 (MH$^+$).

Example 27

6-Cyclopropylmethoxy-N-((trans)-2-hydroxy-cyclohexyl)-5-(4-trifluoromethyl-phenyl)-nicotinamide The title compound was synthesized in analogy to the procedure described for the preparation of Example 23, using 5-bromo-6-cyclopropylmethoxy-N-(trans-2-hydroxy-cyclohexyl)-nicotinamide (synthesised in analogy to the procedure described for the synthesis of Example 23, from 5-bromo-6-chloro-nicotinic acid methyl ester, cyclopropylmethanol (commercially available) and trans-2-amino-cyclohexanol (commercially available)) and 4-fluorophenylboronic acid (commercially available) as starting materials. MS (m/e): 435.4 (MH$^+$).

Example 28

6-Cyclopropylmethoxy-N-((trans)-2-hydroxy-cyclohexyl)-5-(4-trifluoromethoxy-phenyl)-nicotinamide The title compound was synthesized in analogy to the procedure described for the preparation of Example 23, using 5-bromo-6-cyclopropylmethoxy-N-(trans-2-hydroxy-cyclohexyl)-nicotinamide and 4-trifluoromethoxyphenylboronic acid (commercially available) as starting materials. MS (m/e): 451.3 (MH$^+$).

Example 29

5-(4-Cyano-phenyl)-6-cyclopropylmethoxy-N-((1S,2S)-2-hydroxy-cyclohexyl)-nicotinamide The title compound was synthesized in analogy to the procedure described for the preparation of Example 23, using 5-bromo-6-cyclopropylmethoxy-N-(trans-2-hydroxy-cyclohexyl)-nicotinamide and 4-cyanomethoxyphenylboronic acid (commercially available) as starting materials. MS (m/e): 392.2 (MH$^+$).

Example 30

(RS)-5-(4-Chloro-phenyl)-N-(2-hydroxy-butyl)-6-(2-methoxy-ethoxy)-nicotinamide

The title compound was synthesized in analogy to Example 102, using 5-bromo-6-hydroxy-nicotinic acid methyl ester, 2-methoxyethanol, (4-chloro-phenyl)-boronic acid and 1-aminobutanol as starting materials to yield (RS)-5-(4-Chloro-phenyl)-N-(2-hydroxy-butyl)-6-(2-methoxy-ethoxy)-nicotinamide. MS (ISP) 379.3 (M+H)$^+$.

Example 31

(RS)-5-(4-Chloro-phenyl)-6-(2-methoxy-ethoxy)-N-(3,3,3-trifluoro-2-hydroxy-propyl)-nicotinamide The title compound was synthesized in analogy to Example 102, using 5-bromo-6-hydroxy-nicotinic acid methyl ester, 2-methoxyethanol, (4-chloro-phenyl)-boronic acid and 3-amino-1,1,1-trifluoro-propan-2-ol (CAS [431-38-9]) as starting materials to yield (RS)-5-(4-chloro-phenyl)-6-(2-methoxy-ethoxy)-N-(3,3,3-trifluoro-2-hydroxy-propyl)-nicotinamide. MS (ISP) 419.3 (M+H)$^+$.

Example 32

6-Benzyloxy-5-(4-chloro-phenyl)-N-((1R,2R)-2-hydroxy-cyclohexyl)-nicotinamide 6-Benzyloxy-5-bromo-nicotinic acid A suspension of 5-bromo-6-chloro-nicotinic acid (CAS [29241-62-1], 1 g), benzylalcohol (0.686 g) and KOH (1.104 g) in DMSO (4 ml) was stirred at 140° C. for 15 min. DMSO (2 ml) was added and the mixture was stirred at 140° C. for 30 min. The mixture was cooled to room temperature. Ice was added and the mixture was acidified using 1 M HCl. The mixture was extracted with ethyl acetate. The organic phase was washed with brine, dried, filtered and concentrated. The product was purified by flash chromatography (SiO$_2$, CH$_2$Cl$_2$=>CH$_2$Cl$_2$/MeOH 4:1) to give 6-benzyloxy-5-bromo-nicotinic acid (0.308 g) as a white solid.

6-Benzyloxy-5-bromo-N-((1R,2R)-2-hydroxy-cyclohexyl)-nicotinamide

In analogy to example 1f, 6-benzyloxy-5-bromo-nicotinic acid was coupled with (1R,2R)-2-amino-cyclohexanol hydrochloride (CAS [5456-63-3]) using TBTU and N,N-diisopropyl ethyl amine in N,N-dimethylacetamide to give 6-benzyloxy-5-bromo-N-((1R,2R)-2-hydroxy-cyclohexyl)-nicotinamide as an orange solid.

6-Benzyloxy-5-(4-chloro-phenyl)-N-((1R,2R)-2-hydroxy-cyclohexyl)-nicotinamide

To a solution of 6-benzyloxy-5-bromo-N-((1R,2R)-2-hydroxy-cyclohexyl)-nicotinamide (85 mg) in 1,2-dimethoxy-ethane (1.6 ml) was added tetrakis(triphenyl-phosphine) palladium(0) (24.5 mg). The mixture was stirred for 10 min. 4-chlorophenyl-boronic acid (37.2 mg) was dissolved in 0.7 ml EtOH and added to the reaction mixture. A solution of Na$_2$CO$_3$ (190 mg) in water (1 ml) was added. The reaction mixture was stirred at 85° C. for 3 h. After cooling to room temperature, the mixture was filtered and the filtrate was concentrated. The residue was dissolved in ethyl acetate and washed with brine. The org. phase was dried, filtered and concentrated. The product was purified by flash chromatography (SiO$_2$, CH$_2$Cl$_2$=>CH$_2$Cl$_2$MeOH 4:1) to give 6-benzyloxy-5-(4-chloro-phenyl)-N-((1R,2R)-2-hydroxy-cyclohexyl)-nicotinamide (50.6 mg) as a white solid. MS (ISP) 437.2 (M+H)$^+$.

Example 33

5-(4-Chloro-phenyl)-N-(3-hydroxy-2,2-dimethyl-propyl)-6-(2-methoxy-ethoxy)-nicotinamide The title compound was synthesized in analogy to Example 102, using 5-bromo-6-hydroxy-nicotinic acid methyl ester, 2-methoxyethanol, (4-chloro-phenyl)-boronic acid and 3-amino-2,2-dimethyl-1-propanol as starting materials to yield 5-(4-chloro-phenyl)-N-(3-hydroxy-2,2-dimethyl-propyl)-6-(2-methoxy-ethoxy)-nicotinamide. MS (ISP) 393.1 (M+H)$^+$.

Example 34

(RS)-5-(4-Chloro-phenyl)-N-(2-hydroxymethyl-butyl)-6-(2-methoxy-ethoxy)-nicotinamide The title compound was synthesized in analogy to Example 102, using 5-bromo-6-hydroxy-nicotinic acid methyl ester, 2-methoxyethanol, (4-chloro-phenyl)-boronic acid and 2-(aminomethyl)-1-butanol (CAS [16519-75-8]) as starting materials to yield (RS)-5-(4-chloro-phenyl)-N-(2-hydroxymethyl-butyl)-6-(2-methoxy-ethoxy)-nicotinamide. MS (ISP) 393.3 (M+H)$^+$.

Example 35

5-(4-Chloro-phenyl)-N-((1RS,2RS)-2-hydroxy-cyclohexylmethyl)-6-(2-methoxy-ethoxy)-nicotinamide The title compound was synthesized in analogy to Example 102, using 5-bromo-6-hydroxy-nicotinic acid methyl ester, 2-methoxyethanol, (4-chloro-phenyl)-boronic acid and cis-2-aminomethyl-1-cyclohexanol hydrochloride as starting materials to yield racemic 5-(4-chloro-phenyl)-N-((1RS,2RS)-2-hydroxy-cyclohexylmethyl)-6-(2-methoxy-ethoxy)-nicotinamide. MS (ISP) 419.3 (M+H)$^+$.

Example 36

5-(4-Chloro-phenyl)-N-((1R,2R)-2-methoxy-cyclohexyl)-6-(2-methoxy-ethoxy)-nicotinamide To a suspension of 5-(4-chloro-phenyl)-N-((1R,2R)-2-hydroxy-cyclohexyl)-6-(2-methoxy-ethoxy)-nicotinamide (example 16, 50 mg) in THF (0.5 ml) was added sodium hydride dispersion (60% in mineral oil, 5.4 mg) at 0° C. The mixture was stirred at room temperature for 1 h. Methyl iodide (18.4 mg) was added and the mixture was stirred overnight at room temperature. The reaction mixture was concentrated in vacuo. The product was purified by flash chromatography (SiO$_2$, CH$_2$Cl$_2$=>CH$_2$Cl$_2$MeOH 9:1) to give 5-(4-chloro-phenyl)-N-((1R,2R)-2-methoxy-cyclohexyl)-6-(2-methoxy-ethoxy)-nicotinamide (27 mg) as a colorless oil. MS (ISP) 419.4 (M+H)$^+$.

Example 37

5-(4-Chloro-phenyl)-N-((1SR,2RS)-2-hydroxy-cyclohexylmethyl)-6-(2-methoxy-ethoxy)-nicotinamide The title compound was synthesized in analogy to Example 102, using 5-bromo-6-hydroxy-nicotinic acid methyl ester, 2-methoxyethanol, (4-chloro-phenyl)-boronic acid and trans-2-aminomethyl-1-cyclohexanol hydrochloride as starting materials to yield racemic 5-(4-chloro-phenyl)-N-((1SR,2RS)-2-hydroxy-cyclohexylmethyl)-6-(2-methoxy-ethoxy)-nicotinamide. MS (ISP) 419.1 (M+H)$^+$.

Example 38

5-(4-Chloro-phenyl)-N-(1-hydroxy-cyclohexylmethyl)-6-(2-methoxy-ethoxy)-nicotinamide The title compound was synthesized in analogy to Example 102, using 5-bromo-6-hydroxy-nicotinic acid methyl ester, 2-methoxyethanol, (4-chloro-phenyl)-boronic acid and 1-aminomethyl-1-cyclohexanol hydrochloride as starting materials to yield 5-(4-chloro-phenyl)-N-(1-hydroxy-cyclohexylmethyl)-6-(2-methoxy-ethoxy)-nicotinamide. MS (ISP) 419.0 (M+H)$^+$.

Example 39

5-(4-Chloro-phenyl)-N-((1R,2R)-2-hydroxy-cyclohexyl)-6-(1-methyl-cyclopropyl-methoxy)-nicotinamide The title compound was synthesized in analogy to Example 75, using 5-bromo-6-chloro-3-pyridinecarboxylic acid, 1-methylcyclopropanemethanol, (4-chloro-phenyl)-boronic acid and (1R,2R)-2-amino-cyclohexanol hydrochloride as starting materials to yield 5-(4-chloro-phenyl)-N-((1R,2R)-2-hydroxy-cyclohexyl)-6-(1-methyl-cyclopropylmethoxy)-nicotinamide. MS (ISP) 415.3(M+H)$^+$.

Example 40

(−)-5-(4-Chloro-phenyl)-N-(2-cyclopropyl-2-hydroxy-propyl)-6-(2-methoxy-ethoxy)-nicotinamide By separation of the enantiomers of 5-(4-chloro-phenyl)-N-(2-cyclopropyl-2-hydroxy-propyl)-6-(2-methoxy-ethoxy)-nicotinamide (Example 15) with heptane/ethanol on ChiralpakAD® the (−)-enantiomer was obtained. MS (ISP) 405.3 (M+H)$^+$, $\alpha_D^{20}$: −1.4° in CHCl$_3$.

Example 41

(+)-5-(4-Chloro-phenyl)-N-(2-cyclopropyl-2-hydroxy-propyl)-6-(2-methoxy-ethoxy)-nicotinamide Separation of the enantiomers of 5-(4-chloro-phenyl)-N-(2-cyclopropyl-2-hydroxy-propyl)-6-(2-methoxy-ethoxy)-nicotinamide (example 15) with heptane/ethanol on ChiralpakAD® yielded the (+)-enantiomer. MS (ISP) 405.3 (M+H)$^+$, $\alpha_D^{20}$: +4.9° in CHCl$_3$.

Example 42

5-(4-Chloro-phenyl)-6-cyclopentylmethoxy-N-((1R,2R)-2-hydroxy-cyclohexyl)-nicotinamide The title compound was synthesized in analogy to Example 75, using 5-bromo-6-chloro-3-pyridinecarboxylic acid, cyclopentanemethanol, (4-chloro-phenyl)-boronic acid and (1R,2R)-2-amino-cyclohexanol hydrochloride as starting materials to yield 5-(4-chloro-phenyl)-6-cyclopentylmethoxy-N-((1R,2R)-2-hydroxy-cyclohexyl)-nicotinamide. MS (ISP) 429.5 (M+H)$^+$.

Example 43

5-(4-Chloro-phenyl)-6-(2-cyclopropyl-ethoxy)-N-((1R,2R)-2-hydroxy-cyclohexyl)-nicotinamide The title compound was synthesized in analogy to Example 75, using 5-bromo-6-chloro-3-pyridinecarboxylic acid, cyclopropylethanol, (4-chloro-phenyl)-boronic acid and (1R,2R)-2-amino-cyclohexanol hydrochloride as starting materials to yield 5-(4-chloro-phenyl)-6-(2-cyclopropyl-ethoxy)-N-((1R,2R)-2-hydroxy-cyclohexyl)-nicotinamide. MS (ISP) 415.2 (M+H)$^+$.

Example 44

5-(4-Chloro-phenyl)-6-cyclobutylmethoxy-N-((1R,2R)-2-hydroxy-cyclohexyl)-nicotinamide The title compound was synthesized in analogy to Example 75, using 5-bromo-6-chloro-3-pyridinecarboxylic acid, cyclobutanemethanol, (4-chloro-phenyl)-boronic acid and (1R,2R)-2-amino-cyclohexanol hydrochloride as starting materials to yield 5-(4-chloro-phenyl)-6-cyclobutylmethoxy-N-((1R,2R)-2-hydroxy-cyclohexyl)-nicotinamide. MS (ISP) 415.4 (M+H)$^+$.

Example 45

5-(4-Chloro-phenyl)-6-(3,3-dimethyl-butoxy)-N-((1R,2R)-2-hydroxy-cyclohexyl)-nicotinamide The title compound was synthesized in analogy to Example 75, using 5-bromo-6-chloro-3-pyridinecarboxylic acid, 3,3-dimethyl-1-butanol, (4-chloro-phenyl)-boronic acid and (1R,2R)-2-amino-cyclohexanol hydrochloride as starting materials to yield 5-(4-chloro-phenyl)-6-(3,3-dimethyl-butoxy)-N-((1R,2R)-2-hydroxy-cyclohexyl)-nicotinamide. MS (ISP) 431.4 (M+H)$^+$.

Example 46

5-(4-Chloro-phenyl)-N-((1RS,2RS)-2-hydroxy-cyclohexylmethyl)-6-(1-methyl-cyclopropylmethoxy)-nicotinamide The title compound was synthesized in analogy to Example 75, using 5-bromo-6-chloro-3-pyridinecarboxylic acid, 1-methyl-cyclopropanemethanol, (4-chloro-phenyl)-boronic acid and cis-2-aminomethyl-1-cyclohexanol hydrochloride as starting materials to yield racemic 5-(4-chloro-phenyl)-N-((1RS,2RS)-2-hydroxy-cyclohexylmethyl)-6-(1-methyl-cyclopropylmethoxy)-nicotinamide. MS (ISP) 429.5 (M+H)$^+$.

Example 47

6-Benzyloxy-5-(4-chloro-phenyl)-N-((1RS,2RS)-2-hydroxy-cyclohexylmethyl)-nicotinamide The title compound was synthesized in analogy to Example 75, using 5-bromo-6-chloro-3-pyridinecarboxylic acid, benzylalcohol, (4-chloro-phenyl)-boronic acid and cis-2-aminomethyl-1-cyclohexanol hydrochloride as starting materials to yield racemic 6-benzyloxy-5-(4-chloro-phenyl)-N-((1RS,2RS)-2-hydroxy-cyclohexylmethyl)-nicotinamide. MS (ISP) 451.3 (M+H)$^+$.

Example 48

5-(4-Fluoro-phenyl)-N-((1R,2R)-2-hydroxy-cyclohexyl)-6-(2-methoxy-ethoxy)-nicotinamide The title compound was synthesized in analogy to the procedure described for the preparation of Example 23, using 5-bromo-6-chloro-nicotinic acid methyl ester, 2-methoxy-ethanol (commercially available), 4-fluorophenylboronic acid (commercially available) and (1R,2R)-2-amino-cyclohexanol (commercially available) as starting materials. MS (m/e): 389.2 (MH$^+$).

Example 49

N-((1R,2R)-2-Hydroxy-cyclohexyl)-6-(2-methoxy-ethoxy)-5-(4-trifluoromethyl-phenyl)-nicotinamide The title compound was synthesized in analogy to the procedure described for the preparation of Example 23, using 5-bromo-6-chloro-nicotinic acid methyl ester, 2-methoxy-ethanol (commercially available), 4-trifluoromethylphenylboronic acid (commercially available) and (1R,2R)-2-amino-cyclohexanol (commercially available) as starting materials. MS (m/e): 439 (MH$^+$).

Example 50

N-((1R,2R)-2-Hydroxy-cyclohexyl)-6-(2-methoxy-ethoxy)-5-(4-trifluoromethoxy-phenyl)-nicotinamide The title compound was synthesized in analogy to the procedure described for the preparation of Example 23, using 5-bromo-6-chloro-nicotinic acid methyl ester, 2-methoxy-ethanol (commercially available), 4-trifluoromethoxyphenylboronic acid (commercially available) and (1R,2R)-2-amino-cyclohexanol (commercially available) as starting materials. MS (m/e): 455.1 (MH$^+$).

Example 51

5-(4-Chloro-phenyl)-N-((1R,2R)-2-hydroxy-cyclohexyl)-6-(2-isopropoxy-ethoxy)-nicotinamide The title compound was synthesized in analogy to the procedure described for the preparation of Example 23, using 5-bromo-6-chloro-nicotinic acid methyl ester, 2-isopropoxy-ethanol (commercially available), 4-chlorophenylboronic acid (commercially available) and (1R,2R)-2-amino-cyclohexanol (commercially available) as starting materials. MS (m/e): 433.2 (MH$^+$).

Example 52

5-(4-Fluoro-phenyl)-N-((1R,2R)-2-hydroxy-cyclohexyl)-6-(2-isopropoxy-ethoxy)-nicotinamide The title compound was synthesized in analogy to the procedure described for the preparation of Example 23, using 5-bromo-6-chloro-nicotinic acid methyl ester, 2-isopropoxy-ethanol (commercially available), 4-fluorophenylboronic acid (commercially available) and (1R,2R)-2-amino-cyclohexanol (commercially available) as starting materials. MS (m/e): 417.3 (MH$^+$).

Example 53

5-(4-Chloro-phenyl)-N-((1R,2R)-2-hydroxy-cyclohexyl)-6-[(2-methoxy-ethyl)-methyl-amino]-nicotinamide The title compound was synthesized in analogy to the procedure described for the preparation of Example 23, using 5-bromo-6-chloro-nicotinic acid methyl ester, (2-methoxy-ethyl)-methyl-amine (commercially available), 4-chlorophenylboronic acid (commercially available) and (1R,2R)-2-amino-cyclohexanol (commercially available) as starting materials. MS (m/e): 418.3 (MH$^+$).

Example 54

N-((1R,2R)-2-Hydroxy-cyclohexyl)-6-[(2-methoxy-ethyl)-methyl-amino]-5-(4-trifluoromethyl-phenyl)-nicotinamide The title compound was synthesized in analogy to the procedure described for the preparation of Example 23, using 5-bromo-6-chloro-nicotinic acid methyl ester, (2-methoxy-ethyl)-methyl-amine (commercially available), 4-trifluoromethyl-phenylboronic acid (commercially available) and (1R,2R)-2-amino-cyclohexanol (commercially available) as starting materials. MS (m/e): 452 (MH$^+$).

Example 55

5-(4-Chloro-phenyl)-6-([1,3]dioxolan-4-ylmethoxy)-N-((1R,2R)-2-hydroxy-cyclohexyl)-nicotinamide The title compound was synthesized in analogy to the procedure described for the preparation of Example 23, using 5-bromo-6-chloro-nicotinic acid methyl ester, [1,3]dioxolan-4-yl-methanol (commercially available), 4-chlorophenylboronic acid (commercially available) and (1R,2R)-2-amino-cyclohexanol (commercially available) as starting materials. MS (m/e): 433.2 (MH$^+$).

Example 56

6-([1,3]Dioxolan-4-ylmethoxy)-N-((1R,2R)-2-hydroxy-cyclohexyl)-5-(4-trifluoro-methyl-phenyl)-nicotinamide The title compound was synthesized in analogy to the procedure described for the preparation of Example 23, using 5-bromo-6-chloro-nicotinic acid methyl ester, [1,3]dioxolan-4-yl-methanol (commercially available), 4-trifluoromethylphenylboronic acid (commercially available) and (1R,2R)-2-amino-cyclohexanol (commercially available) as starting materials. MS (m/e): 467.1 (MH$^+$).

Example 57

6-Cyclopropylmethoxy-5-(4-fluoro-phenyl)-N-((1R,2R)-2-hydroxy-cyclohexyl)-nicotinamide The title compound was synthesized in analogy to the procedure described for the preparation of Example 23, using 5-bromo-6-chloro-nicotinic acid methyl ester, cyclopropylmethanol (commercially available), 4-fluorophenylboronic acid (commercially available) and (1R,2R)-2-amino-cyclohexanol (commercially available) as starting materials. MS (m/e): 385.3 (MH$^+$).

Example 58

5-(4-Chloro-phenyl)-N-((1R,2R)-2-hydroxy-cyclohexyl)-6-isobutoxy-nicotinamide The title compound was synthesized in analogy to Example 75, using 5-bromo-6-chloro-3-pyridinecarboxylic acid, 2-methyl-propanol, (4-chloro-phenyl)-boronic acid and (1R,2R)-2-amino-cyclohexanol hydrochloride as starting materials to yield 5-(4-chloro-phenyl)-N-((1R,2R)-2-hydroxy-cyclohexyl)-6-isobutoxy-nicotinamide. MS (ISP) 403.4 (M+H)$^+$.

Example 59

5-(4-Chloro-phenyl)-6-(2-ethoxy-ethoxy)-N-((1R,2R)-2-hydroxy-cyclohexyl)-nicotinamide The title compound was synthesized in analogy to Example 75, using 5-bromo-6-chloro-3-pyridinecarboxylic acid, 2-ethoxy-ethanol, (4-chloro-phenyl)-boronic acid and (1R,2R)-2-amino-cyclohexanol hydrochloride as starting materials to yield 5-(4-chloro-phenyl)-6-(2-ethoxy-ethoxy)-N-((1R,2R)-2-hydroxy-cyclohexyl)-nicotinamide. MS (ISP) 419.3 (M+H)$^+$.

Example 60

5-(4-Chloro-phenyl)-N-((1R,2R)-2-hydroxy-cyclohexyl)-6-(3-methyl-butoxy)-nicotinamide The title compound was synthesized in analogy to Example 75, using 5-bromo-6-chloro-3-pyridinecarboxylic acid, 3-methyl-butanol, (4-chloro-phenyl)-boronic acid and (1R,2R)-2-amino-cyclohexanol hydrochloride as starting materials to yield 5-(4-chloro-phenyl)-N-((1R,2R)-2-hydroxy-cyclohexyl)-6-(3-methyl-butoxy)-nicotinamide. MS (ISP) 417.5 (M+H)$^+$.

Example 61

(−)-cis-5-(4-Chloro-phenyl)-6-cyclopropylmethoxy-N-2-hydroxy-cyclohexylmethyl)-nicotinamide The title compound was synthesized in analogy to Example 2, using 3-bromo-2-chloro-5-methyl-pyridine, hydroxymethylcyclopropane, [4-chloro-phenyl]-boronic acid and cis-2-aminomethyl-1-cyclohexanol as starting materials to yield racemic cis-5-(4-chloro-phenyl)-6-cyclopropylmethoxy-N-2-hydroxy-cyclohexylmethyl)-nicotinamide. Separation with heptane/ethanol on ChiralpakAD® yielded the (−)-enantiomer, MS (ISP) 415.2 (M+H)$^+$, $\alpha_D^{20}$: −17.8° in MeOH.

Example 62

6-(4-Carbamoyl-butoxy)-5-(4-chloro-phenyl)-N-((1R,2R)-2-hydroxy-cyclohexyl)-nicotinamide The title compound was synthesized in analogy to Example 75, using 5-bromo-6-chloro-3-pyridinecarboxylic acid, 5-hydroxyvaleramide, (4-chloro-phenyl)-boronic acid and (1R,2R)-2-amino-cyclohexanol hydrochloride as starting materials to yield 6-(4-carbamoyl-butoxy)-5-(4-chloro-phenyl)-N-((1R,2R)-2-hydroxy-cyclohexyl)-nicotinamide. MS (ISP) 446.1 (M+H)$^+$.

Example 63

(−)-5-(4-Chloro-phenyl)-6-cyclopropylmethoxy-N-(2-hydroxymethyl-butyl)-nicotinamide The title compound was synthesized in analogy to Example 2, using 3-bromo-2-chloro-5-methyl-pyridine, hydroxymethylcyclopropane, [4-chloro-phenyl]-boronic acid and 2-aminomethyl-1-butanol as starting materials to yield racemic 5-(4-chloro-phenyl)-6-cyclopropylmethoxy-N-(2-hydroxymethyl-butyl)-nicotinamide. Separation with heptane/ethanol on ChiralpakAD® yielded the (−)-enantiomer, MS (ISP) 389.1 (M+H)$^+$, $\alpha_D^{20}$: −4.6° in MeOH.

Example 64

(RS)-5-(4-Chloro-phenyl)-N-(2-hydroxymethyl-pentyl)-6-(2-methoxy-ethoxy)-nicotinamide The title compound was synthesized in analogy to Example 102, using 5-bromo-6-hydroxy-nicotinic acid methyl ester, 2-methoxyethanol, (4-chloro-phenyl)-boronic acid and 2-(aminomethyl)-1-pentanol as starting materials to yield (RS)-5-(4-chloro-phenyl)-N-(2-hydroxymethyl-pentyl)-6-(2-methoxy-ethoxy)-nicotinamide. MS (ISP) 407.5 (M+H)$^+$.

Example 65

6-Cyclopropylmethoxy-N-((1R,2R)-2-hydroxy-cyclohexyl)-5-(4-trifluoromethyl-phenyl)-nicotinamide The title compound was synthesized in analogy to the procedure described for the preparation of Example 11, using 5-bromo-6-chloro-nicotinic acid methylester, cyclopropylmethanol (commercially available), 4-trifluoromethylphenyl-boronic acid (commercially available) and (1R,2R)-2-amino-cyclohexanol (commercially available) as starting materials. MS (m/e): 435 (MH$^+$).

Example 66

5-(4-Chloro-phenyl)-N-((1R,2R)-2-hydroxy-cyclohexyl)-6-(oxetan-2-ylmethoxy)-nicotinamide The title compound was synthesized in analogy to Example 75, using 5-bromo-6-chloro-3-pyridinecarboxylic acid, 2-hydroxymethyloxetane, (4-chloro-phenyl)-boronic acid and (1R,2R)-2-amino-cyclohexanol hydrochloride as starting materials to yield 5-(4-chloro-phenyl)-N-((1R,2R)-2-hydroxy-cyclohexyl)-6-(oxetan-2-ylmethoxy)-nicotinamide. MS (ISP) 417.2 (M+H)$^+$.

Example 67

5-(4-Chloro-phenyl)-N-((1R,2R)-2-hydroxy-cyclohexyl)-6-(2,2,2-trifluoro-ethoxy)-nicotinamide The title compound was synthesized in analogy to the procedure described for the preparation of Example 11, using 5-bromo-6-chloro-nicotinic acid methylester, 2,2,2-trifluoro-ethanol (commercially available), 4-chlorophenyl-boronic acid (commercially available) and (1R,2R)-2-amino-cyclohexanol (commercially available) as starting materials. MS (m/e): 429.1 (MH$^+$).

Example 68

5-(4-Chloro-phenyl)-N-(2-cyclopropyl-2-hydroxy-propyl)-6-(2,2,2-trifluoro-ethoxy)-nicotinamide The title compound was synthesized in analogy to the procedure described for the preparation of Example 11, using 5-bromo-6-chloro-nicotinic acid methylester, 2,2,2-trifluoro-ethanol (commercially available), 4-chlorophenyl-boronic acid (commercially available) and 2-cyclopropyl-2-hydroxy-propylamine (commercially available) as starting materials. MS (m/e): 429.1 (MH$^+$).

Example 69

5-(4-Fluoro-phenyl)-N-((1R,2R)-2-hydroxy-cyclohexyl)-6-(2,2,2-trifluoro-ethoxy)-nicotinamide The title compound was synthesized in analogy to the procedure described for the preparation of Example 11, using 5-bromo-6-chloro-nicotinic acid methylester, 2,2,2-trifluoro-ethanol (commercially available), 4-fluorophenyl-boronic acid (commercially available) and (1R,2R)-2-amino-cyclohexanol (commercially available) as starting materials. MS (m/e): 413.1 (MH$^+$).

Example 70

N-(2-Cyclopropyl-2-hydroxy-propyl)-5-(4-fluoro-phenyl)-6-(2,2,2-trifluoro-ethoxy)-nicotinamide The title compound was synthesized in analogy to the procedure described for the preparation of Example 11, using 5-bromo-6-chloro-nicotinic acid methylester, 2,2,2-trifluoro-ethanol (commercially available), 4-fluorophenyl-boronic acid (commercially available) and 2-cyclopropyl-2-hydroxy-propylamine (commercially available) as starting materials. MS (m/e): 413 (MH$^+$).

Example 71

N-((1R,2R)-2-Hydroxy-cyclohexyl)-6-(2,2,2-trifluoro-ethoxy)-5-(4-trifluoromethyl-phenyl)-nicotinamide The title compound was synthesized in analogy to the procedure described for the preparation of Example 11, using 5-bromo-6-chloro-nicotinic acid methylester, 2,2,2-trifluoro-ethanol (commercially available), 4-trifluoromethylphenyl-boronic acid (commercially available) and (1R,2R)-2-amino-cyclohexanol (commercially available) as starting materials. MS (m/e): 463.1 (MH$^+$).

Example 72

N-(2-Cyclopropyl-2-hydroxy-propyl)-6-(2,2,2-trifluoro-ethoxy)-5-(4-trifluoromethyl-phenyl)-nicotinamide The title compound was synthesized in analogy to the procedure described for the preparation of Example 11, using 5-bromo-6-chloro-nicotinic acid methylester, 2,2,2-trifluoro-ethanol (commercially available), 4-trifluoromethylphenyl-boronic acid (commercially available) and 2-cyclopropyl-2-hydroxy-propylamine (commercially available) as starting materials. MS (m/e): 463.1 (MH$^+$).

Example 73

N-((1R,2R)-2-Hydroxy-cyclohexyl)-6-(2,2,2-trifluoro-ethoxy)-5-(4-trifluoromethoxy-phenyl)-nicotinamide The title compound was synthesized in analogy to the procedure described for the preparation of Example 11, using 5-bromo-6-chloro-nicotinic acid methylester, 2,2,2-trifluoro-ethanol (commercially available), 4-trifluoromethoxyphenyl-boronic acid (commercially available) and (1R,2R)-2-amino-cyclohexanol (commercially available) as starting materials. MS (m/e): 479 (MH$^+$).

Example 74

5-(4-Chloro-phenyl)-N-((1RS,2RS)-2-hydroxy-cyclohexylmethyl)-6-[(2-methoxy-ethyl)-methyl-amino]-nicotinamide 5-Bromo-6-[(2-methoxy-ethyl)-methyl-amino]-nicotinic acid A suspension of 5-bromo-6-chloro-nicotinic acid methyl ester (1 g) and N-(2-methoxyethyl)methylamine (0.89 g) in 1,8-diazabicyclo[5.4.0]undec-7-ene (1.519 g) was stirred at 60° C. for 3 h and at 90° C. for 1 h. 2 M NaOH (3.99 ml) was added and the mixture was stirred at 90° C. for 15 min. After cooling to room temperature 2 M HCl (3.99 ml) was added. The mixture was acidified using concentrated citric acid solution. The mixture was extracted with ethyl acetate. The org. phase was washed with brine, dried, filtered and concentrated. The product was purified by flash chromatography (SiO$_2$, CH$_2$Cl$_2$=>CH$_2$Cl$_2$/MeOH 4:1) to give 5-bromo-6-[(2-methoxy-ethyl)-methyl-amino]-nicotinic acid (1.06 g) as a white solid.

5-(4-Chloro-phenyl)-6-[(2-methoxy-ethyl)-methyl-amino]-nicotinic acid

In analogy to example 32c, 5-bromo-6-[(2-methoxy-ethyl)-methyl-amino]-nicotinic acid was reacted with 4-chlorophenylboronic acid to give 5-(4-chloro-phenyl)-6-[(2-methoxy-ethyl)-methyl-amino]-nicotinic acid as an off-white solid.

5-(4-Chloro-phenyl)-N-((1RS,2RS)-2-hydroxy-cyclohexylmethyl)-6-[(2-methoxy-ethyl)-methyl-amino]-nicotinamide In analogy to example 1f, 5-(4-chloro-phenyl)-6-[(2-methoxy-ethyl)-methyl-amino]-nicotinic acid was coupled with cis-2-aminomethyl-1-cyclohexanol hydrochloride using TBTU and N,N-diisopropyl ethyl amine in N,N-dimethylacetamide to give racemic 5-(4-chloro-phenyl)-N-((1RS,2RS)-2-hydroxy-cyclohexylmethyl)-6-[(2-methoxy-ethyl)-methyl-amino]-nicotinamide as an off-white solid. MS (ISP) 432.4 (M+H)$^+$.

Example 75

(−)-cis-6-Cyclopropylmethoxy-5-(4-fluoro-phenyl)-N-(2-hydroxy-cyclohexylmethyl)-nicotinamide

5-Bromo-6-cyclopropylmethoxy-nicotinic acid

Potassium hydroxide (3.8 g, 51 mmol) was added to a solution of 5-bromo-6-chloro-3-pyridinecarboxylic acid (CAS 29241-62-1; 3 g, 13 mmol) and cyclopropanemethanol (1.5 mL, 19 mmol) in dimethylsulfoxide (12 mL). The mixture was microwaved at 100° C. for 4 min and poured into a mixture of water (50 mL) and citric acid (150 mL, 10%). The precipitating solid was collected by filtration, washed with water, dissolved in ethyl acetate and dried with Na$_2$SO$_4$. The solvent was removed to yield a solid which was stirred with a mixture of heptane/ethylacetate (40 mL, 1:1), filtered, washed with heptane and dried to yield 2.45 g of the title compound as colorless solid, MS (ISP) 270.1, 272.1 (M−H)$^−$.

6-Cyclopropylmethoxy-5-(4-fluoro-phenyl)-nicotinic acid

5-Bromo-6-cyclopropylmethoxy-nicotinic acid (2.28 g, 8 mmol) was dissolved in a mixture of toluene (40 mL) and dimethylformamide (4 mL). To this solution was added [4-fluoro-phenyl]-boronic acid (1.2 g, 8 mmol), [1,1'-bis(diphenylphosphino)-ferrocene]-dichloropalladium(II) dichloro-methane complex (307 mg), and 2 N sodium carbonate solution (33 mL). The whole mixture was heated with stirring at 90° C. for 4 h, cooled to room temperature and filtered. Phases were separated; the organic phase was discarded and the water phase was acidified with 1 N hydrochloric acid (pH 2) and extracted with ethylacetate. Etylacetate phases were pooled, dried with Na$_2$SO$_4$ and filtered over a small silica gel pad (20 g). The solvent was removed to yield a solid which was stirred with heptane (200 mL), filtered, washed with heptane and dried to yield 1.77 g of the title compound as beige solid, MS (ISP) 286.0 (M−H)$^−$.

cis-6-Cyclopropylmethoxy-5-(4-fluoro-phenyl)-N-(2-hydroxy-cyclohexylmethyl)-nicotinamide 6-Cyclopropylmethoxy-5-(4-fluoro-phenyl)-nicotinic acid (0.50 g, 2 mmol) was dissolved in DMF (20 mL). To the solution was added TBTU (0.62 g, 2 mmol), N,N-diisopropylethyl amine (1.5 mL, 9 mmol) and cis-2-aminomethyl-1-cyclohexanol (317 mg, 2 mmol). The reaction mixture was stirred for 18 h at room temperature. The solvent was evaporated in vacuo and the residue was purified by column chromatography on silica (n-heptane/ethyl acetate gradient) to yield 585 mg of the title compound as a colorless solid, MS (ISP) 399.2 (M+H)$^+$.

(−)-cis-6-Cyclopropylmethoxy-5-(4-fluoro-phenyl)-N-(2-hydroxy-cyclohexylmethyl)-nicotinamide Chiral separation of cis-6-cyclopropylmethoxy-5-(4-fluoro-phenyl)-N-(2-hydroxy-cyclohexylmethyl)-nicotinamide with heptane/ethanol on ChiralpakAD® yielded the (−)-enantiomer, MS (ISP) 399.2 (M+H)$^+$, $\alpha_D^{20}$: −16.7° in MeOH.

Example 76

(−)-cis-5-(4-Chloro-phenyl)-N-(2-hydroxy-cyclohexylmethyl)-6-(2-methoxy-ethoxy)-nicotinamide The title compound was synthesized in analogy to Example 75, using 5-bromo-6-chloro-3-pyridinecarboxylic acid, 2-methoxyethanol, (4-chloro-phenyl)-boronic acid and cis-2-aminomethyl-1-cyclohexanol as starting materials to yield racemic cis-5-(4-chloro-phenyl)-N-(2-hydroxy-cyclohexylmethyl)-6-(2-methoxy-ethoxy)-nicotinamide. Separation with heptane/ethanol on ChiralpakAD® yielded the (−)-enantiomer, MS (ISP) 419.1 (M+H)$^+$, $\alpha_D^{20}$: −16.6° in MeOH.

Example 77

(−)-6-Cyclopropylmethoxy-5-(4-fluoro-phenyl)-N-(2-hydroxymethyl-butyl)-nicotinamide The title compound was synthesized in analogy to Example 75, using 5-bromo-6-chloro-3-pyridinecarboxylic acid, cyclopropanemethanol, (4-fluoro-phenyl)-boronic acid and 2-aminomethyl-1-butanol as starting materials to yield racemic 6-cyclopropylmethoxy-5-(4-fluoro-phenyl)-N-(2-hydroxymethyl-butyl)-nicotinamide. Separation with heptane/ethanol on ChiralpakAD® yielded the (−)-enantiomer, MS (ISP) 373.2 (M+H)$^+$, $\alpha_D^{20}$: −4.9° in MeOH.

Example 78

(−)-cis-5-(4-Fluoro-phenyl)-N-(2-hydroxy-cyclohexylmethyl)-6-(2-methoxy-ethoxy)-nicotinamide The title compound was synthesized in analogy to Example 75, using 5-bromo-6-chloro-3-pyridinecarboxylic acid, 2-methoxyethanol, (4-fluoro-phenyl)-boronic acid and cis-2-aminomethyl-1-cyclohexanol as starting materials to yield racemic cis-5-(4-fluoro-phenyl)-N-(2-hydroxy-cyclohexylmethyl)-6-(2-methoxy-ethoxy)-nicotinamide. Separation with heptane/ethanol on ChiralpakAD® yielded the (−)-enantiomer, MS (ISP) 403.4 (M+H)$^+$, $\alpha_D^{20}$: −17.1° in MeOH.

Example 79

5-(4-Chloro-phenyl)-6-(cyclopropylmethyl-methyl-amino)-N-((1R,2R)-2-hydroxy-cyclohexyl)-nicotinamide The title compound was synthesized in analogy to Example 74, using 5-bromo-6-chloro-nicotinic acid methyl ester, cyclopropylmethyl methylamine hydrochloride, (4-chloro-phenyl)-boronic acid and (1R,2R)-2-amino-cyclohexanol hydrochloride as starting materials to yield 5-(4-chloro-phenyl)-6-(cyclopropylmethyl-methyl-amino)-N-((1R,2R)-2-hydroxy-cyclohexyl)-nicotinamide. MS (ISP) 414.3 (M+H)$^+$.

Example 80

5-(4-Chloro-phenyl)-6-(cyclopropylmethyl-methyl-amino)-N-((1RS,2RS)-2-hydroxy-cyclohexylmethyl)-nicotinamide The title compound was synthesized in analogy to Example 74, using 5-bromo-6-chloro-nicotinic acid methyl ester, cyclopropylmethyl methylamine hydrochloride, (4-chloro-phenyl)-boronic acid and cis-2-aminomethyl-1-cyclohexanol hydrochloride as starting materials to yield 5-(4-chloro-phenyl)-6-(cyclopropylmethyl-methyl-amino)-N-((1RS,2RS)-2-hydroxy-cyclohexylmethyl)-nicotinamide. MS (ISP) 428.1 (M+H)$^+$.

Example 81

6-(Cyclopropylmethyl-methyl-amino)-5-(4-fluoro-phenyl)-N-((1R,2R)-2-hydroxy-cyclohexyl)-nicotinamide The title compound was synthesized in analogy to Example 74, using 5-bromo-6-chloro-nicotinic acid methyl ester, cyclopropylmethyl methylamine hydrochloride, (4-fluoro-phenyl)-boronic acid and (1R,2R)-2-amino-cyclohexanol hydrochloride as starting materials to yield 6-(cyclopropylmethyl-methyl-amino)-5-(4-fluoro-phenyl)-N-((1R,2R)-2-hydroxy-cyclohexyl)-nicotinamide. MS (ISP) 398.3 (M+H)$^+$.

Example 82

6-(Cyclopropylmethyl-methyl-amino)-5-(4-fluoro-phenyl)-N-((1RS,2RS)-2-hydroxy-cyclohexylmethyl)-nicotinamide The title compound was synthesized in analogy to Example 74, using 5-bromo-6-chloro-nicotinic acid methyl ester, cyclopropylmethyl methylamine hydrochloride, (4-fluoro-phenyl)-boronic acid and cis-2-aminomethyl-1-cyclohexanol hydrochloride as starting materials to yield racemic 6-(cyclopropylmethyl-methyl-amino)-5-(4-fluoro-phenyl)-N-((1RS,2RS)-2-hydroxy-cyclohexylmethyl)-nicotinamide. MS (ISP) 412.1 (M+H)$^+$.

Example 83

5-(4-Chloro-phenyl)-N-(2-cyclopropyl-2-hydroxy-propyl)-6-(3-methyl-isoxazol-5-ylmethoxy)-nicotinamide The title compound was synthesized in analogy to Example 75, using 5-bromo-6-chloro-3-pyridinecarboxylic acid, 3-methyl-5-isoxazolemethanol, (4-chloro-phenyl)-boronic acid and x-(aminomethyl)-α-methyl-cyclopropanemethanol as starting materials to yield 5-(4-chloro-phenyl)-N-(2-cyclopropyl-2-hydroxy-propyl)-6-(3-methyl-isoxazol-5-ylmethoxy)-nicotinamide, MS (ISP) 442.4 (M+H)$^+$.

Example 84

5-(4-Chloro-phenyl)-N-((1R,2R)-2-hydroxy-cyclohexyl)-6-(3-methyl-isoxazol-5-ylmethoxy)-nicotinamide The title compound was synthesized in analogy to Example 75, using 5-bromo-6-chloro-3-pyridinecarboxylic acid, 3-methyl-5-isoxazolemethanol, (4-chloro-phenyl)-boronic acid and (1R,2R)-2-amino-cyclohexanol as starting materials to yield 5-(4-chloro-phenyl)-N-((1R,2R)-2-hydroxy-cyclohexyl)-6-(3-methyl-isoxazol-5-ylmethoxy)-nicotinamide, MS (ISP) 442.4, 444.4 (M+H)$^+$.

Example 85 cis-5-(4-Chloro-phenyl)-N-(2-hydroxy-cyclohexylmethyl)-6-(3-methyl-isoxazol-5-ylmethoxy)-nicotinamide The title compound was synthesized in analogy to Example 75, using 5-bromo-6-chloro-3-pyridinecarboxylic acid, 3-methyl-5-isoxazolemethanol, (4-chloro-phenyl)-boronic acid and cis-2-aminomethyl-1-cyclohexanol as starting materials to yield racemic cis-5-(4-fluoro-phenyl)-N-(2-hydroxy-cyclohexylmethyl)-6-(2-methoxy-ethoxy)-nicotinamide, MS (ISP) 456.2 (M+H)$^+$.

Example 86

5-(4-Chloro-phenyl)-N-(2-hydroxymethyl-butyl)-6-(3-methyl-isoxazol-5-ylmethoxy)-nicotinamide The title compound was synthesized in analogy to Example 75, using 5-bromo-6-chloro-3-pyridinecarboxylic acid, 3-methyl-5-isoxazolemethanol, (4-chloro-phenyl)-boronic acid and 2-aminomethyl-1-butanol as starting materials to yield racemic 5-(4-chloro-phenyl)-N-(2-hydroxymethyl-butyl)-6-(3-methyl-isoxazol-5-ylmethoxy)-nicotinamide, MS (ISP) 430.3 (M+H)$^+$.

Example 87

N-((R)-2-Cyclopropyl-2-hydroxy-propyl)-6-cyclopropylmethoxy-5-(4-trifluoromethyl-phenyl)-nicotinamide and Example 88

N-((S)-2-Cyclopropyl-2-hydroxy-propyl)-6-cyclopropylmethoxy-5-(4-trifluoromethyl-phenyl)-nicotinamide The two title compounds were synthesized in analogy to the procedure described for the preparation of Example 23, using 5-bromo-6-chloro-nicotinic acid methyl ester, cyclopropylmethanol (commercially available), 4-trifluoromethylphenylboronic acid (commercially available) and 2-cyclopropyl-2-hydroxy-propylamine (commercially available) as starting materials and separated into the two enantiomers by column chromatography on chiral phase.

Example 87; MS (m/e): 435.5 (MH$^+$).

Example 88; MS (m/e): 435.3 (MH$^+$).

Example 89

6-Cyclopropylmethoxy-N-((1RS,2RS)-2-hydroxy-cyclohexylmethyl)-5-(4-trifluoromethoxy-phenyl)-nicotinamide The title compound was synthesized in analogy to Example 75, using 5-bromo-6-chloro-3-pyridinecarboxylic acid, hydroxymethyl-cyclopropan, 4-(trifluoromethoxy) phenylboronic acid and cis-2-aminomethyl-1-cyclohexanol hydrochloride as starting materials to yield racemic 6-cyclopropylmethoxy-N-((1RS,2RS)-2-hydroxy-cyclohexylmethyl)-5-(4-trifluoromethoxy-phenyl)-nicotinamide. MS (ISP) 465.3 (M+H)$^+$.

Example 90

(RS)-N-(2-Cyclopropyl-2-hydroxy-propyl)-6-cyclopropylmethoxy-5-(4-trifluoromethoxy-phenyl)-nicotinamide The title compound was synthesized in analogy to Example 75, using 5-bromo-6-chloro-3-pyridinecarboxylic acid, hydroxymethyl-cyclopropan, 4-(trifluoromethoxy)-phenylboronic acid and 1-amino-2-cyclopropyl-propan-2-ol as starting materials to yield (RS)-N-(2-cyclopropyl-2-hydroxy-propyl)-6-cyclopropylmethoxy-5-(4-trifluoro-methoxy-phenyl)-nicotinamide. MS (ISP) 451.3 (M+H)$^+$.

Example 91

6-Cyclopropylmethoxy-N-((1R,2R)-2-hydroxy-cyclohexyl)-5-(4-trifluoromethoxy-phenyl)-nicotinamide The title compound was synthesized in analogy to Example 75, using 5-bromo-6-chloro-3-pyridinecarboxylic acid, hydroxymethyl-cyclopropan, 4-(trifluoromethoxy)-phenylboronic acid and (1R,2R)-2-amino-cyclohexanol hydrochloride as starting materials to yield 6-cyclopropylmethoxy-N-((1R,2R)-2-hydroxy-cyclohexyl)-5-(4-trifluoromethoxy-phenyl)-nicotinamide. MS (ISP) 451.1 (M+H)$^+$.

Example 92

5-(4-Chloro-phenyl)-N-((1R,2R)-2-hydroxy-cyclohexyl)-6-(methyl-propyl-amino)-nicotinamide The title compound was synthesized in analogy to Example 74, using 5-bromo-6-chloro-nicotinic acid methyl ester, N-methyl-N-propylamine, (4-chloro-phenyl)-boronic acid and (1R,2R)-2-amino-cyclohexanol hydrochloride as starting materials to yield 5-(4-chloro-phenyl)-N-((1R,2R)-2-hydroxy-cyclohexyl)-6-(methyl-propyl-amino)-nicotinamide. MS (ISP) 402.3 (M+H)$^+$.

Example 93

5-(4-Chloro-phenyl)-N-(2-cyclopropyl-2-hydroxy-propyl)-6-(pyridin-2-ylmethoxy)-nicotinamide The title compound was synthesized in analogy to Example 75, using 5-bromo-6-chloro-3-pyridinecarboxylic acid, 2-pyridinemethanol, (4-chloro-phenyl)-boronic acid and α-(aminomethyl)-α-methyl-cyclopropanemethanol as starting materials to yield racemic 5-(4-chloro-phenyl)-N-(2-cyclopropyl-2-hydroxy-propyl)-6-(pyridin-2-ylmethoxy)-nicotinamide, MS (ISP) 438.1 (M+H)$^+$.

Example 94

(−)-cis-6-Cyclopropylmethoxy-N-((2-hydroxy-cyclohexylmethyl)-5-(4-trifluoromethoxy-phenyl)-nicotinamide Separation of the enantiomers of 6-cyclopropylmethoxy-N-((1RS,2RS)-2-hydroxy-cyclohexylmethyl)-5-(4-trifluoromethoxy-phenyl)-nicotinamide (example 89) with heptane/ethanol on ChiralpakAD® yielded the (−)-enantiomer. MS (ISP) 465.3 (M+H)$^+$.

Example 95

N-((R)-2-Cyclopropyl-2-hydroxy-propyl)-6-(2-methoxy-ethoxy)-5-(4-trifluoromethyl-phenyl)-nicotinamide The title compounds was synthesized in analogy to the procedure described for the preparation of Example 23, using 5-bromo-6-chloro-nicotinic acid methyl ester, methoxyethanol (commercially available), 4-trifluoromethylphenylboronic acid (commercially available) and 2-cyclopropyl-2-hydroxy-propylamine (commercially available) as starting materials. The two enantiomers were separated by column chromatography on chiral phase. MS (m/e): 439 (MH$^+$).

Example 96

5-(4-Fluoro-phenyl)-N-((1R,2R)-2-hydroxy-cyclohexyl)-6-(methyl-propyl-amino)-nicotinamide The title compound was synthesized in analogy to Example 74, using 5-bromo-6-chloro-nicotinic acid methyl ester, N-methyl-N-propylamine, (4-fluoro-phenyl)-boronic acid and (1R,2R)-2-amino-cyclohexanol hydrochloride as starting materials to yield 5-(4-fluoro-phenyl)-N-((1R,2R)-2-hydroxy-cyclohexyl)-6-(methyl-propyl-amino)-nicotinamide. MS (ISP) 386.2 (M+H)$^+$.

Example 97

N-((R)-2-Cyclopropyl-2-hydroxy-propyl)-5-(4-fluoro-phenyl)-6-(2-methoxy-ethoxy)-nicotinamide The title compounds was synthesized in analogy to the procedure described for the preparation of Example 23, using 5-bromo-6-chloro-nicotinic acid methyl ester, methoxyethanol (commercially available), 4-fluorophenylboronic acid (commercially available) and 2-cyclopropyl-2-hydroxy-propylamine (commercially available) as starting materials. The two enantiomers were separated by column chromatography on chiral phase. MS (m/e): 389.3 (MH$^+$).

Example 98

N-((R)-2-Cyclopropyl-2-hydroxy-propyl)-6-cyclopropylmethoxy-5-(4-fluoro-phenyl)-nicotinamide The title compound was synthesized in analogy to the procedure described for the preparation of Example 23, using 5-bromo-6-chloro-nicotinic acid methyl ester, cyclopropylmethanol (commercially available), 4-fluorophenyl-boronic acid (commercially available) and 2-cyclopropyl-2-hydroxy-propylamine (commercially available) as starting materials. The two enantiomers were separated by column chromatography on chiral phase. MS (m/e): 385.3 (MH$^+$).

Example 99

3'-(4-Chloro-phenyl)-3,4,5,6-tetrahydro-2H-[1,2'] bipyridinyl-5'-carboxylic acid ((1R,2R)-2-hydroxy-cyclohexyl)-amide The title compound was synthesized in analogy to Example 74, using 5-bromo-6-chloro-nicotinic acid methyl ester, piperidine, (4-chloro-phenyl)-boronic acid and (1R, 2R)-2-amino-cyclohexanol hydrochloride as starting materials to yield 3'-(4-chloro-phenyl)-3,4,5,6-tetrahydro-2H-[1, 2']bipyridinyl-5'-carboxylic acid ((1R,2R)-2-hydroxy-cyclohexyl)-amide. MS (ISP) 414.4 (M+H)$^+$.

Example 100

5-(4-Chloro-phenyl)-N-((S)-2-cyclopropyl-2-hydroxy-propyl)-6-(3-methyl-isoxazol-5-ylmethoxy)-nicotinamide

2-Cyclopropyl-2-trimethylsilanyloxy-propionitrile

To a well stirred mixture of cyclopropylmethylketone (27.8 mL, 0.3 mol), trimethylsilylcyanide (55.8 mL, 0.45 mol) and 18-crown-6 (4.87 g, 18.5 mmol) was added potassium cyanide (2.44 g, 37.5 mmol). The temperature rose to ~100° C. and stirring was continued for 1 h with heating to 145° C. After cooling the mixture was purified by silicagel chromatography (500 g silica, heptane/ethylacetate 6:1) to yield 47.1 g of the title compound as light brown oil, $^1$H NMR(CDCl$_3$): 0.23 (s, 9H), 0.56 (m, 4H), 1.17 (m, 1H), 1.63 (s, 3H, CH$_3$).

α-(Acetyloxy)-α-methyl-cyclopropaneacetonitrile

To a well stirred and ice-cooled solution of 2-cyclopropyl-2-trimethylsilanyloxy-propionitrile (188.5 g, 1.03 mol) in acetonitrile (1000 mL) was added acetic anhydride (194 mL, 2.06 mol) and scandium trifluoromethanesulfonate (5 g, 10.3 mmol). The temperature rose to ~10° C. and stirring was continued for 15' at room temperature. The solvent was evaporated in vacuo and the residue was distilled to yield 138 g of the title compound as colorless liquid, bp: 84–86° C./6 mbar.

(S)-α-(Acetyloxy)-α-methyl-cyclopropaneacetonitrile (Warning: Highly toxic hydrogen cyanide is formed in the experiment; use adequate protection). 111.1 g (725 mmol) racemic α-(acetyloxy)-α-methyl-cyclopropaneacetonitrile was emulsified in 6.0 L of 0.1 M sodium chloride/3.8 mM sodium phosphate buffer pH 7.0 by stirring. The emulsion was cooled to 10° C. and the hydrolytic reaction started by adding 6.0 g of cholesterase from Candida cylindraceae (Roche Applied Sciences; Cat. No. 10129046) and the pH maintained at 7.0 by the controlled addition of 1.0 N sodium hydroxide solution under vigorous stirring. After a consumption of 618.3 mL solution (corresponding to 85% conversion) the reaction was stopped by adding 5 L dichloromethane under vigorous stirring. The emulsion was allowed to stand for phase separation. The organic phase was removed (the turbid part was filtered through silicon-treated Phase Separator (1PS; Whatman) and the filtrate stirred with ca. 1 L of Speedex filter aid). The aqueous phase was extracted again with 2×5 L dichloromethane. The combined organic phases were concentrated in vacuo down to a volume of ca. 40 mL and distilled (finally ca. 69–70° C./4 mbar) to give 13.70 g (89 mmol; 12%) of (S)-α-(acetyloxy)-α-methyl-cyclopropaneacetonitrile as a colorless oil. Analysis: >99% GC; 96.8% ee (column: BGB-176; 30 m×0.25 mm; 100–140° C. with 2° C./min; H$_2$; 90 kPa; Inj. 200° C.; Det. 210° C.); α$_D^{20}$: –31.61° (c=1.00; EtOH); EI-MS: 154.1 (M+H$^+$).

(S)-α-(aminomethyl)-α-methyl-cyclopropanemethanol

To a well stirred and ice-cooled suspension of lithium aluminiumhydride (10.1 g, 0.266 mol) in THF (250 mL) was added a solution of (S)-α-(acetyloxy)-α-methyl-cyclopropaneacetonitrile (13.6 g, 89 mmol) in THF (50 mL) so that the temperature of the cooled reaction mixture did not rise above 30° C. Once the addition was finished the mixture was refluxed for 2 h with stirring and over night at room temperature. The mixture was cooled and surplus lithium aluminiumhydride was destroyed by sequential addition of water (17 mL); sodium hydroxide solution (15%; 34 mL) and water (51 mL). The mixture was diluted with THF (150 mL), dried with Na2SO4, filtered and evaporated in vacuo. The residue was distilled to yield 4.4 g of the title compound as colorless oil, bp: 69-70° C./7 mbar, α$_D^{20}$:–13.32° (MeOH).

5-(4-Chloro-phenyl)-N-((S)-2-cyclopropyl-2-hydroxy-propyl)-6-(3-methyl-isoxazol-5-ylmethoxy)-nicotinamide The title compound was synthesized in analogy to Example 75, using 5-bromo-6-chloro-3-pyridinecarboxylic acid, 3-methyl-5-isoxazolemethanol, (4-chloro-phenyl)-boronic acid and (S)-α-(aminomethyl)-α-methyl-cyclopropanemethanol as starting materials to yield 5-(4-chloro-phenyl)-N-((S)-2-cyclopropyl-2-hydroxy-propyl)-6-(3-methyl-isoxazol-5-ylmethoxy)-nicotinamide, MS (ISP) 442.1 (M+H)$^+$.

Example 101

(–)-N-(2-Cyclopropyl-2-hydroxy-propyl)-6-cyclopropylmethoxy-5-(4-trifluoromethoxy-phenyl)-nicotinamide Separation of the enantiomers of N-(2-cyclopropyl-2-hydroxy-propyl)-6-cyclopropylmethoxy-5-(4-trifluoromethoxy-phenyl)-nicotinamide (example 90) with heptane/ethanol on a ChiralpakAD® column yielded the (–)-enantiomer. MS (ISP) 451.1 (M+H)$^+$.

Example 102

5-(4-Chloro-phenyl)-N-((1R,2R)-2-hydroxy-cyclohexyl)-6-(1-methyl-1H-imidazol-2-ylmethoxy)-nicotinamide

5-Bromo-6-(1-methyl-1H-imidazol-2-ylmethoxy)-nicotinic acid methyl ester

5-Bromo-6-hydroxy-3-pyridinecarboxylic acid methyl ester (1.0 g, 4.3 mmol) was suspended in tetrahydrofurane, 1-methyl-1H-imidazole-2-methanol (0.72 g, 6.5 mmol) and triphenylphosphine was added (1.70 g, 6.5 mmol). To this mixture was added with stirring diisopropyl-azodicarboxylate (1.35 mL, 6.5 mmol) at room temperature. Stirring was continued for 1 h at room temperature, solvent was removed and the residue was purified by chromatography with heptane/ethylacetate/methanol on silica gel to yield 0.38 g of the title compound as a colorless solid, MS (ISP) 326.0, 328.0 (M+H)$^+$.

5-(4-Chloro-phenyl)-6-(1-methyl-1H-imidazol-2-ylmethoxy)-nicotinic acid methyl ester 5-Bromo-6-(1-methyl-1H-imidazol-2-ylmethoxy)-nicotinic acid methyl ester (0.35 g, 1.1 mmol) was dissolved in toluene (6 mL). To this solution was added (4-chloro-phenyl)-boronic acid (0.17 g, 1.1 mmol), [1,1'-bis(diphenylphosphino)ferrocene]dichloropalladium(II) dichloromethane complex (43 mg), and 2 N sodium carbonate solution (2 mL). The whole mixture was heated with stirring at 90° C. for 18 h, cooled to room temperature and eluted with ethyl acetate over 10 g ChemElut (Varian). The solvent was evaporated and the residue was purified by column chromatography on silica (n-heptane/ethyl acetate gradient) to yield 0.29 g of the title compound as an off-white solid, MS (ISP) 358.1 (M+H)$^+$.

5-(4-Chloro-phenyl)-6-(1-methyl-1H-imidazol-2-ylmethoxy)-nicotinic acid 5-(4-Chloro-phenyl)-6-(1-methyl-1H-imidazol-2-ylmethoxy)-nicotinic acid methyl ester (0.28 g, 0.8 mmol) was dissolved in tetrahydrofuran (4.5 mL). Water (1.5 mL) and lithium hydroxide (99 mg, 2.3 mmol) was added and the mixture was stirred for 1 h at 80° C. The mixture was cooled to room temperature; citric acid (4 mL, 10%) was added and the mixture was extracted with ethyl acetate. Organic phases were pooled dried with $Na_2SO_4$ and the solvent evaporated to give a quantitative yield of the title compound as beige solid, MS (ISP) 342.0 (M–H)$^-$.

5-(4-Chloro-phenyl)-N-((1R,2R)-2-hydroxy-cyclohexyl)-6-(1-methyl-1H-imidazol-2-ylmethoxy)-nicotinamide The title compound was synthesized in analogy to Example 75 c, using 5-(4-chloro-phenyl)-6-(1-methyl-1H-imidazol-2-ylmethoxy)-nicotinic acid and ((1R,2R)-2-amino-1-cyclohexanol as starting materials to yield 5-(4-chloro-phenyl)-N-((1R,2R)-2-hydroxy-cyclohexyl)-6-(1-methyl-1H-imidazol-2-ylmethoxy)-nicotinamide, MS (ISP) 441.2 (M+H)$^+$.

Example 103

6-Cyclopropylmethoxy-N-((1RS,2RS)-2-hydroxy-cyclohexylmethyl)-5-(4-trifluoro-methyl-phenyl)-nicotinamide The title compound was synthesized in analogy to Example 75, using 5-bromo-6-chloro-3-pyridinecarboxylic acid, hydroxymethyl-cyclopropan, 4-(trifluoromethyl)-phenylboronic acid and cis-2-aminomethyl-1-cyclohexanol hydrochloride as starting materials to yield racemic 6-cyclopropylmethoxy-N-((1RS,2RS)-2-hydroxy-cyclohexylmethyl)-5-(4-trifluoromethyl-phenyl)-nicotinamide. MS (ISP) 449.1 (M+H)$^+$.

Example 104

5-(4-Chloro-phenyl)-N-((1R,2R)-2-hydroxy-cyclohexyl)-6-(2-methyl-2H-[1,2,4]triazol-3-ylmethoxy)-nicotinamide The title compound was synthesized in analogy to Example 75, using 5-bromo-6-chloro-3-pyridinecarboxylic acid, 1-methyl-1H-1,2,4-triazole-5-methanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(2-methyl-2H-[1,2,4]triazol-3-ylmethoxy)-nicotinamide, MS (ISP) 442.1 (M+H)$^+$.

Example 105 cis-5-(4-Chloro-phenyl)-N-(2-hydroxy-cyclohexylmethyl)-6-(2-methyl-2H-[1,2,4]triazol-3-ylmethoxy)-nicotinamide The title compound was synthesized in analogy to Example 75, using 5-bromo-6-chloro-3-pyridinecarboxylic acid, 1-methyl-1H-1,2,4-triazole-5-methanol, (4-chloro-phenyl)-boronic acid and cis-2-aminomethyl-1-cyclohexanol as starting materials to yield racemic cis-5-(4-chloro-phenyl)-N-(2-hydroxy-cyclohexylmethyl)-6-(2-methyl-2H-[1,2,4]triazol-3-ylmethoxy)-nicotinamide, MS (ISP) 456.3 (M+H)$^+$.

Example 106 cis-5-(4-Chloro-phenyl)-N-(2-hydroxy-cyclohexylmethyl)-6-(1-methyl-1H-imidazol-2-ylmethoxy)-nicotinamide The title compound was synthesized in analogy to Example 102, using 5-bromo-6-chloro-3-pyridinecarboxylic acid methyl ester, 1-methyl-1H-imidazole-2-methanol, (4-chloro-phenyl)-boronic acid and cis-2-aminomethyl-1-cyclohexanol as starting materials to yield racemic cis-5-(4-chloro-phenyl)-N-(2-hydroxy-cyclohexylmethyl)-6-(1-methyl-1H-imidazol-2-ylmethoxy)-nicotinamide, MS (ISP) 455.3 (M+H)$^+$.

Example 107 cis-5-(4-Chloro-phenyl)-N-(2-hydroxy-cyclohexylmethyl)-6-(pyrimidin-2-ylmethoxy)-nicotinamide The title compound was synthesized in analogy to Example 75, using 5-bromo-6-chloro-3-pyridinecarboxylic acid, 2-pyrimidinemethanol, (4-chloro-phenyl)-boronic acid and cis-2-aminomethyl-1-cyclohexanol as starting materials to yield racemic cis-5-(4-chloro-phenyl)-N-(2-hydroxy-cyclohexylmethyl)-6-(pyrimidin-2-ylmethoxy)-nicotinamide, MS (ISP) 453.2 (M+H)$^+$.

Example 108

5-(4-Chloro-phenyl)-N-(2-hydroxymethyl-butyl)-6-(pyrimidin-2-ylmethoxy)-nicotinamide The title compound was synthesized in analogy to Example 75, using 5-bromo-6-chloro-3-pyridinecarboxylic acid, 2-pyrimidinemethanol, (4-chloro-phenyl)-boronic acid and 2-aminomethyl-1-butanol as starting materials to yield racemic 5-(4-chloro-phenyl)-N-(2-hydroxymethyl-butyl)-6-(pyrimidin-2-ylmethoxy)-nicotinamide, MS (ISP) 427.2 (M+H)$^+$.

Example 109

(–)-cis-6-Cyclopropylmethoxy-N-(2-hydroxy-cyclohexylmethyl)-5-(4-trifluoromethyl-phenyl)-nicotinamide Separation of the enantiomers of 6-cyclopropylmethoxy-N-((1RS,2RS)-2-hydroxy-cyclohexylmethyl)-5-(4-trifluoromethyl-phenyl)-nicotinamide (example 103) with heptane/ethanol on ChiralpakAD® yielded the (–)-enantiomer. MS (ISP) 449.1 (M+H)$^+$.

Example 110

5-(4-Cyano-phenyl)-6-cyclopropylmethoxy-N-((1RS,2RS)-2-hydroxy-cyclohexyl-methyl)-nicotinamide The title compound was synthesized in analogy to Example 75, using 5-bromo-6-chloro-3-pyridinecarboxylic acid, hydroxymethyl-cyclopropan, 4-cyanophenylboronic acid and cis-2-aminomethyl-1-cyclohexanol hydrochloride as starting materials to yield racemic 5-(4-cyano-phenyl)-6-cyclopropylmethoxy-N-((1RS,2RS)-2-hydroxy-cyclohexyl-methyl)-nicotinamide. MS (ISP) 406.3 (M+H)$^+$.

Example 111

5-(4-Chloro-phenyl)-N-((1R,2R)-2-hydroxy-cyclohexyl)-6-(pyrimidin-2-ylmethoxy)-nicotinamide The title compound was synthesized in analogy to Example 75, using 5-bromo-6-chloro-3-pyridinecarboxylic acid, 2-pyrimidinemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(pyrimidin-2-ylmethoxy)-nicotinamide, MS (ISP) 439.1 (M+H)$^+$.

Example 112

5-(4-Chloro-phenyl)-N-((1R,2R)-2-hydroxy-cyclohexyl)-6-(pyridin-4-ylmethoxy)-nicotinamide The title compound was synthesized in analogy to Example 75, using 5-bromo-6-chloro-3-pyridinecarboxylic acid, 4-pyridinemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(pyridin-4-ylmethoxy)-nicotinamide, MS (ISP) 438.1 (M+H)$^+$.

Example 113 cis-5-(4-Chloro-phenyl)-N-(2-hydroxy-cyclohexylmethyl)-6-(pyridin-4-ylmethoxy)-nicotinamide The title compound was synthesized in analogy to Example 75, using 5-bromo-6-chloro-3-pyridinecarboxylic acid, 4-pyridinemethanol, (4-chloro-phenyl)-boronic acid and cis-2-aminomethyl-1-cyclohexanol as starting materials to yield cis-5-(4-chloro-phenyl)-N-(2-hydroxy-cyclohexylmethyl)-6-(pyridin-4-ylmethoxy)-nicotinamide, MS (ISP) 452.1 (M+H)$^+$.

Example 114

5-(4-Chloro-phenyl)-N-(2-hydroxymethyl-butyl)-6-(pyridin-4-ylmethoxy)-nicotinamide The title compound was synthesized in analogy to Example 75, using 5-bromo-6-chloro-3-pyridinecarboxylic acid, 4-pyridinemethanol, (4-chloro-phenyl)-boronic acid and 2-aminomethyl-1-butanol as starting materials to yield racemic 5-(4-chloro-phenyl)-N-(2-hydroxymethyl-butyl)-6-(pyridin-4-ylmethoxy)-nicotinamide, MS (ISP) 426.1 (M+H)$^+$.

Example 115

(RS)-5-(4-Cyano-phenyl)-6-cyclopropylmethoxy-N-(2-hydroxymethyl-butyl)-nicotinamide The title compound was synthesized in analogy to Example 75, using 5-bromo-6-chloro-3-pyridinecarboxylic acid, hydroxymethyl-cyclopropan, 4-cyanophenylboronic acid and 2-(aminomethyl)-1-butanol as starting materials to yield (RS)-5-(4-cyano-phenyl)-6-cyclopropylmethoxy-N-(2-hydroxymethyl-butyl)-nicotinamide. MS (ISP) 380.2 (M+H)$^+$.

Example 116

5-(4-Chloro-phenyl)-N-((R)-2-cyclopropyl-2-hydroxy-propyl)-6-cyclopropylmethoxy-nicotinamide (R)-α-(Acetyloxy)-α-methyl-cyclopropaneacetonitrile (Warning: Highly toxic hydrogen cyanide is formed in the experiment; use adequate protection). 119.8 g (782 mmol) racemic α-(acetyloxy)-α-methyl-cyclopropaneacetonitrile was emulsified in 7.0 L 0.1 M sodium chloride/3.8 mM sodium phosphate buffer pH 7.0 by stirring. The emulsion was cooled to 10° C. and the hydrolytic reaction started by adding 8.0 g of triacylglycerol lipase from wheat germ (Sigma L-3001) and the pH maintained at 7.0 by the controlled addition of 1.0 N sodium hydroxide solution under vigorous stirring at 10° C. After a consumption of 605.8 mL solution (corresponding to 78% conversion), after 118 h, the reaction was stopped by adding 6 L dichloromethane under vigorous stirring. The emulsion was allowed to stand overnight for phase separation. The organic phase was removed (the turbid part was filtered through silicon-treated Phase Separator (1 PS; Whatman) and the filtrate stirred with ca. 1 L of Speedex filter aid). The aqueous phase was extracted again with 2×6 L dichloromethane. The combined organic phases were concentrated in vacuo down to a volume of ca. 40 mL and distilled (final temp. 68–69° C./4 mbar) to give 17.88 g (117 mmol; 15%) of (R)-α-(acetyloxy)-α-methyl-cyclopropaneacetonitrile as a colorless oil. Analysis: purity >99% GC; 98.0% ee (column: BGB-176; 30 m×0.25 mm; 100–140° C. with 2° C./min; H$_2$; 90 kPa; Inj. 200° C.; Det. 210° C.); $\alpha_D^{20}$:+32.92° (c=1.00; EtOH).

(R)-α-(aminomethyl)-α-methyl-cyclopropanemethanol

The title compound was synthesized in analogy to Example 100 d, using (R)-α-(acetyloxy)-α-methyl-cyclopropaneacetonitrile as starting material to yield the title compound as colorless oil, bp: 70–72° C./7 mbar, $\alpha_D^{20}$:+12.09° (MeOH).

5-(4-Chloro-phenyl)-N-((R)-2-cyclopropyl-2-hydroxy-propyl)-6-cyclopropylmethoxy-nicotinamide The title compound was synthesized in analogy to Example 75, using 5-bromo-6-chloro-3-pyridinecarboxylic acid, cyclopropanemethanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-cyclopropyl-methoxy-nicotinamide, MS (ISP) 401.3 (M+H)$^+$.

Example 117

5-(4-Chloro-phenyl)-N-((R)-2-cyclopropyl-2-hydroxy-propyl)-6-(3-methyl-isoxazol-5-ylmethoxy)-nicotinamide The title compound was synthesized in analogy to Example 75, using 5-bromo-6-chloro-3-pyridinecarboxylic acid, 3-methyl-5-isoxazolemethanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-(3-methyl-isoxazol-5-ylmethoxy)-nicotinamide, MS (ISP) 442.1 (M+H)$^+$.

Example 118

(RS)-6-Cyclopropylmethoxy-N-(2-hydroxymethyl-butyl)-5-(4-trifluoromethoxy-phenyl)-nicotinamide The title compound was synthesized in analogy to Example 75, using 5-bromo-6-chloro-3-pyridinecarboxylic acid, hydroxymethyl-cyclopropan, 4-trifluoromethoxy-phenylboronic acid and 2-(aminomethyl)-1-butanol as starting materials to yield (RS)-6-cyclopropylmethoxy-N-(2-hydroxymethyl-butyl)-5-(4-trifluoromethoxy-phenyl)-nicotinamide. M0S (ISP) 439.0 (M+H)$^+$

Example 119

(RS)-6-Cyclopropylmethoxy-N-(2-hydroxymethyl-butyl)-5-(4-trifluoromethyl-phenyl)-nicotinamide The title compound was synthesized in analogy to Example 75, using 5-bromo-6-chloro-3-pyridinecarboxylic acid, hydroxymethyl-cyclopropan, 4-trifluoromethyl-phenylboronic acid and 2-(aminomethyl)-1-butanol as starting materials to yield (RS)-6-cyclopropylmethoxy-N-(2-hydroxymethyl-butyl)-5-(4-trifluoromethyl-phenyl)-nicotinamide. MS (ISP) 423.3 (M+H)$^+$

Example 120

(−)-6-Cyclopropylmethoxy-N-(2-hydroxymethyl-butyl)-5-(4-trifluoromethyl-phenyl)-nicotinamide Separation of the enantiomers of 6-cyclopropylmethoxy-N-(2-hydroxymethyl-butyl)-5-(4-trifluoromethyl-phenyl)-nicotinamide (example 119) with heptane/ethanol on ChiralpakAD® yielded the (−)-enantiomer. MS (ISP) 423.0 (M+H)$^+$, $\alpha_D^{20}$: −3.5° in MeOH.

Example 121

(−)-cis-5-(4-Cyano-phenyl)-6-cyclopropylmethoxy-N-(2-hydroxy-cyclohexylmethyl)-nicotinamide Separation of the enantiomers of 5-(4-cyano-phenyl)-6-cyclopropylmethoxy-N-((1RS,2RS)-2-hydroxy-cyclohexylmethyl)-nicotinamide (example 110) with heptane/ethanol on ChiralpakAD® yielded the (−)-enantiomer. MS (ISP) 406.3 (M+H)$^+$.

Example 122

(+)-cis-5-(4-Cyano-phenyl)-6-cyclopropylmethoxy-N-(2-hydroxy-cyclohexylmethyl)-nicotinamide Separation of the enantiomers of 5-(4-cyano-phenyl)-6-cyclopropylmethoxy-N-((1RS, 2RS)-2-hydroxy-cyclohexylmethyl)-nicotinamide (example 110) with heptane/ethanol on a ChiralpakAD® column yielded the (+)-enantiomer. MS (ISP) 406.3 (M+H)$^+$.

Example 123

(−)-5-(4-Cyano-phenyl)-6-cyclopropylmethoxy-N-((2-hydroxymethyl-butyl)-nicotinamide Separation of the enantiomers of 5-(4-cyano-phenyl)-6-cyclopropylmethoxy-N-(2-hydroxymethyl-butyl)-nicotinamide (example 115) with heptane/ethanol on ChiralpakAD® yielded the (−)-enantiomer. MS (ISP) 380.2 (M+H)$^+$.

Example 124

(+)-5-(4-Cyano-phenyl)-6-cyclopropylmethoxy-N-((2-hydroxymethyl-butyl)-nicotinamide Separation of the enantiomers of 5-(4-cyano-phenyl)-6-cyclopropylmethoxy-N-(2-hydroxymethyl-butyl)-nicotinamide (example 115) with heptane/ethanol on ChiralpakAD® yielded the (+)-enantiomer. MS (ISP) 380.2 (M+H)$^+$.

Example 125

(+)-5-(4-Cyano-phenyl)-N-(2-cyclopropyl-2-hydroxy-propyl)-6-cyclopropylmethoxy-nicotinamide The title compound was synthesized in analogy to Example 75, using 5-bromo-6-chloro-3-pyridinecarboxylic acid, hydroxymethyl-cyclopropan, 4-cyanophenylboronic acid and (+)-1-amino-2-cyclopropyl-propan-2-ol as starting materials to yield (+)-5-(4-cyano-phenyl)-N-(2-cyclopropyl-2-hydroxy-propyl)-6-cyclopropylmethoxy-nicotinamide. MS (ISP) 392.2 (M+H)$^+$, $\alpha_D^{20}$: +1.7° in MeOH.

Example 126

6-Cyclopropylmethoxy-5-(4-fluoro-phenyl)-N-(2-hydroxy-2-methyl-propyl)-nicotinamide The title compound was synthesized in analogy to Example 75, using 5-bromo-6-chloro-3-pyridinecarboxylic acid, hydroxymethyl-cyclopropan, 4-fluorophenylboronic acid and 1-amino-2-methyl-propan-2-ol hydrochloride as starting materials to yield 6-cyclopropylmethoxy-5-(4-fluoro-phenyl)-N-(2-hydroxy-2-methyl-propyl)-nicotinamide. MS (ISP) 359.1 (M+H)$^+$.

Example 127

(−)-6-Cyclopropylmethoxy-N-(2-hydroxymethyl-butyl)-5-(4-trifluoromethoxy-phenyl)-nicotinamide Separation of the enantiomers of 6-cyclopropylmethoxy-N-(2-hydroxymethyl-butyl)-5-(4-trifluoromethoxy-phenyl)-nicotinamide (example 118) with heptane/ethanol on a ChiralpakAD® column yielded the (−)-enantiomer. MS (ISP) 439.0 (M+H)$^+$.

Example 128

6-Cyclopropylmethoxy-5-(4-fluoro-phenyl)-N-(1-hydroxy-cyclopentylmethyl)-nicotinamide The title compound was synthesized in analogy to Example 75, using 5-bromo-6-chloro-3-pyridinecarboxylic acid, hydroxymethyl-cyclopropan, 4-fluorophenylboronic acid and 1-aminomethyl-cyclopentanol hydrochloride (CAS [76066-27-8]) as starting materials to yield 6-cyclopropyl-methoxy-5-(4-fluoro-phenyl)-N-(1-hydroxy-cyclopentylmethyl)-nicotinamide. MS (ISP) 385.3 $(M+H)^+$.

Example 129

5-(4-Chloro-phenyl)-N-((R,2R)-2-hydroxy-cyclohexyl)-6-(pyridin-3-ylmethoxy)-nicotinamide The title compound was synthesized in analogy to Example 75, using 5-bromo-6-chloro-3-pyridinecarboxylic acid, 3-pyridinemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(pyridin-3-ylmethoxy)-nicotinamide, MS (ISP) 438.1 $(M+H)^+$.

Example 130

5-(4-Fluoro-phenyl)-N-((1R,2R)-2-hydroxy-cyclohexyl)-6-(pyridin-3-ylmethoxy)-nicotinamide The title compound was synthesized in analogy to Example 75, using 5-bromo-6-chloro-3-pyridinecarboxylic acid, 3-pyridinemethanol, (4-fluoro-phenyl)-boronic acid and ((1R,2R)-2-amino-1-cyclohexanol as starting materials to yield 5-(4-fluoro-phenyl)-N-((1R,2R)-2-hydroxy-cyclohexyl)-6-(pyridin-3-ylmethoxy)-nicotinamide, MS (ISP) 422.0 $(M+H)^+$.

Example 131

5-(4-Chloro-phenyl)-N-((R)-2-cyclopropyl-2-hydroxy-propyl)-6-(pyridin-3-ylmethoxy)-nicotinamide The title compound was synthesized in analogy to Example 75, using 5-bromo-6-chloro-3-pyridinecarboxylic acid, 3-pyridinemethanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-(pyridin-3-ylmethoxy)-nicotinamide, MS (ISP) 438.1 $(M+H)^+$.

Example 132

N-((R)-2-Cyclopropyl-2-hydroxy-propyl)-5-(4-fluoro-phenyl)-6-(pyridin-3-ylmethoxy)-nicotinamide The title compound was synthesized in analogy to Example 75, using 5-bromo-6-chloro-3-pyridinecarboxylic acid, 3-pyridinemethanol, (4-fluoro-phenyl)-boronic acid and (R)-α-(aminomethyl)-α-methyl-cyclopropanemethanol as starting materials to yield N-((R)-2-cyclopropyl-2-hydroxy-propyl)-5-(4-fluoro-phenyl)-6-(pyridin-3-ylmethoxy)-nicotinamide, MS (ISP) 422.0 $(M+H)^+$.

Example 133

5-(4-Chloro-phenyl)-N-((R)-2-cyclopropyl-2-hydroxy-propyl)-6-(3-methyl-pyridin-2-ylmethoxy)-nicotinamide The title compound was synthesized in analogy to Example 75, using 5-bromo-6-chloro-3-pyridinecarboxylic acid, (3-methyl-pyridin-2-yl)-methanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-(3-methyl-pyridin-2-ylmethoxy)-nicotinamide, MS (ISP) 452.2 $(M+H)^+$.

Example 134

N-((R)-2-Cyclopropyl-2-hydroxy-propyl)-5-(4-fluoro-phenyl)-6-(3-methyl-pyridin-2-ylmethoxy)-nicotinamide The title compound was synthesized in analogy to Example 75, using 5-bromo-6-chloro-3-pyridinecarboxylic acid, (3-methyl-pyridin-2-yl)-methanol, (4-fluoro-phenyl)-boronic acid and (R)-α-(aminomethyl)-α-methyl-cyclopropanemethanol as starting materials to yield N-((R)-2-cyclopropyl-2-hydroxy-propyl)-5-(4-fluoro-phenyl)-6-(3-methyl-pyridin-2-ylmethoxy)-nicotinamide, MS (ISP) 436.4 $(M+H)^+$.

Example 135

5-(4-Chloro-phenyl)-N-((1R,2R)-2-hydroxy-cyclohexyl)-6-[methyl-(4-methyl-thiazol-2-ylmethyl)-amino]-nicotinamide The title compound was synthesized in analogy to Example 74, using 5-bromo-6-chloro-nicotinic acid methyl ester, methyl-(4-methyl-thiazol-2-ylmethyl)-amine (CAS [644950-37-8]), (4-chloro-phenyl)-boronic acid and (1R,2R)-2-amino-cyclohexanol hydrochloride as starting materials to yield 5-(4-chloro-phenyl)-N-((1R,2R)-2-hydroxy-cyclohexyl)-6-[methyl-(4-methyl-thiazol-2-ylmethyl)-amino]-nicotinamide. MS (ISP) 471.2 $(M+H)^+$.

Example 136

(RS)-N-(2-Cyclobutyl-2-hydroxy-propyl)-6-cyclopropylmethoxy-5-(4-fluoro-phenyl)-nicotinamide 1-Amino-2-cyclobutyl-propan-2-ol hydrochloride Acetylcyclobutane (4.7 g) and zinc iodide (0.016 g) were placed under argon in a dry flask. The mixture was cooled in an ice bath. Trimethylsilyl cyanide (5.28 g) was added dropwise. After stirring for 10 min the ice bath was removed and the mixture was stirred at room temperature for 30 min. The crude product was dissolved in diethyl ether (7 ml) and added to $LiAlH_4$ (4 M solution in diethyl ether, 35.25 ml) at such a rate that a slight reflux was maintained. The mixture was heated to reflux for a further 1 h. After cooling to room temperature, water (5.35 ml) was added slowly. NaOH solution (15% in water, 5.35 ml) and water (16.05 ml) were added slowly. The mixture was filtered and the filtrate was dried over KOH, filtered and concentrated in vacuo. The residue was dissolved in diethyl ether. HCl (2 M in diethyl ether, 23.5 ml) was added. The solid was filtered off, washed with ether and dried to give 1-amino-2-cyclobutyl-propan-2-ol hydrochloride (6.92 g) as a colorless solid.

(RS)-N-(2-Cyclobutyl-2-hydroxy-propyl)-6-cyclopropylmethoxy-5-(4-fluoro-phenyl)-nicotinamide The title compound was synthesized in analogy to Example 75, using 5-bromo-6-chloro-3-pyridinecarboxylic acid, hydroxymethyl-cyclopropan, 4-fluorophenylboronic acid and 1-amino-2-cyclobutyl-propan-2-ol hydrochloride as starting materials to yield (RS)-N-(2-cyclobutyl-2-hydroxy-propyl)-6-cyclopropylmethoxy-5-(4-fluoro-phenyl)-nicotinamide. MS (ISP) 399.0 (M+H)$^+$.

Example 137

5-(4-Chloro-phenyl)-N-((1R,2R)-2-hydroxy-cyclohexyl)-6-(5-methyl-isoxazol-3-ylmethoxy)-nicotinamide The title compound was synthesized in analogy to Example 75, using 5-bromo-6-chloro-3-pyridinecarboxylic acid, 5-methyl-3-isoxazolemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(5-methyl-isoxazol-3-ylmethoxy)-nicotinamide, MS (ISP) 442.1 (M+H)$^+$.

Example 138

5-(4-Fluoro-phenyl)-N-((1R,2R)-2-hydroxy-cyclohexyl)-6-(5-methyl-isoxazol-3-ylmethoxy)-nicotinamide The title compound was synthesized in analogy to Example 75, using 5-bromo-6-chloro-3-pyridinecarboxylic acid, 5-methyl-3-isoxazolemethanol, (4-fluoro-phenyl)-boronic acid and ((1R,2R)-2-amino-1-cyclohexanol as starting materials to yield 5-(4-fluoro-phenyl)-N-((1R,2R)-2-hydroxy-cyclohexyl)-6-(5-methyl-isoxazol-3-ylmethoxy)-nicotinamide, MS (ISP) 426.1 (M+H)$^+$.

Example 139

5-(4-Chloro-phenyl)-N-((R)-2-cyclopropyl-2-hydroxy-propyl)-6-(5-methyl-isoxazol-3-ylmethoxy)-nicotinamide The title compound was synthesized in analogy to Example 75, using 5-bromo-6-chloro-3-pyridinecarboxylic acid, 5-methyl-3-isoxazolemethanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-(5-methyl-isoxazol-3-ylmethoxy)-nicotinamide, MS (ISP) 442.1 (M+H)$^+$.

Example 140

N-((R)-2-Cyclopropyl-2-hydroxy-propyl)-5-(4-fluoro-phenyl)-6-(5-methyl-isoxazol-3-ylmethoxy)-nicotinamide The title compound was synthesized in analogy to Example 75, using 5-bromo-6-chloro-3-pyridinecarboxylic acid, 5-methyl-3-isoxazolemethanol, (4-fluoro-phenyl)-boronic acid and (R)-α-(aminomethyl)-α-methyl-cyclopropanemethanol as starting materials to yield N-((R)-2-cyclopropyl-2-hydroxy-propyl)-5-(4-fluoro-phenyl)-6-(5-methyl-isoxazol-3-ylmethoxy)-nicotinamide, MS (ISP) 426.1 (M+H)$^+$.

Example 141

N-((R)-2-Cyclopropyl-2-hydroxy-propyl)-5-(4-fluoro-phenyl)-6-(pyridin-2-ylmethoxy)-nicotinamide The title compound was synthesized in analogy to Example 75, using 5-bromo-6-chloro-3-pyridinecarboxylic acid, 2-pyridinemethanol, (4-fluoro-phenyl)-boronic acid and (R)-α-(aminomethyl)-α-methyl-cyclopropanemethanol as starting materials to yield N-((R)-2-cyclopropyl-2-hydroxy-propyl)-5-(4-fluoro-phenyl)-6-(pyridin-2-ylmethoxy)-nicotinamide, MS (ISP) 422.0 (M+H)$^+$.

Example 142

(RS)-6-Cyclopropylmethoxy-5-(4-fluoro-phenyl)-N-(3,3,3-trifluoro-2-hydroxy-2-methyl-propyl)-nicotinamide The title compound was synthesized in analogy to Example 75, using 5-bromo-6-chloro-3-pyridinecarboxylic acid, hydroxymethyl-cyclopropane, 4-fluorophenylboronic acid and 3-amino-1,1,1-trifluoro-2-methyl-propan-2-ol (CAS [354-68-7]) as starting materials to yield (RS)-6-cyclopropylmethoxy-5-(4-fluoro-phenyl)-N-(3,3,3-trifluoro-2-hydroxy-2-methyl-propyl)-nicotinamide. MS (ISP) 413.3 (M+H)$^+$.

Example 143

(RS)-6-Cyclopropylmethoxy-N-(3,3,3-trifluoro-2-hydroxy-2-methyl-propyl)-5-(4-trifluoromethyl-phenyl)-nicotinamide The title compound was synthesized in analogy to Example 75, using 5-bromo-6-chloro-3-pyridinecarboxylic acid, hydroxymethyl-cyclopropan, 4-trifluoromethyl-phenylboronic acid and 3-amino-1,1,1-trifluoro-2-methyl-propan-2-ol (CAS [354-68-7]) as starting materials to yield (RS)-6-cyclopropylmethoxy-N-(3,3,3-trifluoro-2-hydroxy-2-methyl-propyl)-5-(4-trifluoromethyl-phenyl)-nicotinamide. MS (ISP) 463.0 (M+H)$^+$.

Example 144

(RS)-6-Cyclopropylmethoxy-N-(3,3,3-trifluoro-2-hydroxy-2-methyl-propyl)-5-(4-trifluoromethoxy-phenyl)-nicotinamide The title compound was synthesized in analogy to Example 75, using 5-bromo-6-chloro-3-pyridinecarboxylic acid, hydroxymethyl-cyclopropan, 4-trifluoromethoxy-phenylboronic acid and 3-amino-1,1,1-trifluoro-2-methyl-propan-2-ol (CAS [354-68-7]) as starting materials to yield (RS)-6-cyclopropylmethoxy-N-(3,3,3-trifluoro-2-hydroxy-2-methyl-propyl)-5-(4-trifluoromethoxy-phenyl)-nicotinamide. MS (ISP) 479.0 (M+H)$^+$.

Example 145

5-(4-Chloro-phenyl)-N-((1R,2R)-2-hydroxy-cyclohexyl)-6-(3-methyl-pyridin-2-ylmethoxy)-nicotinamide The title compound was synthesized in analogy to Example 75, using 5-bromo-6-chloro-3-pyridinecarboxylic acid, (3-methyl-pyridin-2-yl)-methanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(3-methyl-pyridin-2-ylmethoxy)-nicotinamide, MS (ISP) 452.1 (M+H)$^+$.

Example 146

5-(4-Fluoro-phenyl)-N-((1R,2R)-2-hydroxy-cyclohexyl)-6-(3-methyl-pyridin-2-ylmethoxy)-nicotinamide The title compound was synthesized in analogy to Example 75, using 5-bromo-6-chloro-3-pyridinecarboxylic acid, (3-methyl-pyridin-2-yl)-methanol, (4-fluoro-phenyl)-boronic acid and ((1R,2R)-2-amino-1-cyclohexanol as starting materials to yield 5-(4-fluoro-phenyl)-N-((1R,2R)-2-hydroxy-cyclohexyl)-6-(3-methyl-pyridin-2-ylmethoxy)-nicotinamide, MS (ISP) 436.2 (M+H)$^+$.

Example 147

5-(4-Chloro-phenyl)-N-((1R,2R)-2-hydroxy-cyclohexyl)-6-(pyridin-2-ylmethoxy)-nicotinamide The title compound was synthesized in analogy to Example 75, using 5-bromo-6-chloro-3-pyridinecarboxylic acid, 2-pyridinemethanol, (4-chloro-phenyl)-boronic acid and ((1R,2R)-2-amino-1-cyclohexanol as starting materials to yield 5-(4-chloro-phenyl)-N-((1R,2R)-2-hydroxy-cyclohexyl)-6-(pyridin-2-ylmethoxy)-nicotinamide, MS (ISP) 440.2 (M+H)$^+$.

Example 148

5-(4-Chloro-phenyl)-N-((R)-2-cyclopropyl-2-hydroxy-propyl)-6-(pyridin-2-ylmethoxy)-nicotinamide The title compound was synthesized in analogy to Example 75, using 5-bromo-6-chloro-3-pyridinecarboxylic acid, 2-pyridinemethanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-(pyridin-2-ylmethoxy)-nicotinamide, MS (ISP) 438.1 (M+H)$^+$.

Example 149

5-(4-Fluoro-phenyl)-N-((1R,2R)-2-hydroxy-cyclohexyl)-6-(pyridin-2-ylmethoxy)-nicotinamide The title compound was synthesized in analogy to Example 75, using 5-bromo-6-chloro-3-pyridinecarboxylic acid, 2-pyridinemethanol, (4-fluoro-phenyl)-boronic acid and ((1R,2R)-2-amino-1-cyclohexanol as starting materials to yield 5-(4-fluoro-phenyl)-N-((1R,2R)-2-hydroxy-cyclohexyl)-6-(pyridin-2-ylmethoxy)-nicotinamide, MS (ISP) 422.0 (M+H)$^+$.

Example 150

5-(4-Fluoro-phenyl)-N-((1R,2R)-2-hydroxy-cyclohexyl)-6-(pyridin-4-ylmethoxy)-nicotinamide The title compound was synthesized in analogy to Example 75, using 5-bromo-6-chloro-3-pyridinecarboxylic acid, 4-pyridinemethanol, (4-fluoro-phenyl)-boronic acid and ((1R,2R)-2-amino-1-cyclohexanol as starting materials to yield 5-(4-fluoro-phenyl)-N-((1R,2R)-2-hydroxy-cyclohexyl)-6-(pyridin-4-ylmethoxy)-nicotinamide, MS (ISP) 422.0 (M+H)$^+$.

Example 151

N-((R)-2-Cyclopropyl-2-hydroxy-propyl)-5-(4-fluoro-phenyl)-6-(pyridin-4-ylmethoxy)-nicotinamide The title compound was synthesized in analogy to Example 75, using 5-bromo-6-chloro-3-pyridinecarboxylic acid, 4-pyridinemethanol, (4-fluoro-phenyl)-boronic acid and (R)-α-(aminomethyl)-α-methyl-cyclopropanemethanol as starting materials to yield N-((R)-2-cyclopropyl-2-hydroxy-propyl)-5-(4-fluoro-phenyl)-6-(pyridin-4-ylmethoxy)-nicotinamide, MS (ISP) 422.0 (M+H)$^+$.

Example 152

5-(4-Chloro-phenyl)-N-((R)-2-cyclopropyl-2-hydroxy-propyl)-6-(pyridin-4-ylmethoxy)-nicotinamide The title compound was synthesized in analogy to Example 75, using 5-bromo-6-chloro-3-pyridinecarboxylic acid, 4-pyridinemethanol, (4-chloro-phenyl)-boronic acid and (R)-α-(aminomethyl)-α-methyl-cyclopropanemethanol as starting materials to yield 5-(4-chloro-phenyl)-N-((R)-2-cyclopropyl-2-hydroxy-propyl)-6-(pyridin-4-ylmethoxy)-nicotinamide, MS (ISP) 438.1 (M+H)$^+$.

Example 153

5-(4-Cyano-phenyl)-6-cyclopropylmethoxy-N-((1R,2R)-2-hydroxy-cyclohexyl)-nicotinamide The title compound was synthesized in analogy to Example 75, using 5-bromo-6-chloro-3-pyridinecarboxylic acid, 4-pyridinemethanol, (4-cyano-phenyl)-boronic acid and ((1R,2R)-2-amino-1-cyclohexanol as starting materials to yield 5-(4-cyano-phenyl)-6-cyclopropylmethoxy-N-((1R,2R)-2-hydroxy-cyclohexyl)-nicotinamide, MS (ISP) 392.2 (M+H)$^+$.

Example 154

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example 155

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 156

Injection solutions can have the following composition:

| Compound of formula (I) | 3.0 mg |
| --- | --- |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

It is to be understood that the invention is not limited to the particular embodiments of the invention described above, as variations of the particular embodiments may be made and still fall within the scope of the appended claims.

The invention claimed is:
1. A compound of the formula I:

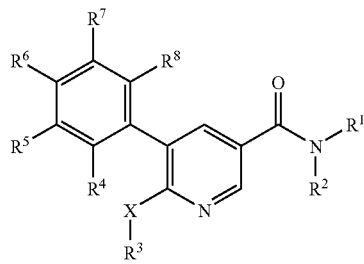

wherein:
$R^1$ is selected from the group consisting of
cycloalkyl which is unsubstituted or substituted by hydroxy or lower alkoxy, lower hydroxyalkyl, lower hydroxyhalogenalkyl,
—$CH_2$—$CR^9R^{10}$-cycloalkyl, and
—$CR^{11}R^{12}$—$COOR^{13}$;
$R^9$ is hydrogen or lower alkyl;
$R^{10}$ is hydrogen, hydroxy or lower alkoxy;
$R^{11}$ and $R^{12}$ independently from each other are hydrogen or lower alkyl;
$R^{13}$ is lower alkyl;
$R^2$ is hydrogen;
X is O or $NR^{14}$;
$R^{14}$ is hydrogen or lower alkyl;
$R^3$ is selected from the group consisting of lower alkyl,
cycloalkyl,
lower cycloalkylalkyl,
lower alkoxyalkyl,
lower halogenalkyl,
lower carbamoylalkyl,
lower phenylalkyl,
lower heterocyclylalkyl,
lower heteroarylalkyl wherein the heteroaryl group is unsubstituted or mono- or di-substituted by halogen, and
phenyl which is unsubstituted or mono- or di-substituted by halogen;
or $R^3$ and $R^{14}$ together with the nitrogen atom they are attached to form a 5-, 6- or 7-membered heterocyclic ring;
$R^4$ and $R^8$ independently from each other are hydrogen or halogen;
$R^5$ and $R^7$ independently from each other are selected from the group consisting of hydrogen, halogen, lower halogenalkyl, lower halogenalkoxy and cyano;
$R^6$ is selected from the group consisting of hydrogen, halogen, lower halogenalkyl, lower halogenalkoxy and cyano;
or a pharmaceutically acceptable salt thereof.

2. The compound according to claim 1, wherein X is O.

3. The compound according to claim 1, wherein $R^1$ is cycloalkyl which is unsubstituted or substituted by hydroxy or lower alkoxy.

4. The compound according to claim 1, wherein $R^1$ is cycloalkyl substituted by hydroxy.

5. The compound according to claim 1, wherein $R^1$ is —$CH_2$—$CR^9R^{10}$-cycloalkyl and wherein $R^9$ is hydrogen or lower alkyl and $R^{10}$ is hydrogen, hydroxy or lower alkoxy.

6. The compound according to claim 1, wherein $R^1$ is —$CH_2$—$CR^9R^{10}$-cycloalkyl and wherein $R^9$ is hydrogen and $R^{10}$ is hydroxy.

7. The compound according to claim 1, wherein $R^3$ is selected from the group consisting of lower alkyl, cycloalkyl, lower cycloalkylalkyl, lower alkoxyalkyl, lower halogenalkyl, lower carbamoylalkyl, lower phenylalkyl, lower heterocyclylalkyl, lower heteroarylalkyl wherein the heteroaryl group is unsubstituted or mono- or di-substituted by halogen, and phenyl which is unsubstituted or mono- or di-substituted by halogen.

8. The compound according to claim 1, wherein $R^3$ is selected from lower cycloalkylalkyl, lower alkoxyalkyl and lower heteroarylalkyl.

9. The compound according to claim 1, wherein $R^3$ is lower cycloalkylalkyl.

10. The compound according to claim 1, wherein $R^3$ is lower alkoxyalkyl.

11. The compound according to claim 1, wherein $R^4$ and $R^8$ independently from each other are hydrogen or halogen, $R^5$ and $R^7$ independently from each other are selected from the group consisting of hydrogen, halogen, lower halogenalkyl, lower halogenalkoxy and cyano, $R^6$ is selected from the group consisting of hydrogen, halogen, lower halogenalkyl, lower halogenalkoxy and cyano, and not all of $R^4$ to $R^8$ are hydrogen.

12. The compound according to claim 1, wherein $R^6$ is halogen or lower halogenalkyl and $R^4$, $R^5$, $R^7$ and $R^8$ are hydrogen.

13. The compound according to claim 1, wherein $R^4$ is halogen, $R^7$ is halogen or lower halogenalkyl and $R^5$, $R^6$ and $R^8$ are hydrogen.

14. The compound according to claim 1, wherein X is $NR^{14}$, and $R^{14}$ is hydrogen or lower alkyl or $R^{14}$ together with $R^3$ and with the nitrogen atom they are attached to form a 5-, 6- or 7-membered heterocyclic ring.

15. The compound according to claim 1, wherein
X is O;
$R^1$ is selected from the group consisting of
cycloalkyl which is unsubstituted or substituted by hydroxy or lower alkoxy,
—$CH_2$—$CR^9R^{10}$-cycloalkyl, and
—$CR^{11}R^{12}$—$COOR^{13}$;
$R^9$ is hydrogen or lower alkyl;
$R^{10}$ is hydrogen, hydroxy or lower alkoxy;
$R^{11}$ and $R^{12}$ independently from each other are hydrogen or lower alkyl;
$R^{13}$ is lower alkyl;
$R^2$ is hydrogen;
$R^3$ is selected from the group consisting of lower alkyl, cycloalkyl,
lower cycloalkylalkyl,
lower alkoxyalkyl, and
phenyl which is unsubstituted or mono- or di-substituted by halogen;
$R^4$ and $R^8$ independently from each other are hydrogen or halogen;
$R^5$ and $R^7$ independently from each other are selected from the group consisting of hydrogen, halogen and lower halogenalkyl;
$R^6$ is selected from the group consisting of hydrogen, halogen and lower halogenalkyl;
or a pharmaceutically acceptable salt thereof.

16. The compound according to claim 1, selected from the group consisting of:
5-(2-chloro-5-trifluoromethyl-phenyl)-6-cyclopentyloxy-N-((1R,2R)-2-hydroxy-cyclohexyl)-nicotinamide;
6-butoxy-5-(2-fluoro-5-trifluoromethyl-phenyl)-N-((1R,2R)-2-hydroxy-cyclohexyl)-nicotinamide,
6-butoxy-5-(4-chloro-phenyl)-N-((1R,2R)-2-hydroxy-cyclohexyl)-nicotinamide,
6-butoxy-5-(4-chloro-phenyl)-N-(2-cyclopropyl-2-hydroxy-propyl)-nicotinamide,
5-(4-chloro-phenyl)-6-cyclopropylmethoxy-N-((1R,2R)-2-hydroxy-cyclohexyl)-nicotinamide,
5-(4-chloro-phenyl)-N-(2-cyclopropyl-2-hydroxy-propyl)-6-cyclopropylmethoxy-nicotinamide,
6-cyclopropylmethoxy-5-(2-fluoro-5-trifluoromethyl-phenyl)-N-((1R,2R)-2-hydroxy-cyclohexyl)-nicotinamide;
6-butoxy-5-(2-chloro-5-trifluoromethyl-phenyl)-N-((1R,2R)-2-hydroxy-cyclohexyl)-nicotinamide,
5-(2-chloro-5-trifluoromethyl-phenyl)-6-cyclopropylmethoxy-N-((1R,2R)-2-hydroxy-cyclohexyl)-nicotinamide;
6-butoxy-5-(2,4-dichloro-phenyl)-N-((1R,2R)-2-hydroxy-cyclohexyl)-nicotinamide,
5-(2,4-dichloro-phenyl)-N-((1R,2R)-2-hydroxy-cyclohexyl)-6-propoxy-nicotinamide,
5-(2,4-dichloro-phenyl)-N-((1R,2R)-2-hydroxy-cyclohexyl)-6-pentyloxy-nicotinamide,
N-(2-cyclopropyl-2-hydroxy-propyl)-5-(2,4-dichloro-phenyl)-6-(2-methoxy-ethoxy)-nicotinamide,
6-cyclopropylmethoxy-5-(2,4-dichloro-phenyl)-N-((R,2R)-2-hydroxy-cyclohexyl)-nicotinamide,
5-(4-chloro-phenyl)-N-(2-cyclopropyl-2-hydroxy-propyl)-6-(2-methoxy-ethoxy)-nicotinamide,
5-(4-chloro-phenyl)-N-((1R,2R)-2-hydroxy-cyclohexyl)-6-(2-methoxy-ethoxy)-nicotinamide,
5-(4-chloro-phenyl)-N-(trans-2-hydroxy-cyclohexyl)-6-(2-methoxy-ethoxy)-nicotinamide,
5-(4-chloro-phenyl)-N-(2-cyclopropyl-2-hydroxy-propyl)-6-(3-methoxy-propoxy)-nicotinamide,
5-(4-chloro-phenyl)-N-((1R,2R)-2-hydroxy-cyclohexyl)-6-(3-methoxy-propoxy)-nicotinamide,
6-benzylamino-5-(4-chloro-phenyl)-N-((1R,2R)-2-hydroxy-cyclohexyl)-nicotinamide,
5-(4-chloro-phenyl)-6-(cyclopropylmethyl-amino)-N-((1R,2R)-2-hydroxy-cyclohexyl)-nicotinamide,
5-(4-chloro-phenyl)-N-(2-cyclopropyl-2-hydroxy-propyl)-6-(2-methoxy-ethylamino)-nicotinamide,
N-((trans)-2-hydroxy-cyclohexyl)-6-(2-methoxy-ethoxy)-5-(4-trifluoromethyl-phenyl)-nicotinamide,
N-((trans)-2-hydroxy-cyclohexyl)-6-(2-methoxy-ethoxy)-5-(4-trifluoromethoxy-phenyl)-nicotinamide,
6-cyclopropylmethoxy-5-(3,4-difluoro-phenyl)-N-((trans)-2-hydroxy-cyclohexyl)-nicotinamide,
6-cyclopropylmethoxy-5-(4-fluoro-phenyl)-N-((trans)-2-hydroxy-cyclohexyl)-nicotinamide,
6-cyclopropylmethoxy-N-((trans)-2-hydroxy-cyclohexyl)-5-(4-trifluoromethyl-phenyl)-nicotinamide,
6-cyclopropylmethoxy-N-((trans)-2-hydroxy-cyclohexyl)-5-(4-trifluoromethoxy-phenyl)-nicotinamide,
5-(4-cyano-phenyl)-6-cyclopropylmethoxy-N-((1S,2S)-2-hydroxy-cyclohexyl)-nicotinamide,
(RS)-5-(4-chloro-phenyl)-N-(2-hydroxy-butyl)-6-(2-methoxy-ethoxy)-nicotinamide,
(RS)-5-(4-chloro-phenyl)-6-(2-methoxy-ethoxy)-N-(3,3,3-trifluoro-2-hydroxy-propyl)-nicotinamide,
6-benzyloxy-5-(4-chloro-phenyl)-N-((1R,2R)-2-hydroxy-cyclohexyl)-nicotinamide,
5-(4-chloro-phenyl)-N-(3-hydroxy-2,2-dimethyl-propyl)-6-(2-methoxy-ethoxy)-nicotinamide,
(RS)-5-(4-chloro-phenyl)-N-(2-hydroxymethyl-butyl)-6-(2-methoxy-ethoxy)-nicotinamide,
5-(4-chloro-phenyl)-N-((1RS,2RS)-2-hydroxy-cyclohexylmethyl)-6-(2-methoxy-ethoxy)-nicotinamide,
5-(4-chloro-phenyl)-N-((1R,2R)-2-methoxy-cyclohexyl)-6-(2-methoxy-ethoxy)-nicotinamide,
5-(4-chloro-phenyl)-N-((1SR,2RS)-2-hydroxy-cyclohexylmethyl)-6-(2-methoxy-ethoxy)-nicotinamide,
5-(4-chloro-phenyl)-N-(1-hydroxy-cyclohexylmethyl)-6-(2-methoxy-ethoxy)-nicotinamide,
5-(4-chloro-phenyl)-N-((1R,2R)-2-hydroxy-cyclohexyl)-6-(1-methyl-cyclopropylmethoxy)-nicotinamide,
(−)-5-(4-chloro-phenyl)-N-(2-cyclopropyl-2-hydroxy-propyl)-6-(2-methoxy-ethoxy)-nicotinamide,
(+)-5-(4-chloro-phenyl)-N-(2-cyclopropyl-2-hydroxy-propyl)-6-(2-methoxy-ethoxy)-nicotinamide,
5-(4-chloro-phenyl)-6-cyclopentylmethoxy-N-((R,2R)-2-hydroxy-cyclohexyl)-nicotinamide,
5-(4-chloro-phenyl)-6-(2-cyclopropyl-ethoxy)-N-((1R,2R)-2-hydroxy-cyclohexyl)-nicotinamide,
5-(4-chloro-phenyl)-6-cyclobutylmethoxy-N-((1R,2R)-2-hydroxy-cyclohexyl)-nicotinamide,
5-(4-chloro-phenyl)-6-(3,3-dimethyl-butoxy)-N-((1R,2R)-2-hydroxy-cyclohexyl)-nicotinamide,
5-(4-chloro-phenyl)-N-((1RS,2RS)-2-hydroxy-cyclohexylmethyl)-6-(1-methyl-cyclopropylmethoxy)-nicotinamide,
6-benzyloxy-5-(4-chloro-phenyl)-N-((1RS,2RS)-2-hydroxy-cyclohexylmethyl)-nicotinamide, 5-(4-fluoro-phenyl)-N-((1R,2R)-2-hydroxy-cyclohexyl)-6-(2-methoxy-ethoxy)-nicotinamide,
N-((1R,2R)-2-hydroxy-cyclohexyl)-6-(2-methoxy-ethoxy)-5-(4-trifluoromethyl-phenyl)-nicotinamide,
N-((1R,2R)-2-hydroxy-cyclohexyl)-6-(2-methoxy-ethoxy)-5-(4-trifluoromethoxy-phenyl)-nicotinamide,
5-(4-chloro-phenyl)-N-((1R,2R)-2-hydroxy-cyclohexyl)-6-(2-isopropoxy-ethoxy)-nicotinamide,
5-(4-fluoro-phenyl)-N-((1R,2R)-2-hydroxy-cyclohexyl)-6-(2-isopropoxy-ethoxy)-nicotinamide,
5-(4-chloro-phenyl)-N-((1R,2R)-2-hydroxy-cyclohexyl)-6-[(2-methoxy-ethyl)-methyl-amino]-nicotinamide,
N-((1R,2R)-2-hydroxy-cyclohexyl)-6-[(2-methoxy-ethyl)-methyl-amino]-5-(4-trifluoromethyl-phenyl)-nicotinamide,
5-(4-chloro-phenyl)-6-([1,3]dioxolan-4-ylmethoxy)-N-((1R,2R)-2-hydroxy-cyclohexyl)-nicotinamide,
6-([1,3]dioxolan-4-ylmethoxy)-N-((1R,2R)-2-hydroxy-cyclohexyl)-5-(4-trifluoromethyl-phenyl)-nicotinamide,
6-cyclopropylmethoxy-5-(4-fluoro-phenyl)-N-((1R,2R)-2-hydroxy-cyclohexyl)-nicotinamide,
5-(4-chloro-phenyl)-N-((1R,2R)-2-hydroxy-cyclohexyl)-6-isobutoxy-nicotinamide,
5-(4-chloro-phenyl)-6-(2-ethoxy-ethoxy)-N-((1R,2R)-2-hydroxy-cyclohexyl)-nicotinamide,
5-(4-chloro-phenyl)-N-((1R,2R)-2-hydroxy-cyclohexyl)-6-(3-methyl-butoxy)-nicotinamide,
(−)-cis-5-(4-chloro-phenyl)-6-cyclopropylmethoxy-N-2-hydroxy-cyclohexylmethyl)-nicotinamide,
6-(4-carbamoyl-butoxy)-5-(4-chloro-phenyl)-N-((1R,2R)-2-hydroxy-cyclohexyl)-nicotinamide,
(−)-5-(4-chloro-phenyl)-6-cyclopropylmethoxy-N-(2-hydroxymethyl-butyl)-nicotinamide,
(RS)-5-(4-chloro-phenyl)-N-(2-hydroxymethyl-pentyl)-6-(2-methoxy-ethoxy)-nicotinamide,
6-cyclopropylmethoxy-N-((1R,2R)-2-hydroxy-cyclohexyl)-5-(4-trifluoromethyl-phenyl)-nicotinamide,
5-(4-chloro-phenyl)-N-((1R,2R)-2-hydroxy-cyclohexyl)-6-(oxetan-2-ylmethoxy)-nicotinamide,
5-(4-chloro-phenyl)-N-((1R,2R)-2-hydroxy-cyclohexyl)-6-(2,2,2-trifluoro-ethoxy)-nicotinamide,
5-(4-chloro-phenyl)-N-(2-cyclopropyl-2-hydroxy-propyl)-6-(2,2,2-trifluoro-ethoxy)-nicotinamide,
5-(4-fluoro-phenyl)-N-((1R,2R)-2-hydroxy-cyclohexyl)-6-(2,2,2-trifluoro-ethoxy)-nicotinamide,
N-(2-cyclopropyl-2-hydroxy-propyl)-5-(4-fluoro-phenyl)-6-(2,2,2-trifluoro-ethoxy)-nicotinamide,
N-((1R,2R)-2-hydroxy-cyclohexyl)-6-(2,2,2-trifluoro-ethoxy)-5-(4-trifluoromethyl-phenyl)-nicotinamide,
N-(2-cyclopropyl-2-hydroxy-propyl)-6-(2,2,2-trifluoro-ethoxy)-5-(4-trifluoromethyl-phenyl)-nicotinamide,
N-((1R,2R)-2-hydroxy-cyclohexyl)-6-(2,2,2-trifluoro-ethoxy)-5-(4-trifluoromethoxy-phenyl)-nicotinamide,
5-(4-chloro-phenyl)-N-((1RS,2RS)-2-hydroxy-cyclohexylmethyl)-6-[(2-methoxy-ethyl)-methyl-amino]-nicotinamide,
(−)-cis-6-cyclopropylmethoxy-5-(4-fluoro-phenyl)-N-(2-hydroxy-cyclohexylmethyl)-nicotinamide,
(−)-cis-5-(4-chloro-phenyl)-N-(2-hydroxy-cyclohexylmethyl)-6-(2-methoxy-ethoxy)-nicotinamide,
(−)-6-cyclopropylmethoxy-5-(4-fluoro-phenyl)-N-(2-hydroxymethyl-butyl)-nicotinamide,
(−)-cis-5-(4-fluoro-phenyl)-N-(2-hydroxy-cyclohexylmethyl)-6-(2-methoxy-ethoxy)-nicotinamide,
5-(4-chloro-phenyl)-6-(cyclopropylmethyl-methyl-amino)-N-((1R,2R)-2-hydroxy-cyclohexyl)-nicotinamide,
5-(4-chloro-phenyl)-6-(cyclopropylmethyl-methyl-amino)-N-((1RS,2RS)-2-hydroxy-cyclohexylmethyl)-nicotinamide,
6-(cyclopropylmethyl-methyl-amino)-5-(4-fluoro-phenyl)-N-((1R,2R)-2-hydroxy-cyclohexyl)-nicotinamide,
6-(cyclopropylmethyl-methyl-amino)-5-(4-fluoro-phenyl)-N-((1RS,2RS)-2-hydroxy-cyclohexylmethyl)-nicotinamide,
5-(4-chloro-phenyl)-N-(2-cyclopropyl-2-hydroxy-propyl)-6-(3-methyl-isoxazol-5-ylmethoxy)-nicotinamide,
5-(4-chloro-phenyl)-N-((1R,2R)-2-hydroxy-cyclohexyl)-6-(3-methyl-isoxazol-5-ylmethoxy)-nicotinamide,
cis-5-(4-chloro-phenyl)-N-(2-hydroxy-cyclohexylmethyl)-6-(3-methyl-isoxazol-5-ylmethoxy)-nicotinamide,
5-(4-chloro-phenyl)-N-(2-hydroxymethyl-butyl)-6-(3-methyl-isoxazol-5-ylmethoxy)-nicotinamide,
N-((R)-2-cyclopropyl-2-hydroxy-propyl)-6-cyclopropylmethoxy-5-(4-trifluoromethyl-phenyl)-nicotinamide,
N-((S)-2-cyclopropyl-2-hydroxy-propyl)-6-cyclopropylmethoxy-5-(4-trifluoromethyl-phenyl)-nicotinamide,
6-cyclopropylmethoxy-N-((1RS,2RS)-2-hydroxy-cyclohexylmethyl)-5-(4-trifluoromethoxy-phenyl)-nicotinamide,
(RS)-N-(2-cyclopropyl-2-hydroxy-propyl)-6-cyclopropylmethoxy-5-(4-trifluoromethoxy-phenyl)-nicotinamide,
6-cyclopropylmethoxy-N-((1R,2R)-2-hydroxy-cyclohexyl)-5-(4-trifluoromethoxy-phenyl)-nicotinamide,
5-(4-chloro-phenyl)-N-((1R,2R)-2-hydroxy-cyclohexyl)-6-(methyl-propyl-amino)-nicotinamide,
5-(4-chloro-phenyl)-N-(2-cyclopropyl-2-hydroxy-propyl)-6-(pyridin-2-ylmethoxy)-nicotinamide,
(−)-cis-6-cyclopropylmethoxy-N-((2-hydroxy-cyclohexylmethyl)-5-(4-trifluoromethoxy-phenyl)-nicotinamide,
N-((R)-2-cyclopropyl-2-hydroxy-propyl)-6-(2-methoxy-ethoxy)-5-(4-trifluoromethyl-phenyl)-nicotinamide,
5-(4-fluoro-phenyl)-N-((1R,2R)-2-hydroxy-cyclohexyl)-6-(methyl-propyl-amino)-nicotinamide,
N-((R)-2-cyclopropyl-2-hydroxy-propyl)-5-(4-fluoro-phenyl)-6-(2-methoxy-ethoxy)-nicotinamide,
N-((R)-2-cyclopropyl-2-hydroxy-propyl)-6-cyclopropylmethoxy-5-(4-fluoro-phenyl)-nicotinamide,
3'-(4-chloro-phenyl)-3,4,5,6-tetrahydro-2H-[1,2']bipyridinyl-5'-carboxylic acid ((1R,2R)-2-hydroxy-cyclohexyl)-amide,
5-(4-chloro-phenyl)-N-((S)-2-cyclopropyl-2-hydroxy-propyl)-6-(3-methyl-isoxazol-5-ylmethoxy)-nicotinamide,
(−)-N-(2-cyclopropyl-2-hydroxy-propyl)-6-cyclopropylmethoxy-5-(4-trifluoromethoxy-phenyl)-nicotinamide,
5-(4-chloro-phenyl)-N-((1R,2R)-2-hydroxy-cyclohexyl)-6-(1-methyl-1H-imidazol-2-ylmethoxy)-nicotinamide,
6-cyclopropylmethoxy-N-((1RS,2RS)-2-hydroxy-cyclohexylmethyl)-5-(4-trifluoromethyl-phenyl)-nicotinamide
5-(4-chloro-phenyl)-N-((1R,2R)-2-hydroxy-cyclohexyl)-6-(2-methyl-2H-[1,2,4]triazol-3-ylmethoxy)-nicotinamide, cis-5-(4-chloro-phenyl)-N-(2-hydroxy-cyclohexylm-ethyl)-6-(2-methyl-2H-[1,2,4]triazol-3-ylmethoxy)-nicotinamide,
cis-5-(4-Chloro-phenyl)-N-(2-hydroxy-cyclohexylm-ethyl)-6-(1-methyl-1H-imidazol-2-ylmethoxy)-nicotinamide,
cis-5-(4-chloro-phenyl)-N-(2-hydroxy-cyclohexylm-ethyl)-6-(pyrimidin-2-ylmethoxy)-nicotinamide,
5-(4-chloro-phenyl)-N-(2-hydroxymethyl-butyl)-6-(pyrimidin-2-ylmethoxy)-nicotinamide,
(−)-cis-6-cyclopropylmethoxy-N-(2-hydroxy-cyclohexylmethyl)-5-(4-trifluoromethyl-phenyl)-nicotinamide,
5-(4-cyano-phenyl)-6-cyclopropylmethoxy-N-((1RS,2RS)-2-hydroxy-cyclohexylmethyl)-nicotinamide,
5-(4-chloro-phenyl)-N-((1R,2R)-2-hydroxy-cyclohexyl)-6-(pyrimidin-2-ylmethoxy)-nicotinamide,
5-(4-chloro-phenyl)-N-((1R,2R)-2-hydroxy-cyclohexyl)-6-(pyridin-4-ylmethoxy)-nicotinamide,
cis-5-(4-chloro-phenyl)-N-(2-hydroxy-cyclohexylm-ethyl)-6-(pyridin-4-ylmethoxy)-nicotinamide,
5-(4-chloro-phenyl)-N-(2-hydroxymethyl-butyl)-6-(pyridin-4-ylmethoxy)-nicotinamide,
(RS)-5-(4-cyano-phenyl)-6-cyclopropylmethoxy-N-(2-hydroxymethyl-butyl)-nicotinamide,
5-(4-chloro-phenyl)-N-((R)-2-cyclopropyl-2-hydroxy-propyl)-6-cyclopropylmethoxy-nicotinamide,
5-(4-chloro-phenyl)-N-((R)-2-cyclopropyl-2-hydroxy-propyl)-6-(3-methyl-isoxazol-5-ylmethoxy)-nicotinamide,
(RS)-6-cyclopropylmethoxy-N-(2-hydroxymethyl-butyl)-5-(4-trifluoromethoxy-phenyl)-nicotinamide,
(RS)-6-cyclopropylmethoxy-N-(2-hydroxymethyl-butyl)-5-(4-trifluoromethyl-phenyl)-nicotinamide,
(−)-6-cyclopropylmethoxy-N-(2-hydroxymethyl-butyl)-5-(4-trifluoromethyl-phenyl)-nicotinamide,
(−)-cis-5-(4-Cyano-phenyl)-6-cyclopropylmethoxy-N-(2-hydroxy-cyclohexylmethyl)-nicotinamide,
(+)-cis-5-(4-cyano-phenyl)-6-cyclopropylmethoxy-N-(2-hydroxy-cyclohexylmethyl)-nicotinamide,
(−)-5-(4-cyano-phenyl)-6-cyclopropylmethoxy-N-((2-hydroxymethyl-butyl)-nicotinamide,
(+)-5-(4-cyano-phenyl)-6-cyclopropylmethoxy-N-((2-hydroxymethyl-butyl)-nicotinamide,
(+)-5-(4-cyano-phenyl)-N-(2-cyclopropyl-2-hydroxy-propyl)-6-cyclopropylmethoxy-nicotinamide,
6-cyclopropylmethoxy-5-(4-fluoro-phenyl)-N-(2-hydroxy-2-methyl-propyl)-nicotinamide,
(−)-6-cyclopropylmethoxy-N-(2-hydroxymethyl-butyl)-5-(4-trifluoromethoxy-phenyl)-nicotinamide,
6-cyclopropylmethoxy-5-(4-fluoro-phenyl)-N-(1-hydroxy-cyclopentylmethyl)-nicotinamide,
5-(4-chloro-phenyl)-N-((1R,2R)-2-hydroxy-cyclohexyl)-6-(pyridin-3-ylmethoxy)-nicotinamide,
5-(4-fluoro-phenyl)-N-((1R,2R)-2-hydroxy-cyclohexyl)-6-(pyridin-3-ylmethoxy)-nicotinamide,
5-(4-chloro-phenyl)-N-((R)-2-cyclopropyl-2-hydroxy-propyl)-6-(pyridin-3-ylmethoxy)-nicotinamide,
N-((R)-2-cyclopropyl-2-hydroxy-propyl)-5-(4-fluoro-phenyl)-6-(pyridin-3-ylmethoxy)-nicotinamide,
5-(4-chloro-phenyl)-N-((R)-2-cyclopropyl-2-hydroxy-propyl)-6-(3-methyl-pyridin-2-ylmethoxy)-nicotinamide,
N-((R)-2-cyclopropyl-2-hydroxy-propyl)-5-(4-fluoro-phenyl)-6-(3-methyl-pyridin-2-ylmethoxy)-nicotinamide,
5-(4-chloro-phenyl)-N-((1R,2R)-2-hydroxy-cyclohexyl)-6-[methyl-(4-methyl-thiazol-2-ylmethyl)-amino]-nicotinamide,
(RS)-N-(2-cyclobutyl-2-hydroxy-propyl)-6-cyclopropylmethoxy-5-(4-fluoro-phenyl)-nicotinamide,
5-(4-chloro-phenyl)-N-((1R,2R)-2-hydroxy-cyclohexyl)-6-(5-methyl-isoxazol-3-ylmethoxy)-nicotinamide,
5-(4-fluoro-phenyl)-N-((1R,2R)-2-hydroxy-cyclohexyl)-6-(5-methyl-isoxazol-3-ylmethoxy)-nicotinamide,
5-(4-chloro-phenyl)-N-((R)-2-cyclopropyl-2-hydroxy-propyl)-6-(5-methyl-isoxazol-3-ylmethoxy)-nicotinamide,
N-((R)-2-cyclopropyl-2-hydroxy-propyl)-5-(4-fluoro-phenyl)-6-(5-methyl-isoxazol-3-ylmethoxy)-nicotinamide,
N-((R)-2-cyclopropyl-2-hydroxy-propyl)-5-(4-fluoro-phenyl)-6-(pyridin-2-ylmethoxy)-nicotinamide,
(RS)-6-cyclopropylmethoxy-5-(4-fluoro-phenyl)-N-(3,3,3-trifluoro-2-hydroxy-2-methyl-propyl)-nicotinamide,
(RS)-6-cyclopropylmethoxy-N-(3,3,3-trifluoro-2-hydroxy-2-methyl-propyl)-5-(4-trifluoromethyl-phenyl)-nicotinamide,
(RS)-6-cyclopropylmethoxy-N-(3,3,3-trifluoro-2-hydroxy-2-methyl-propyl)-5-(4-trifluoromethoxy-phenyl)-nicotinamide,
5-(4-chloro-phenyl)-N-((1R,2R)-2-hydroxy-cyclohexyl)-6-(3-methyl-pyridin-2-ylmethoxy)-nicotinamide,
5-(4-fluoro-phenyl)-N-((1R,2R)-2-hydroxy-cyclohexyl)-6-(3-methyl-pyridin-2-ylmethoxy)-nicotinamide,
5-(4-chloro-phenyl)-N-((1R,2R)-2-hydroxy-cyclohexyl)-6-(pyridin-2-ylmethoxy)-nicotinamide,
5-(4-chloro-phenyl)-N-((R)-2-cyclopropyl-2-hydroxy-propyl)-6-(pyridin-2-ylmethoxy)-nicotinamide,
5-(4-fluoro-phenyl)-N-((1R,2R)-2-hydroxy-cyclohexyl)-6-(pyridin-2-ylmethoxy)-nicotinamide,
5-(4-fluoro-phenyl)-N-((R,2R)-2-hydroxy-cyclohexyl)-6-(pyridin-4-ylmethoxy)-nicotinamide,
N-((R)-2-cyclopropyl-2-hydroxy-propyl)-5-(4-fluoro-phenyl)-6-(pyridin-4-ylmethoxy)-nicotinamide,
5-(4-chloro-phenyl)-N-((R)-2-cyclopropyl-2-hydroxy-propyl)-6-(pyridin-4-ylmethoxy)-nicotinamide,
5-(4-cyano-phenyl)-6-cyclopropylmethoxy-N-((1R,2R)-2-hydroxy-cyclohexyl)-nicotinamide, or a pharmaceutically acceptable salt thereof.

17. The compound according to claim 1, selected from the group consisting of:
5-(4-chloro-phenyl)-6-cyclopropylmethoxy-N-((1R,2R)-2-hydroxy-cyclohexyl)-nicotinamide,
5-(4-chloro-phenyl)-N-((1R,2R)-2-hydroxy-cyclohexyl)-6-(2-methoxy-ethoxy)-nicotinamide,
N-((1R,2R)-2-hydroxy-cyclohexyl)-6-(2-methoxy-ethoxy)-5-(4-trifluoromethyl-phenyl)-nicotinamide,
6-cyclopropylmethoxy-5-(4-fluoro-phenyl)-N-((1R,2R)-2-hydroxy-cyclohexyl)-nicotinamide,
N-((R)-2-cyclopropyl-2-hydroxy-propyl)-6-cyclopropyl-methoxy-5-(4-fluoro-phenyl)-nicotinamide, 5-(4-chloro-phenyl)-N-((1R,2R)-2-hydroxy-cyclohexyl)-6-(pyrimidin-2-ylmethoxy)-nicotinamide, or a pharmaceutically acceptable salt thereof.

18. A process for the manufacture of a compound according to claim 1, comprising the steps of:

coupling a compound of formula

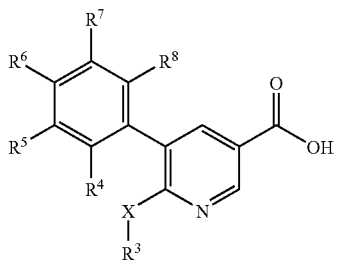
II wherein $R^3$ to $R^8$ are as defined in claim 1, with an amine of the formula

III wherein $R^1$ and $R^2$ are as defined in claim 1, with the help of an coupling agent under basic conditions, and, if desired, converting the resulting compound of formula I into a pharmaceutically acceptable salt thereof.

19. A process for the manufacture of a compound according to claim 1, comprising the steps of:

coupling a compound of formula

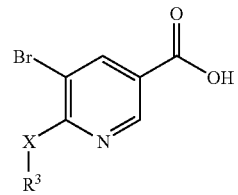
IV wherein X and $R^3$ are as defined herein before, with an aryl metal species of the formula

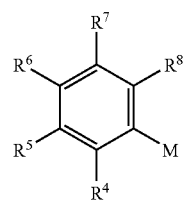
V wherein $R^4$ to $R^8$ are as defined herein before and M means boronic acid or a boronic acid ester, in the presence of a Pd catalyst under basic conditions, and, if desired, converting the resulting compound of formula I into a pharmaceutically acceptable salt thereof.

20. A pharmaceutical composition, comprising a therapeutically effective amount of a compound according to claim 1 and a pharmaceutically acceptable carrier and/or adjuvant.

* * * * *

UNITED STATES PATENT AND TRADEMARK OFFICE
CERTIFICATE OF CORRECTION

PATENT NO. : 7,229,999 B2  
APPLICATION NO. : 11/397743  
DATED : June 12, 2007  
INVENTOR(S) : Hebeisen et al.

Page 1 of 1

It is certified that error appears in the above-identified patent and that said Letters Patent is hereby corrected as shown below:

In Claim 16, col. 75, line 66-67, delete
"6-cyclopropylmethoxy-5-(2,4-dichloro-phenyl)-N-((R,2R)-2-hydroxy-cyclohexyl)-nicotinamide,"
and insert
--6-cyclopropylmethoxy-5-(2,4-dichloro-phenyl)-N-((1R,2R)-2-hydroxy-cyclohexyl)-nicotinamide,--

Claim 16, col. 76, lines 55-56 delete
"5-(4-chloro-phenyl)-6-cyclopentylmethoxy-N-((R,24)-2-hydroxy-cyclohexyl)-nicotinamide,"
and insert
--5-(4-chloro-phenyl)-6-cyclopentylmethoxy-N-((1R,24)-2-hydroxy-cyclohexyl)-nicotinamide,--

Claim 16, Col. 80, lines 44-45, delete
"5-(4-fluoro-phenyl)-N-((R,2R)-2-hydroxy-cyclohexyl)-6-(pyridine-4-ylmethoxy)-nicotinamide,"
and insert
--5-(4-fluoro-phenyl)-N-((1R,2R)-2-hydroxy-cyclohexyl)-6-(pyridine-4-ylmethoxy)-nicotinamide,--

Signed and Sealed this

Thirteenth Day of May, 2008

JON W. DUDAS  
*Director of the United States Patent and Trademark Office*